United States Patent
Wipf et al.

(10) Patent No.: US 10,174,031 B2
(45) Date of Patent: Jan. 8, 2019

(54) CALCIUM CHANNEL AGONISTS

(71) Applicant: University of Pittsburgh—Of the Commonwealth System of Higher Education, Pittsburgh, PA (US)

(72) Inventors: Peter Wipf, Pittsburgh, PA (US); Stephen D. Meriney, Pittsburgh, PA (US); Mary Liang, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 0 days.

(21) Appl. No.: 15/711,715

(22) Filed: Sep. 21, 2017

(65) Prior Publication Data
US 2018/0009810 A1    Jan. 11, 2018

Related U.S. Application Data

(62) Division of application No. 14/892,184, filed as application No. PCT/US2014/038574 on May 19, 2014, now Pat. No. 9,796,714.

(60) Provisional application No. 61/825,392, filed on May 20, 2013.

(51) Int. Cl.
| | |
|---|---|
| A61K 31/495 | (2006.01) |
| A61K 31/52 | (2006.01) |
| C07D 473/16 | (2006.01) |
| C07D 487/04 | (2006.01) |
| A61K 31/53 | (2006.01) |
| A61K 45/06 | (2006.01) |
| A61K 31/375 | (2006.01) |

(52) U.S. Cl.
CPC .......... *C07D 473/16* (2013.01); *A61K 31/375* (2013.01); *A61K 31/52* (2013.01); *A61K 31/53* (2013.01); *A61K 45/06* (2013.01); *C07D 487/04* (2013.01); *Y02A 50/469* (2018.01)

(58) Field of Classification Search
None
See application file for complete search history.

(56) References Cited

U.S. PATENT DOCUMENTS

| | | |
|---|---|---|
| 2010/0311767 A1 | 12/2010 | Nimmrich et al. |
| 2012/0149708 A1 | 6/2012 | Kashanchi |
| 2012/0184557 A1 | 7/2012 | Meijer et al. |
| 2013/0005747 A1 | 1/2013 | Green et al. |

FOREIGN PATENT DOCUMENTS

| | | |
|---|---|---|
| WO | WO 2010/019967 | 2/2010 |
| WO | WO 2011/089401 | 7/2011 |

OTHER PUBLICATIONS

Nimmrich, V. British Journal of Pharmacology (2012) 167 741-759).*
Cui, Chaochu. Acta Pharmaceutica Sinica B (2017; 7(1) 3-17.*
MedicineNet.com (2004) Web:http://www.medterms.com.*
Gilhus, Nils Erik. Autoimmune Diseases, vol. 2011, Article ID 973808, 5 pages, 2011.*
Adler et al., "Reversal of BoNT/A-mediated inhibition of muscle paralysis by 3,4-diaminopyridine and roscovitine in mouse phrenic nerve-hemidiaphragm preparations," *Neurochemistry Interational*, 61(6): 866-873, Nov. 2012.
CAS Registry No. 1025956-21-1, STN Entry Date Jun. 6, 2008.
CAS Registry No. 1348091-54-2, STN Entry Date Dec. 4, 2011.
International Search Report and Written Opinion issued for International Application No. PCT/US2014/038574 dated Aug. 12, 2014.
Legraverend et al., "Cyclin-dependent kinase inhibition by new C-2 alkynylated purine derivatives and molecular structure of a CDK-2-inhibitor complex," *Journal of Medicinal Chemistry*, 43(7): 1282-1292, Mar. 11, 2000.
Liang et al., "Synthesis and Biological Evaluation of (R)-Roscovitine Selective Calcium Channel Agonists," Poster presentation, May 20, 2014.
Liang et al., "Synthesis of biological evaluation of a selective N- and P/Q-type calcium channel agonist," *ACS Med. Chem. Lett.*, 3(12): 985-990, Oct. 1, 2012.
Meriney et al., "Novel calcium channel agonists as potential therapeutics in LEMS and other neuromuscular diseases," Poster presentation, May 20, 2014.
Meriney et al., "Novel calcium channel agonists as potential therapeutics in LEMS and other neuromuscular diseases," Presentation delivered May 22, 2012.

(Continued)

*Primary Examiner* — Deepak R Rao
*Assistant Examiner* — Laura M Daniel
(74) *Attorney, Agent, or Firm* — Klarquist Sparkman, LLP

(57) ABSTRACT

Embodiments of calcium channel agonists, as well as methods of making and using the calcium channel agonists, are disclosed. The disclosed calcium channel agonists and corresponding salt forms have a structure according to general formula I:

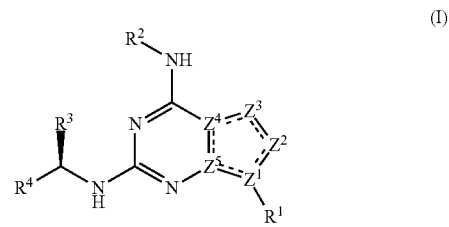

wherein each bond depicted as " ----- " is a single bond or a double bond as needed to satisfy valence requirements; $Z^1$, $Z^2$, $Z^3$, $Z^4$, and $Z^5$ independently are nitrogen or carbon; $R^1$ and $R^3$ are alkyl; $R^2$ is alkyl, aryl, heteroaryl, arylalkyl, or heteroarylalkyl; and $R^4$ is alkyl or hydroxyalkyl.

26 Claims, 11 Drawing Sheets

(56) References Cited

OTHER PUBLICATIONS

Oumata et al., "Roscovitine-Derived, Dual-Specificity Inhibitors of Cyclin-Dependent Kinases and Casein Kinases," *J. Med. Chem.*, vol. 51, pp. 5229-5242, 2008.

Popowycz et al., "Pyrazolo [1,5-a]-1,3,5-triazine as a purine bioisostere: Access to potent cyclin-dependent kinase inhibitor (R)-roscovitine analogue," *Journal of Medicinal Chemistry*, 52(3): 655-663, Jan. 7, 2009.

Taft et al., "The identification of inhibitors of *Schisostoma mansoni* miracidial transformation by incorporating a medium-throughput small-molecule screen," *Experimental Parasitology*, 125(2): 84-94, Jun. 2010.

Tarr et al., "New calcium channel agonists as potential therapeutics in Lambert-Eaton myasthenic syndrome and other neuromuscular diseases," *Annals of the New York Academy of Sciences*, No. 1275, pp. 85-91, Dec. 20, 2012.

\* cited by examiner

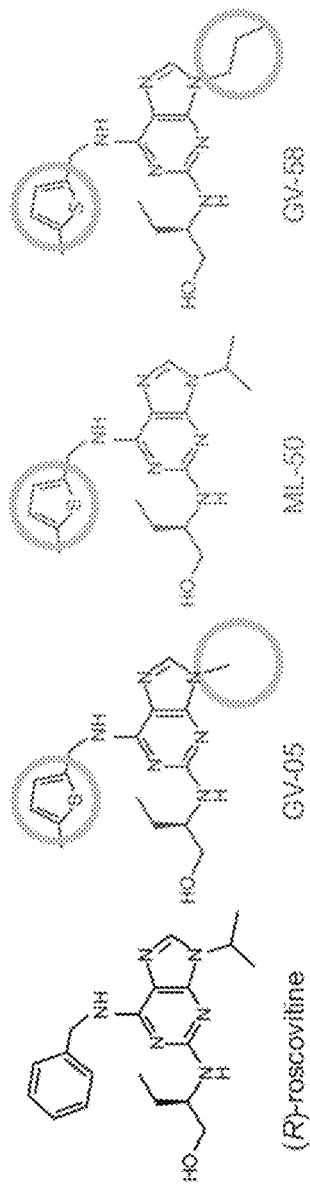
FIG. 3A
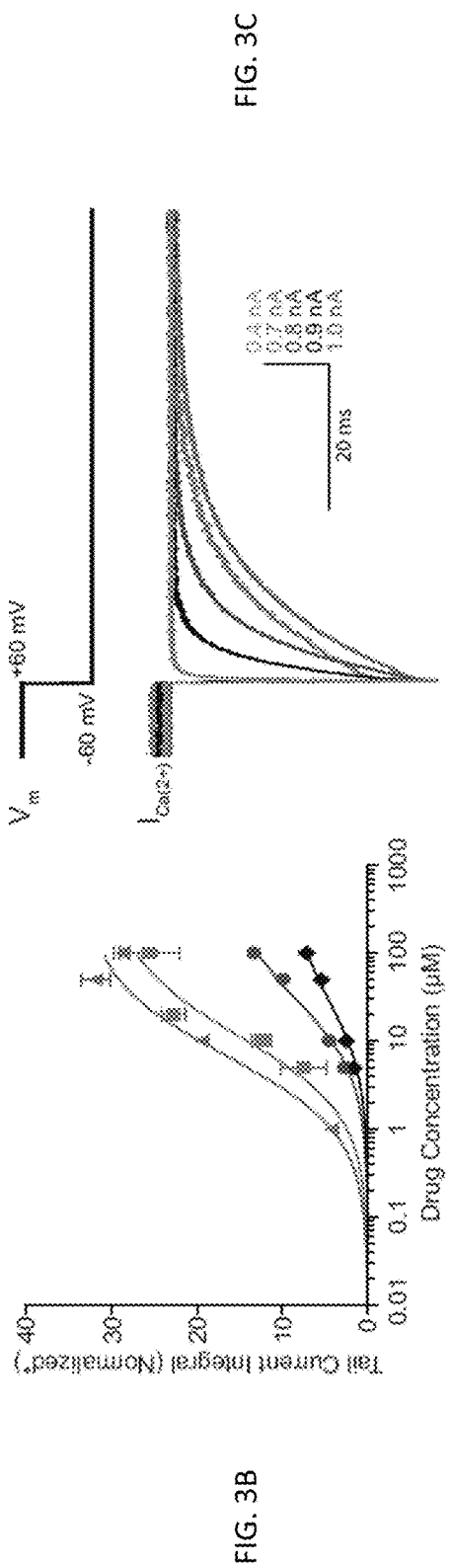
FIG. 3B
FIG. 3C

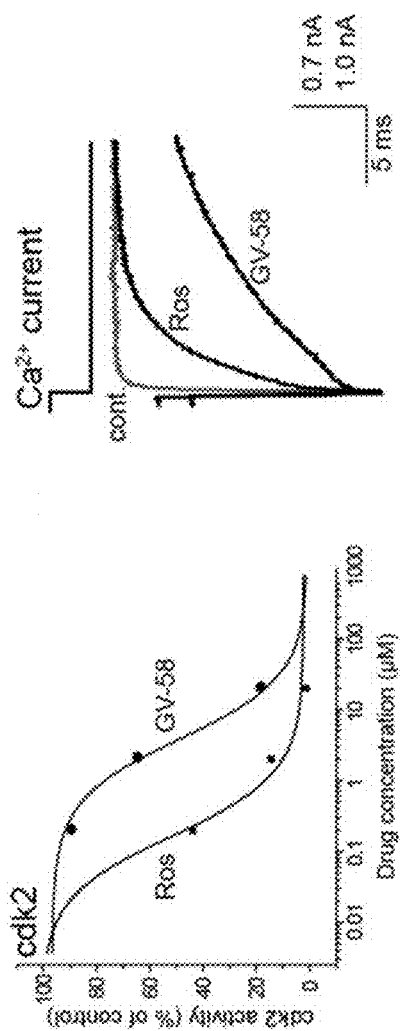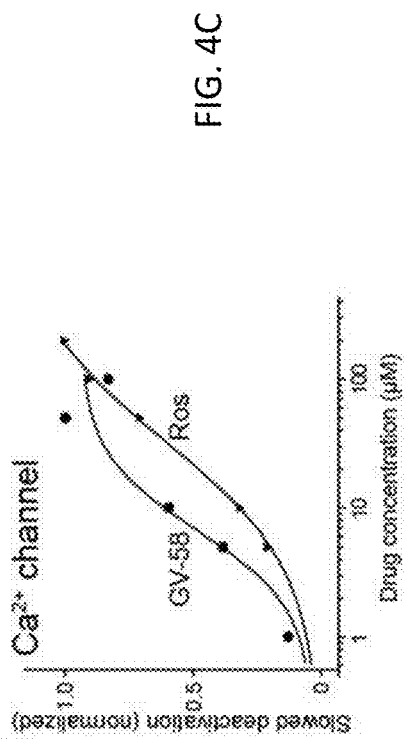
FIG. 4A
FIG. 4B
FIG. 4C

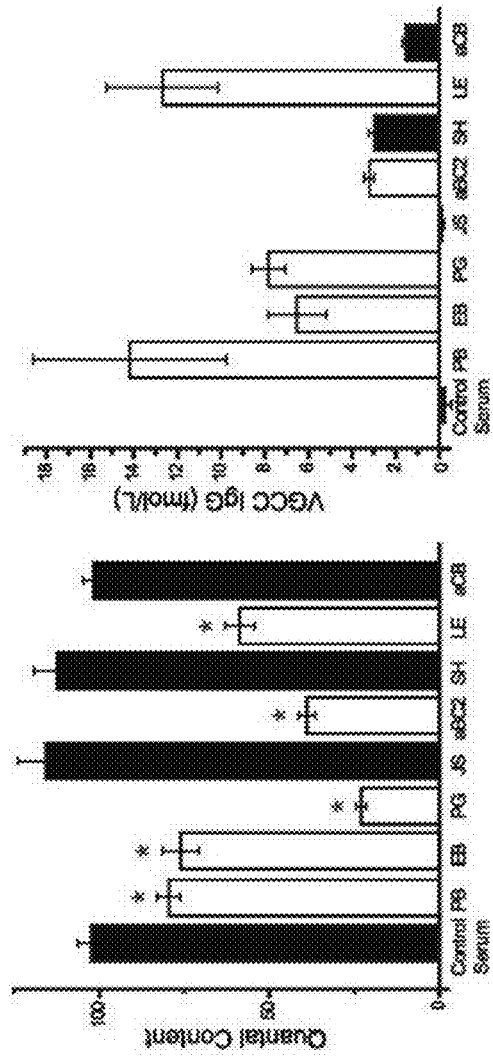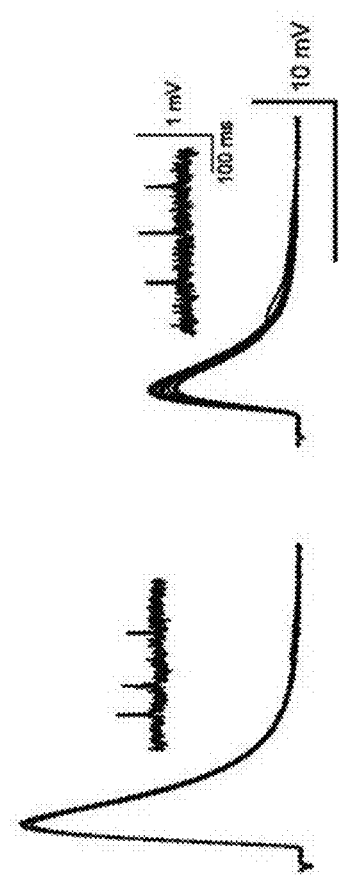
FIG. 7A
FIG. 7B
FIG. 7C

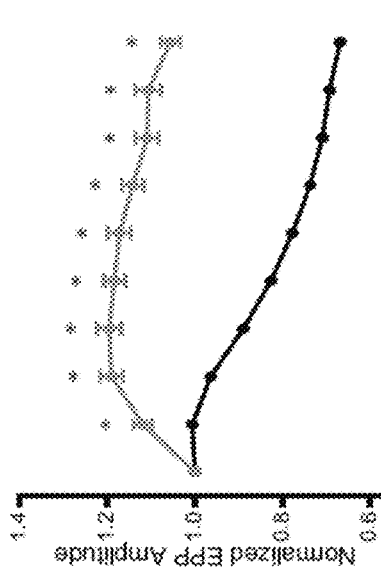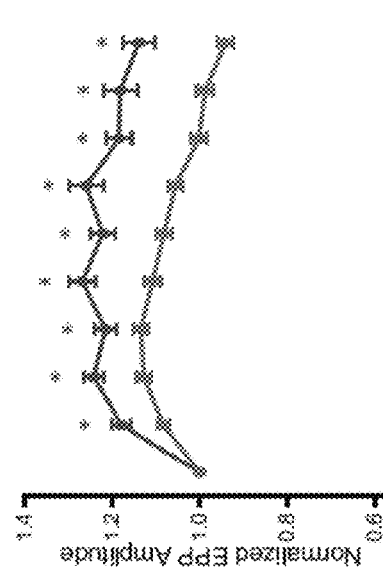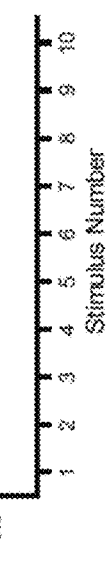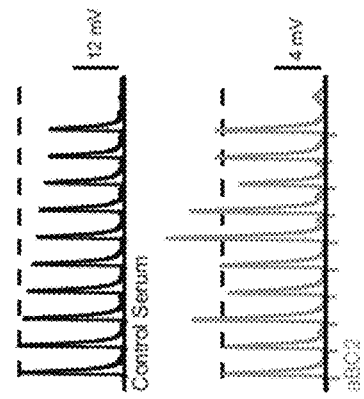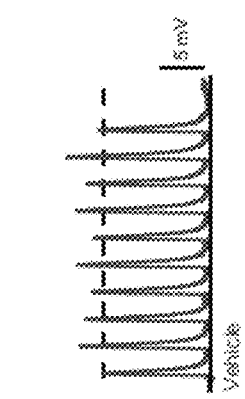
FIG. 9A
FIG. 9B
FIG. 9C
FIG. 9D

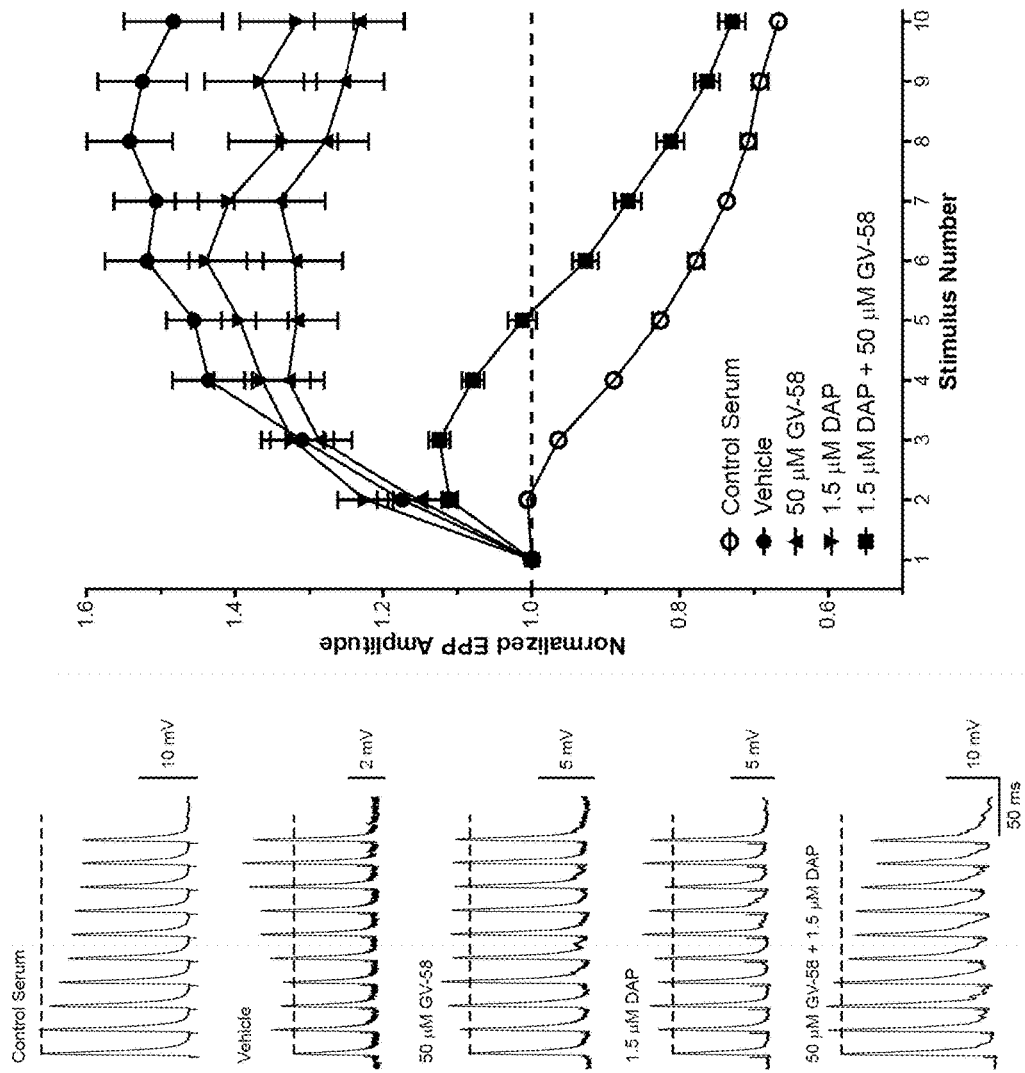

CALCIUM CHANNEL AGONISTS

RELATED APPLICATION

This application is a divisional of U.S. application Ser. No. 14/892,184, filed Nov. 18, 2015, which is the U.S. National Stage of International Application No. PCT/US2014/038574, filed May 19, 2014, which was published in English under PCT Article 21(2), which in turn claims the benefit of U.S. Provisional Application No. 61/825,392, filed May 20, 2013, which is incorporated herein by reference in its entirety.

ACKNOWLEDGMENT OF GOVERNMENT SUPPORT

This invention was made with government support under Grant Number GM067082 awarded by the National Institutes of Health and Grant Number 0844604 awarded by National Science Foundation. The government has certain rights in the invention.

FIELD

This disclosure concerns embodiments of calcium channel agonists, as well as methods of making and using the calcium channel agonists.

BACKGROUND

Chemical communication in the nervous system is tightly regulated by the flux of calcium ions through certain subtypes of voltage-gated channels. A decrease in calcium flux at synapses can cause neurological diseases. For example, Lambert-Eaton Myasthenic Syndrome (LEMS) is a neurological autoimmune disorder of the neuromuscular junction characterized by debilitating muscle weakness. While LEMS is often a paraneoplastic syndrome associated with small cell lung cancer, it can also be idiopathic. This muscle weakness has been shown to be due to an auto-antibody-mediated removal of a fraction of presynaptic P/Q-type (Cav2.1) calcium channels, which are known to be involved with transmitter release at the mammalian neuromuscular junction, and a partial compensatory up-regulation of N-type (Cav2.2), L-type (Cav1), and R-type (Cav2.3) channels. N-type and P/Q-type channels appear to be the most relevant for the control of transmitter release as they selectively bind directly to and co-localize with transmitter release sites. Despite a compensatory expression of other calcium channel types, the overall effect is a decrease in the quantal content of transmitter release from the NMJ. LEMS results in muscle weakness and is associated with compromised motor function. This disease is estimated to affect 1:100,000 individuals in the United States; however, the true incidence of LEMS remains unknown as it is often undiagnosed in patients.

Current treatment strategies are very limited, and those available are indirect and sometimes associated with undesirable side effects. If cancer is present, anti-tumor therapy is the priority. In any case, this type of neuromuscular weakness can be treated using either immunosuppressants or symptomatic treatment approaches Immunosuppressants have not been favored, as side-effects may be severe and include leukopenia, liver dysfunction, nausea, vomiting, and hair loss. The most common therapeutic approach is the use of the potassium channel blocker 3,4-diaminopyridine (DAP), which indirectly increases presynaptic $Ca^{2+}$ entry by broadening the action potential waveform, leading to an increase in transmitter release. In clinical trials, 10-20 mg of the potassium channel blocker 3,4-diaminopyridine (DAP), which increases calcium entry by broadening the action potential depolarization, was given 3 times per day, and led to serum levels of about 0.5 µM. However, DAP is only partially effective in LEMS. Although generally well-tolerated, DAP can have dose-limiting side-effects that include paresthesia, gastric symptoms, difficulty in sleeping, fatigue, and deterioration of muscle. The latter two may be due to reported effects on axonal $K^+$ channels that limit firing frequencies and/or reduction in activity-dependent facilitation caused by DAP. Thus, the current LEMS treatment approach indirectly increases calcium entry into the nerve terminal, but there are currently no other common treatment options.

Another disorder in which calcium channel agonists may be useful is myasthenia gravis. Myasthenia gravis is an autoimmune disorder characterized by blockade or loss of acetylcholine receptors at the neuromuscular junction. The symptoms of this disorder are often managed using acetylcholinesterase blockers.

Selective calcium channel agonists which increase the ion flux through N- and P/Q-type calcium channels represent attractive potential therapeutics for LEMS and other neuromuscular diseases; however, to date, no such agonists have been identified.

SUMMARY

Embodiments of calcium channel agonists, and pharmaceutical compositions including calcium channel agonists, are disclosed. Methods of making and using the calcium channel agonists also are disclosed. Embodiments of the disclosed compounds have a structure according to general formula I or a pharmaceutically acceptable salt thereof:

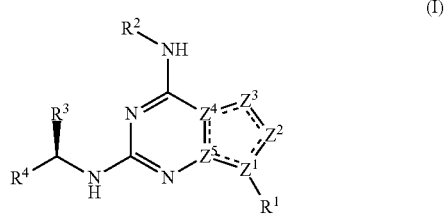

(I)

wherein each bond depicted as "- - - - -" is a single bond or a double bond as needed to satisfy valence requirements; $Z^1$, $Z^2$, $Z^3$, $Z^4$, and $Z^5$ independently are nitrogen or carbon; $R^1$ and $R^3$ are alkyl, such as $C_1$-$C_3$ alkyl; $R^2$ is alkyl, aryl, heteroaryl, arylalkyl, or heteroarylalkyl; and $R^4$ is alkyl or hydroxyalkyl, provided that: when $Z^1$ and $Z^3$ are nitrogen, $Z^2$, $Z^4$, and $Z^5$ are carbon, $R^1$ is 2-propyl, $R^3$ is ethyl, and $R^4$ is —$CH_2OH$, then $R^2$ is not benzyl or 2-hydroxybenzyl.

In some embodiments, two of $Z^1$, $Z^2$, $Z^3$, $Z^4$, and $Z^5$ are nitrogen. In certain embodiments, $Z^1$ and $Z^3$ are nitrogen, and $Z^2$, $Z^4$, and $Z^5$ are carbon.

In some embodiments, $R^1$ is n-alkyl. In one embodiment, $R^1$ is n-propyl. In some embodiments, $R^2$ is arylalkyl or heteroarylalkyl. In one embodiment, $R^2$ is substituted or unsubstituted thiophenyl methyl. In one embodiment, $R^3$ is ethyl. In another embodiment, $R^4$ is —$CH_2OH$.

One exemplary compound has the structure:

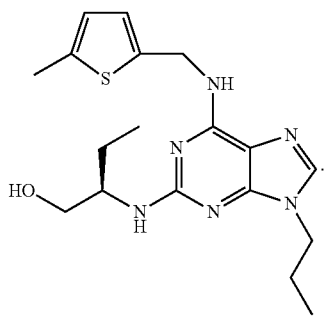 [SMILES: CCCn1cnc2c(NCc3ccc(C)s3)nc(N[C@H](CC)CO)nc21]

Embodiments of a pharmaceutical composition comprising a calcium channel agonist comprise at least one compound according to general formula I or a pharmaceutically acceptable salt thereof, and at least one pharmaceutically acceptable additive.

Embodiments of a method for treating condition mediated by calcium channel dysfunction include administering to a subject having, or suspected of having, a condition mediated by calcium channel dysfunction a therapeutically effective amount of a according to general formula I or a pharmaceutically acceptable salt thereof. Conditions mediated by calcium channel dysfunction include conditions that produce neuromuscular weakness. Exemplary conditions include Lambert-Eaton myasthenic syndrome, congenital myasthenic syndrome, myasthenia gravis (e.g., MuSK myasthenia gravis), botulism, botulinum toxin overdose, a peripheral demyelinating disorder (e.g., Guillain-Barré syndrome, chronic inflammatory demyelinating polyneuropathy, anti-MAG peripheral neuropathy, Charcot-Marie-Tooth disease, copper deficiency), a motor neuron disease (e.g., spinal muscular atrophy, amyotrophic lateral sclerosis, primary lateral sclerosis, progressive bulbar palsy, pseudobulbar palsy), or a combination thereof.

In some embodiments, the compound has a $Ca^{2+}$ channel activity half maximal effective concentration, $EC_{50}$, of ≤50 μM. The compound may have a cyclin-dependent kinase 2 $EC_{50}$ of at least 0.2 μM. In certain embodiments, the compound has an N-type and/or P/Q-type $Ca^{2+}$ channel activity $EC_{50}$ that is at least 10-fold less than an L-type $Ca^{2+}$ channel activity $EC_{50}$ of the compound.

Embodiments of the disclosed method may further include administering to the subject a therapeutically effective amount of an acetylcholinesterase inhibitor, an immunosuppressant, intravenous immunoglobulins, a glucocorticoid, ascorbic acid, an anti-cancer agent, a potassium channel blocker, a copper supplement, an analgesic, an antidepressant, a muscle relaxant, or a combination thereof. When the condition is Lambert-Eaton myasthenic syndrome, the method may further include administering to the subject a therapeutically effective amount of 3,4-diaminopyridine.

The foregoing and other objects, features, and advantages of the invention will become more apparent from the following detailed description, which proceeds with reference to the accompanying figures.

BRIEF DESCRIPTION OF THE DRAWINGS

FIG. 3A shows the chemical structures of (R)-roscovitine and 3 analogs: compounds 13u, 13w, 13x. Circles indicate structural differences compared to (R)-roscovitine.

FIG. 3B is a series of $Ca^{2+}$ channel agonist activity dose-response curves for each of the compounds shown in FIG. 3A: (R)-roscovitine (♦), 13u (■), 13w (●), and 13x (▲). Each analog-modified tail current integral was normalized to its peak tail current and then divided by its respective control (untreated) tail current integral (also normalized to its respective peak current) to calculate the final value. Error bars indicate standard error of the mean (s.e.m.).

FIG. 3C illustrates representative tail current traces for each of the compounds, along with a control tail current trace for comparison.

FIG. 4A is a plot of cdk activity measured at varying concentrations of (R)-roscovitine and compound 13x. Compound 13x inhibits cdk2 at more than 20-fold higher concentration than (R)-roscovitine.

FIG. 4B illustrates calcium tail current (bottom traces) evoked by a repolarizing voltage step (top trace). Under control conditions (cont; no drugs), calcium current decays very quickly. After exposure to (R)-roscovitine (Ros), decay of calcium current is significantly slowed. Exposure to a newly developed analog of (R)-roscovitine (13x) slows calcium current deactivation more dramatically than (R)-roscovitine.

FIG. 4C is a dose response curve for (R)-roscovitine (Ros) and compound 13x demonstrating that 13x has a 6-fold higher affinity for the calcium channel than (R)-roscovitine.

FIG. 7A is a graph showing an evaluation of several patients' serum evaluated in a LEMS passive transfer model by measuring quantal content following the passive transfer protocol. White bars indicate a significant decrease in quantal content compared to control serum-treated NMJs, while black bars indicate no significant difference from control serum-treated NMJs.

FIG. 7B is a graph showing an evaluation of the serum samples of FIG. 7A for levels of voltage-gated $Ca^{2+}$ channel (VGCC) antibodies.

FIG. 7C illustrates sample mEPP (miniature end plate potential, insets) and EPP (end plate potential) traces from a representative control (left panel) and aBC2 serum-treated (right panel) NMJ. Treatment with aBC2 serum resulted in a decrease in EPP amplitude, but no change in average mEPP amplitude. Error bars indicate s.e.m.

FIG. 9A shows representative EPPs evoked by 50 Hz stimuli recorded from terminals in control serum-injected mice and aBC2 LEMS serum-injected mice.

FIG. 9B is a plot of the average 50 Hz train data normalized to the amplitude of the first EPP of the train for the two conditions shown in FIG. 9A. Error bars indicate s.e.m.

FIG. 9C shows representative 50 Hz trains for aBC2 LEMS serum-injected mice in the presence of the DMSO vehicle and aBC2 LEMS serum-injected mice following application of 50 µM 13x.

FIG. 9D is a plot of the average 50 Hz train data normalized to the amplitude of the first EPP of the train for the two conditions shown in FIG. 9C. Error bars indicate s.e.m.

FIG. 10A—Sample traces showing the average EPP amplitudes following exposure to a variety of conditions. Left: sample average EPP recorded from a NMJ of a control serum-treated mouse. Middle: sample average EPPs of a LEMS model NMJ before and after application of 50 µM GV58 (also referred to herein as compound 13x). Right: sample average EPPs recorded from a LEMS model NMJ before drug application (LEMS), following application of 1.5 µM DAP, and following application of 50 µM GV-58 plus 1.5 µM DAP. FIG. 10B Plot of the quantal content for NMJs in each of the five conditions: NMJs from control serum-treated mice (n=41), LEMS model NMJs in the presence of the vehicle (n=63), LEMS model NMJs following application of 50 µM GV-58 (n=20), LEMS model NMJs following application of 1.5 µM DAP (n=21) and LEMS model NMJs following application of 50 µM GV-58 plus 1.5 µM DAP (n=63). Data are represented as mean±s.e.m.

FIGS. 11A and 11B. The synergistic effect of GV-58 plus DAP elicits a near complete restoration of short-term synaptic plasticity characteristics in LEMS model NMJs. FIG. 11A Sample EPPs recorded from NMJs in each of the five conditions during a 50 Hz train of 10 stimuli. Dashed lines indicate the amplitude of the first EPP in each train. FIG. 11B Plot of the average change in EPP amplitude during a 50 Hz stimulus train for NMJs from control serum-treated mice (n=41), LEMS model NMJs in vehicle (n=75), LEMS model NMJs after application of 50 µM GV-58 (n=24), LEMS model NMJs following application of 1.5 µM DAP (n=21), and LEMS model NMJs following application of 50 µM GV-58 plus 1.5 µM DAP (n=75). Each EPP in the train is first normalized to the first EPP in the train before averaging responses from many trials. The average normalized values are then plotted for each treatment condition. Data are represented as mean±s.e.m. Dashed line represents no change from the amplitude of the first EPP in the train.

DETAILED DESCRIPTION

Figure 1:
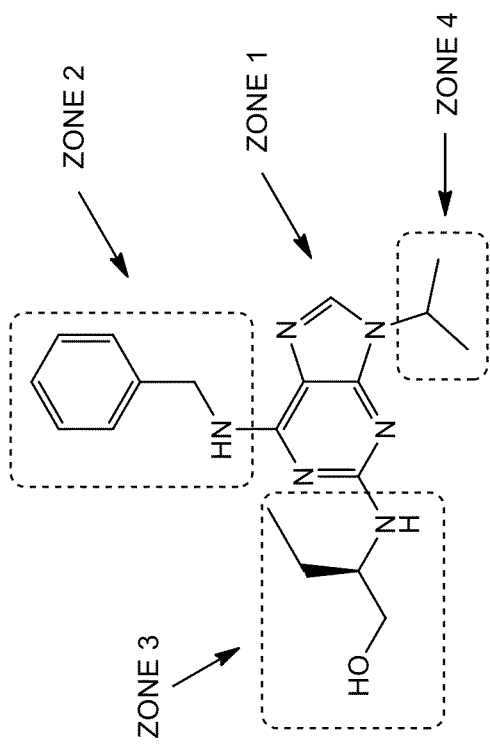
FIG. 1 is the molecular structure of (R)-roscovitine.

Embodiments of calcium channel agonists are disclosed. Methods of making and using the calcium channel agonists also are disclosed.

The disclosed compounds are analogs of (R)-roscovitine. Some embodiments of the disclosed compounds have an increased agonist effect for $Ca^{2+}$ channels, have a more potent effect on $Ca^{2+}$ current, and also exhibit reduced kinase (e.g., cyclin-dependent kinase) activity compared to (R)-roscovitine. Certain embodiments of the disclosed calcium channel agonists target presynaptic $Ca^{2+}$ channels and can partially restore the deficiency of transmitter release in a LEMS passive transfer mouse model neuromuscular junction.

I. Terms and Abbreviations

The following explanations of terms and abbreviations are provided to better describe the present disclosure and to guide those of ordinary skill in the art in the practice of the present disclosure. As used herein, "comprising" means "including" and the singular forms "a" or "an" or "the" include plural references unless the context clearly dictates otherwise. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

Unless otherwise indicated, all numbers expressing quantities of reactants and products, properties such as molecular weight, percentages, dosages, and so forth, as used in the specification or claims are to be understood as being modified by the term "about." Accordingly, unless otherwise indicated, implicitly or explicitly, the numerical parameters and/or non-numerical properties set forth are approximations that may depend on the desired properties sought, limits of detection under standard test conditions/methods, limitations of the processing method, and/or the nature of the parameter or property. When directly and explicitly distinguishing embodiments from discussed prior art, the embodiment numbers are not approximates unless the word "about" is recited.

Definitions of common terms in chemistry may be found in Richard J. Lewis, Sr. (ed.), *Hawley's Condensed Chemical Dictionary*, published by John Wiley & Sons, Inc., 1997 (ISBN 0-471-29205-2). Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

In order to facilitate review of the various embodiments of the disclosure, the following explanations of specific terms are provided:

Agonist: A compound that binds to a receptor or an enzyme and produces an action. For example, an agonist that binds to a cellular receptor initiates a physiological or pharmacological response characteristic of that receptor. An agonist that binds to an enzyme activates the enzyme. An antagonist blocks an action of an agonist.

Alkyl: A hydrocarbon group having a saturated carbon chain. The chain may be cyclic, branched or unbranched. The term lower alkyl means the chain includes 1-10 carbon atoms. Unless otherwise stated, the alkyl group may be substituted or unsubstituted.

Aralkyl or arylalkyl: An aryl group (such as a phenyl group) appended to an alkyl radical including, but not limited to, benzyl, ethylbenzene, propylbenzene, butylbenzene, pentylbenzene, and the like. Conversely the term "phenylalkyl" refers to a phenyl group appended to an alkyl radical. Aralkyl groups, such as benzyl groups, may be unsubstituted or substituted with one, two or three substituents, with substituent(s) independently selected from alkyl, heteroalkyl, aliphatic, heteroaliphatic, thioalkoxy, haloalkyl (such as —CF$_3$), halo, nitro, cyano, —OR (where R is hydrogen or alkyl), —N(R)R' (where R and R' are independently of each other hydrogen or alkyl), —COOR (where R is hydrogen or alkyl) or —C(O)N(R')R" (where R' and R" are independently selected from hydrogen or alkyl). Non-limiting examples, include o-, m-, and/or p-chlorobenzyl, o-, m-, and/or p-methoxybenzyl, and o-, m-, and/or p-(trifluoromethyl)benzyl. Unless otherwise stated, the aralkyl or arylalkyl group may be substituted or unsubstituted.

Aryl: A monovalent aromatic carbocyclic group of, unless specified otherwise, from 6 to 15 carbon atoms having a single ring (e.g., phenyl, isoxazole) or multiple condensed rings which condensed rings may or may not be aromatic (e.g., quinolone, indole, benzodioxole, and the like), provided that the point of attachment is through an atom of an aromatic portion of the aryl group and the aromatic portion at the point of attachment contains only carbons in the aromatic ring. If any aromatic ring portion contains a heteroatom, the group is a heteroaryl and not an aryl. Aryl groups are monocyclic, bicyclic, tricyclic or tetracyclic. Unless otherwise stated, the aryl group may be substituted or unsubstituted.

Calcium channel: An ion channel, which is selectively permeable to calcium ions. Voltage-dependent calcium channels (VDCCs) are found in membranes of certain cells, such as muscle cells and neurons. A VDCC is normally closed. When activated, or opened, the VDCC allows Ca$^{2+}$ to enter the cell, thereby resulting in, e.g., muscular contraction, neuronal excitation, or neurotransmitter release, depending on the cell type.

Cycloalkyl: A saturated monovalent cyclic hydrocarbon radical of three to seven ring carbons, e.g., cyclopentyl, cyclohexyl, cycloheptyl and the like. Unless otherwise stated, the cycloalkyl group may be substituted or unsubstituted.

Effective amount or therapeutically effective dose: An amount sufficient to provide a beneficial, or therapeutic, effect to a subject or a given percentage of subjects.

Heteroaryl: An aromatic compound or group having at least one heteroatom, i.e., one or more carbon atoms in the ring has been replaced with an atom having at least one lone pair of electrons, typically nitrogen, oxygen, phosphorus, silicon, or sulfur. Unless otherwise stated, the heteroaryl group may be substituted or unsubstituted.

Heteroarylalkyl: An arylalkyl radical as defined above containing at least one heteroatom in the aryl group, typically nitrogen, oxygen, phosphorus, silicon, or sulfur. Unless otherwise stated, the heteroarylalkyl group may be substituted or unsubstituted.

Hydroxyalkyl: An alkyl radical substituted with at least one hydroxyl group. In some examples, a hydroxyalkyl group has the general formula —ROH where R is alkyl, such as lower alkyl. Unless otherwise stated, R may be substituted or unsubstituted. Exemplary hydroxyalkyl groups include hydroxymethyl (—CH$_2$OH) and hydroxyethyl (—CH$_2$CH$_2$OH).

Pharmaceutically acceptable salt: A biologically compatible salt of a compound that can be used as a drug, which salts are derived from a variety of organic and inorganic counter ions well known in the art.

Selectivity: As used herein, selectivity refers to the ability of a compound to preferentially affect activity of a particular calcium channel and/or kinase. For example, the compound may preferentially activate N and/or P/Q-type over L-type calcium channels.

Stereochemistry: The relative spatial arrangement of atoms that form the structure of a molecule. Compounds with the same molecular formula and sequence of bonded atoms, but which differ only in the three-dimensional orientation of the atoms in space, are called stereoisomers.

Subject: An animal or human subjected to a treatment, observation or experiment.

Substituent: An atom or group of atoms that replaces another atom in a molecule as the result of a reaction. The term "substituent" typically refers to an atom or group of atoms that replaces a hydrogen atom on a parent hydrocarbon chain or ring.

Substituted: A fundamental compound, such as an aryl or alkyl compound, or a radical thereof, having coupled thereto, typically in place of a hydrogen atom, a second substituent. For example, substituted aryl compounds or substituents may have an aliphatic group coupled to the closed ring of the aryl base, such as with toluene. Again solely by way of example and without limitation, a hydrocarbon may have a substituent bonded thereto, such as one or more halogens, an aryl group, a cyclic group, a heteroaryl group or a heterocyclic group.

Treating or treatment: With respect to disease, either term includes (1) preventing the disease, e.g., causing the clinical symptoms of the disease not to develop in an animal that may be exposed to or predisposed to the disease but does not yet experience or display symptoms of the disease, (2) inhibiting the disease, e.g., arresting the development of the disease or its clinical symptoms, or (3) relieving the disease, e.g., causing regression of the disease or its clinical symptoms.

II. Calcium Channel Agonists (R)-Roscovitine (FIG. 1) is a trisubstituted purine that was originally developed as a cyclin-dependent kinase (cdk) inhibitor. Cdks have been implicated in neuronal development, synaptic transmission, cytoskeletal control, neurodegeneration, and cell cycle control. In terms of clinical use, some inhibitors of cdks are being tested for use as anti-cancer drugs and in the treatment of neurodegenerative diseases. Roscovitine is a chiral compound, and both (R) and (S) configurations are effective cdk inhibitors. The phenyl ring, isopropyl group, and ethyl group attached to stereogenic carbon of roscovitine are involved in hydrophobic interactions within the ATP binding site of cdk. (R)-roscovitine is also a potent agonist for a subset of voltage-gated calcium channels, i.e., N- and P/Q-type calcium channels.

These channel subtypes are the two major subtypes that regulate chemical transmitter release in the nervous system. (R)-Roscovitine slows the deactivation kinetics of N- and P/Q-type $Ca^{2+}$ channels by increasing their mean open time, which leads to an increase in transmitter release at synapses. Although (R)-roscovitine does target the $Ca^{2+}$ channels involved in transmitter release at the NMJ, the potent (R)-roscovitine-mediated inhibition of cdks presents a potential source of undesirable side-effects if used for the treatment of LEMS. The development of a selective agonist for N- and P/Q-type calcium channels could have a significant impact on the treatment of LEMS as well as other neurological diseases.

At the single channel level, it is known that calcium channels normally gate with a short (predominant) or long (rare) mean open time. It has been shown that (R)-roscovitine significantly prolongs the mean open time of calcium channels gating with a long open time, and increases the probability of observing channels that gate with a long open time. These effects lead to increased calcium flux when channels are naturally activated by an action potential, which increases transmitter release at neuromuscular and CNS synapses.

Embodiments of (R)-roscovitine analogs and corresponding pharmaceutically acceptable salts are disclosed. In some embodiments, the compounds are selective voltage-gated calcium channel agonists, e.g., N- and/or P/Q-type calcium channel agonists. Certain embodiments of the disclosed compounds slow deactivation (closing) of the calcium channel, resulting in increased calcium entry during motor nerve action potential activity. The compounds also may have decreased kinase activity, such as decreased cyclin-dependent kinase (cdk) activity.

Desirably, (R)-roscovitine analogs would exhibit 10-100 times reduced cdk activity and stronger, 10-100 times higher affinity calcium channel agonist effects that would be appropriate to treat neuromuscular weakness mediated by calcium channel dysfunction. A 4-zone approach (FIG. 1) was used for initial medicinal chemistry structure activity relationship (SAR) studies. Zone 1 modifications indicated that some minor structural changes were not deleterious to calcium channel activity. In zone 2, calcium channel agonist activity was more potent when the nitrogen was substituted with a hydrogen atom; modifications to the aryl ring were permitted. When the stereochemistry in zone 3 was altered, the desired $Ca^{2+}$ channel agonist activity was lost. In zone 4, some modifications were acceptable.

The potential side-effects of a use-dependent N- and P/Q-type calcium channel agonist that enhances calcium flux through calcium channels that are normally activated by action potential activity are expected to be few and manageable. This expectation is based on an extensive clinical literature that uses an indirect method of achieving a similar outcome with potassium channel blockers such as 3,4-diaminopyridine (DAP). DAP prolongs the duration of the pre-synaptic action potential and this indirectly increases the activation of all voltage-gated calcium channels in the peripheral nervous system. DAP is generally well tolerated by LEMS patients, with many of the side-effects reported likely due to either broadening of action potentials in all neurons or the non-selective indirect effect of increasing calcium flux through all voltage-gated channels. Based on these previous reports, selective use-dependent N- and P/Q-type calcium channel agonists are predicted to be well tolerated.

Embodiments of the disclosed calcium channel agonists and corresponding salt forms have a structure and stereochemistry according to general formula I:

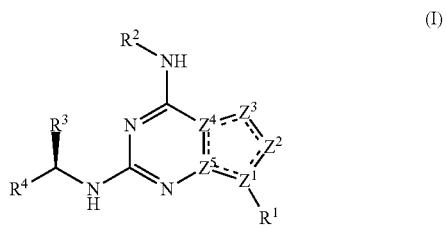

(I)

wherein each bond depicted as "-----" is a single bond or a double bond as needed to satisfy valence requirements; $Z^1$, $Z^2$, $Z^3$, $Z^4$, and $Z^5$ independently are nitrogen or carbon; $R^1$ and $R^3$ are alkyl; $R^2$ is alkyl, cycloalkyl, aryl, heteroaryl, arylalkyl, or heteroarylalkyl; and $R^4$ is alkyl or hydroxyalkyl, provided that when $Z^1$ and $Z^3$ are nitrogen, $Z^2$, $Z^4$, and $Z^5$ are carbon, $R^1$ is 2-propyl, $R^3$ is ethyl, and $R^4$ is —$CH_2OH$, then $R^2$ is not benzyl or 2-hydroxybenzyl.

In some embodiments, two of $Z^1$, $Z^2$, $Z^3$, $Z^4$, and $Z^5$ are nitrogen. In one embodiment, $Z^1$ and $Z^3$ are nitrogen, and $Z^2$, $Z^4$, and $Z^5$ are carbon. In another embodiment, $Z^1$ and $Z^2$ are nitrogen, and $Z^3$, $Z^4$, and $Z^5$ are carbon. In yet another embodiment, $Z^1$ and $Z^5$ are nitrogen, and $Z^2$, $Z^3$, and $Z^4$ are carbon.

In some embodiments, $R^1$ is n-alkyl, such as lower n-alkyl. In certain examples, $R^1$ is $C_1$-$C_3$ alkyl, e.g., methyl, ethyl, n-propyl, or 2-propyl. In some embodiments, $R^2$ is arylalkyl or heteroarylalkyl. In certain examples, $R^2$ is heteroarylalkyl, e.g., substituted or unsubstituted thiophenyl methyl.

In some embodiments, $R^3$ is lower alkyl. In one embodiment, $R^3$ is ethyl. In certain embodiments, $R^4$ is hydroxyalkyl, such as —$R^5OH$, where $R^5$ is lower alkyl, for example, $C_1$-$C_3$ alkyl. In one embodiment, $R^4$ is hydroxymethyl.

In some embodiments, the calcium channel agonist is a pharmaceutically acceptable salt form of a compound according to general formula I. Suitable salts may include sodium salts, potassium salts, arginine salts, choline salts, calcium salts, and pharmaceutically acceptable acid or base addition salts, but generally any pharmaceutically acceptable salt may be used for methods described herein. Generally, pharmaceutically acceptable salts are those salts that retain substantially one or more of the desired pharmacological activities of the parent compound and which are suitable for administration to humans.

Exemplary compounds 13a-13x according to formula I are shown in Table 1. In each of compounds 13a-13x, $Z^1$ and $Z^3$ are nitrogen, $Z^2$, $Z^4$, and $Z^5$ are carbon, $R^3$ is ethyl, and $R^4$ is —$CH_2OH$.

TABLE 1

| Compound | $R^1$ | $R^2$ |
|---|---|---|
| (R)-roscovitine | i-Pr | Bn |
| 13a | Pr | $CH_2$(biphenyl) |
| 13b | Pr | $CH(Ph)_2$ |
| 13c | Pr | $(CH_2)_2Ph$ |
| 13d | Pr | Bn |
| 13e | Pr | Ph |
| 13f | Pr | $CH_2$(3-Py) |
| 13g | Pr | $CH_2CH(CH_2)_2$ |

TABLE 1-continued

Figure 2:
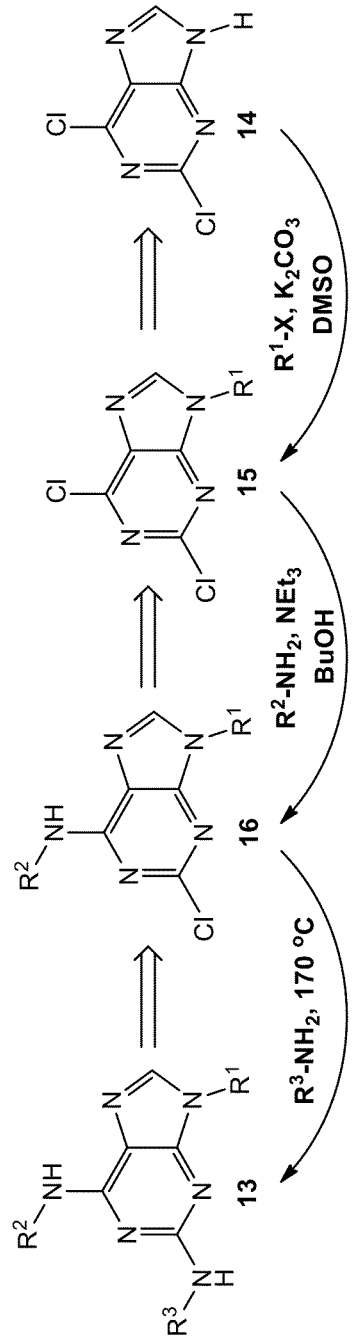
FIG. 2 is a scheme illustrating a synthetic strategy used to make selective $Ca^{2+}$ channel agonists.

| Compound | $R^1$ | $R^2$ |
|---|---|---|
| 13h | Me | $CH_2$(biphenyl) |
| 13i | Me | $CH(Ph)_2$ |
| 13j | Me | $(CH_2)_2Ph$ |
| 13k | Me | Bn |
| 13l | Me | Ph |
| 13m | Me | $CH_2CH(CH2)_2$ |
| 13n | Me | $CH_2$(3-Py) |
| 13o | Pr | $CH_2$[(p-trifluoromethyl)phenyl] |
| 13p | i-Pr | $CH_2CH(CH_2)_2$ |
| 13q | i-Pr | $(CH_2)_2Ph$ |
| 13r | i-Pr | $CH_2$(3-Py) |
| 13s | i-Pr | $CH_2$(biphenyl) |
| 13t | i-Pr | $CH(Ph)_2$ |
| 13u | i-Pr | $CH_2$[(2-methyl)5-thiophenyl] |
| 13v | i-Pr | $CH_2$[(m-trifluoromethyl)5-thiophenyl] |
| 13w | Me | $CH_2$[(2-methyl)5-thiophenyl] |
| 13x | Pr | $CH_2$[(2-methyl)5-thiophenyl] | i-Pr = isopropyl,
Pr = propyl,
Me = methyl,
Bn = benzyl,
Ph = phenyl,
Py = pyridine III. Compound Synthesis A synthetic strategy useful for making some embodiments of selective $Ca^{2+}$ channel agonists is summarized in FIG. 2. Starting with the commercially available 2,6-dichloropurine 14, N-9 alkylation of the purine with primary alkyl halides leads to intermediate 15. Preferential $S_NAr$ reaction at the more reactive C-6 position followed by displacement of the C-2 chloride with primary amines provides target analogs 13.

Zone 4 modifications are achieved by subjecting dichloropurine 14 to a deprotonation in dimethyl sulfoxide (DMSO) in the presence of a mild base such as potassium carbonate, followed by the addition of alkyl bromides or iodides at 16-18° C. Primary alkyl halides ($R^1$=Me, Pr) provide a similar yield (64-78%) to the secondary alkyl halide ($R^1$=i-Pr, 65%). Microwave irradiation at 120° C. for 20 minutes in n-butanol and triethylamine with various aryl- and alkylamines converts intermediates 15 to the C-6 aminated purines 16 in moderate-to-good yields (52-95%). Finally, aminolysis at C-2 under forcing conditions (e.g., heating neat in a sealed flask at 170° C. in the presence of the $R^3$-amine for 8-15 hours) introduces an (R)-2-amino-1-butanol side chain to give target molecules 13 in variable yields (25-93%).[5]

IV. Methods of Use

A. Treatment of Conditions Mediated by $Ca^{2+}$ Channel Dysfunction

Embodiments of the disclosed calcium channel agonists are useful for treating conditions mediated by calcium channel dysfunction, including conditions that produce neuromuscular weakness. Exemplary conditions include, but are not limited to Lambert-Eaton Myasthenic Syndrome (LEMS), congenital myasthenic syndrome (a heterogeneous group of inherited disorders caused by mutations in any one of >10 genes that code for synaptic proteins, leading to impaired neuromuscular function), myasthenia gravis (e.g., MuSK myasthenia gravis—characterized by antibodies against the MuSK protein (muscle specific kinase), a tyrosine kinase receptor required for formation of neuromuscular junctions), botulism, botulinum toxin overdose (e.g., from onabotulinumtoxin A injections (Botox) for therapeutic and cosmetic purposes), a peripheral demyelinating disorder (e.g., Guillain-Barré syndrome, chronic inflammatory demyelinating polyneuropathy, anti-MAG peripheral neuropathy, Charcot-Marie-Tooth disease, copper deficiency), a motor neuron disease (e.g., spinal muscular atrophy, amyotrophic lateral sclerosis, primary lateral sclerosis, progressive bulbar palsy, pseudobulbar palsy), or a combination thereof.

In some embodiments, an effective amount of a compound according to general formula I or a pharmaceutically acceptable salt thereof is administered to a subject having, or suspected of having, a condition mediated by calcium channel dysfunction, or a subject for whom a calcium channel agonist would improve the symptoms resulting from a neurologic disorder not mediated by calcium channel dysfunction.

The calcium channel agonists described herein, or compositions thereof, will generally be used in an amount effective to achieve the intended result, for example in an amount effective to treat a condition mediated by calcium channel dysfunction. By therapeutic benefit is meant eradication or amelioration of one or more of the symptoms associated with the underlying disorder such that the subject reports an improvement in feeling or condition, notwithstanding that the subject may still be afflicted with the underlying disorder.

The amount of compound administered will depend upon a variety of factors, including, for example, the particular condition being treated, the mode of administration, the severity of the condition being treated and the age and weight of the patient, the bioavailability of the particular active compound, etc. Determination of an effective dosage is well within the capabilities of those skilled in the art. A skilled practitioner will be able to determine the optimal dose for a particular individual. Effective dosages may be estimated initially from in vitro or in vivo assays. For example, an initial dosage for use in animals may be formulated to achieve a circulating blood or serum concentration of active compound that is at or above an $EC_{50}$ of the particular compound as measured in an in vitro assay or an in vivo assay as described below in Example 3. Calculating dosages to achieve such circulating blood or serum concentrations taking into account the bioavailability of the particular compound is well within the capabilities of skilled artisans. For guidance, the reader is referred to Fingl & Woodbury, "General Principles," *In: Goodman and Gilman's The Pharmaceutical Basis of Therapeutics*, latest edition, Pergamon Press, and the references cited therein.

Embodiments of the disclosed calcium channel agonists may be administered by oral, parenteral (for example, intramuscular, intraperitoneal, intravenous, ICV, intracisternal injection or infusion, subcutaneous injection, or implant), by inhalation spray, nasal, vaginal, rectal, sublingual, urethral (for example, urethral suppository) or topical routes of administration (for example, gel, ointment, cream, aerosol, etc.) and may be formulated, alone or together, in suitable dosage unit formulations containing conventional non-toxic pharmaceutically acceptable carriers, adjuvants, excipients and vehicles appropriate for each route of administration. In addition to the treatment of warm-blooded animals such as mice, rats, horses, cattle, sheep, dogs, cats, monkeys, etc., the compounds described herein may be effective in humans.

Pharmaceutical compositions for administration to a subject can include at least one further pharmaceutically acceptable additive such as carriers, thickeners, diluents, buffers, preservatives, surface active agents and the like in addition to the calcium channel agonist. Pharmaceutical compositions can also include one or more additional active ingredients such as antimicrobial agents, anti-inflammatory agents, anesthetics, and the like. The pharmaceutically acceptable carriers useful for these formulations are conventional. *Remington's Pharmaceutical Sciences*, by E. W. Martin, Mack Publishing Co., Easton, Pa., 19th Edition (1995), describes compositions and formulations suitable for pharmaceutical delivery of the compounds disclosed herein.

In general, the nature of the carrier will depend on the particular mode of administration being employed. For instance, parenteral formulations usually contain injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Pharmaceutical compositions disclosed herein include those formed from pharmaceutically acceptable salts and/or solvates of the disclosed calcium channel agonists. Pharmaceutically acceptable salts include those derived from pharmaceutically acceptable inorganic or organic bases and acids. Particular disclosed calcium channel agonists possess at least one basic group that can form acid-base salts with acids. Examples of basic groups include, but are not limited to, amino and imino groups. Examples of inorganic acids that can form salts with such basic groups include, but are not limited to, mineral acids such as hydrochloric acid, hydrobromic acid, sulfuric acid or phosphoric acid. Basic groups also can form salts with organic carboxylic acids, sulfonic acids, sulfo acids or phospho acids or N-substituted sulfamic acid, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and, in addition, with amino acids, for example with α-amino acids, and also with methanesulfonic acid, ethanesulfonic acid, 2-hydroxymethanesulfonic acid, ethane-1,2-disulfonic acid, benzenedisulfonic acid, 4-methylbenzenesulfonic acid, naphthalene-2-sulfonic acid, 2- or 3-phosphoglycerate, glucose-6-phosphate or N-cyclohexylsulfamic acid (with formation of the cyclamates) or with other acidic organic compounds, such as ascorbic acid. In particular, suitable salts include those derived from alkali metals such as potassium and sodium, alkaline earth metals such as calcium and magnesium, among numerous other acids well known in the pharmaceutical art.

Certain calcium channel agonists may include at least one acidic group that can form an acid-base salt with an inorganic or organic base. Examples of salts formed from inorganic bases include salts of the presently disclosed compounds with alkali metals such as potassium and sodium, alkaline earth metals, including calcium and magnesium and the like. Similarly, salts of acidic compounds with an organic base, such as an amine (as used herein terms that refer to amines should be understood to include their conjugate acids unless the context clearly indicates that the free amine is intended) are contemplated, including salts formed with basic amino acids, aliphatic amines, heterocyclic amines, aromatic amines, pyridines, guanidines and amidines. Of the aliphatic amines, the acyclic aliphatic amines, and cyclic and acyclic di- and tri-alkyl amines are particularly suitable for use in the disclosed compounds. In addition, quaternary ammonium counterions also can be used.

Particular examples of suitable amine bases (and their corresponding ammonium ions) for use in the present calcium channel agonists include, without limitation, pyridine, N,N-dimethylaminopyridine, diazabicyclononane, diazabicycloundecene, N-methyl-N-ethylamine, diethylamine, triethylamine, diisopropylethylamine, mono-, bis- or tris-(2-hydroxyethyl)amine, 2-hydroxy-tert-butylamine, tris (hydroxymethyl)methylamine, N,N-dimethyl-N-(2-hydroxyethyl)amine, tri-(2-hydroxyethyl)amine and N-methyl-D-glucamine For additional examples of "pharmacologically acceptable salts," see Berge et al., *J. Pharm. Sci.* 66:1 (1977). The pharmaceutical compositions can be administered to subjects by a variety of mucosal administration modes, including by oral, rectal, intranasal, intrapulmonary, or transdermal delivery, or by topical delivery to other surfaces. Optionally, the compositions can be administered by non-mucosal routes, including by intramuscular, subcutaneous, intravenous, intra-arterial, intra-articular, intraperitoneal, intrathecal, intracerebroventricular, or parenteral routes. In other alternative embodiments, the compound can be administered ex vivo by direct exposure to cells, tissues or organs originating from a subject.

To formulate the pharmaceutical compositions, the calcium channel agonist can be combined with various pharmaceutically acceptable additives, as well as a base or vehicle for dispersion of the compound. Desired additives include, but are not limited to, pH control agents, such as arginine, sodium hydroxide, glycine, hydrochloric acid, citric acid, and the like. In addition, local anesthetics (for example, benzyl alcohol), isotonizing agents (for example, sodium chloride, mannitol, sorbitol), adsorption inhibitors (for example, Tween 80 or Miglyol 812), solubility enhancing agents (for example, cyclodextrins and derivatives thereof), stabilizers (for example, serum albumin), and reducing agents (for example, glutathione) can be included. Adjuvants, such as aluminum hydroxide (for example, Amphogel, Wyeth Laboratories, Madison, N.J.), Freund's adjuvant, MPL™ (3-O-deacylated monophosphoryl lipid A; Corixa, Hamilton, Ind.) and IL-12 (Genetics Institute, Cambridge, Mass.), among many other suitable adjuvants well known in the art, can be included in the compositions. When the composition is a liquid, the tonicity of the formulation, as measured with reference to the tonicity of 0.9% (w/v) physiological saline solution taken as unity, is typically adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

The calcium channel agonist can be dispersed in a base or vehicle, which can include a hydrophilic compound having a capacity to disperse the compound, and any desired additives. The base can be selected from a wide range of suitable compounds, including but not limited to, copolymers of polycarboxylic acids or salts thereof, carboxylic anhydrides (for example, maleic anhydride) with other monomers (for example, methyl (meth)acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof. Often, a biodegradable polymer is selected as a base or vehicle, for example, polylactic acid, poly(lactic acid-glycolic acid) copolymer, polyhydroxybutyric acid, poly(hydroxybutyric acid-glycolic acid) copolymer and mixtures thereof. Alternatively or additionally, synthetic fatty acid esters such as polyglycerin fatty acid esters, sucrose fatty acid esters and the like can be employed as vehicles. Hydrophilic polymers and other vehicles can be used alone or in combination, and enhanced structural integrity can be imparted to the vehicle by partial crystallization, ionic bonding, cross-linking and the like. The vehicle can be provided in a variety of forms, including fluid or viscous solutions, gels, pastes, powders, microspheres and films for direct application to a mucosal surface.

The calcium channel agonist can be combined with the base or vehicle according to a variety of methods, and release of the compound can be by diffusion, disintegration of the vehicle, or associated formation of water channels. In some circumstances, the calcium channel agonist is dispersed in microcapsules (microspheres) or nanocapsules (nanospheres) prepared from a suitable polymer, for example, isobutyl 2-cyanoacrylate (see, for example, Michael et al., *J. Pharmacy Pharmacol.* 43:1-5, 1991), and dispersed in a biocompatible dispersing medium, which yields sustained delivery and biological activity over a protracted time.

The compositions of the disclosure can alternatively contain as pharmaceutically acceptable vehicles substances as required to approximate physiological conditions, such as pH adjusting and buffering agents, tonicity adjusting agents, wetting agents and the like, for example, sodium acetate, sodium lactate, sodium chloride, potassium chloride, calcium chloride, sorbitan monolaurate, and triethanolamine oleate. For solid compositions, conventional nontoxic pharmaceutically acceptable vehicles can be used which include, for example, pharmaceutical grades of mannitol, lactose, starch, magnesium stearate, sodium saccharin, talcum, cellulose, glucose, sucrose, magnesium carbonate, and the like.

Pharmaceutical compositions for administering the calcium channel agonist can also be formulated as a solution, microemulsion, or other ordered structure suitable for high concentration of active ingredients. The vehicle can be a solvent or dispersion medium containing, for example, water, ethanol, polyol (for example, glycerol, propylene glycol, liquid polyethylene glycol, and the like), and suitable mixtures thereof. Proper fluidity for solutions can be maintained, for example, by the use of a coating such as lecithin, by the maintenance of a desired particle size in the case of dispersible formulations, and by the use of surfactants. In many cases, it will be desirable to include isotonic agents, for example, sugars, polyalcohols, such as mannitol and sorbitol, or sodium chloride in the composition. Prolonged absorption of the calcium channel agonist can be brought about by including in the composition an agent which delays absorption, for example, monostearate salts and gelatin.

In certain embodiments, the calcium channel agonist can be administered in a time release formulation, for example in a composition which includes a slow release polymer. These compositions can be prepared with vehicles that will protect against rapid release, for example a controlled release vehicle such as a polymer, microencapsulated delivery system or bioadhesive gel. Prolonged delivery in various compositions of the disclosure can be brought about by including in the composition agents that delay absorption, for example, aluminum monostearate hydrogels and gelatin. When controlled release formulations are desired, controlled release binders suitable for use in accordance with the disclosure include any biocompatible controlled release material which is inert to the active agent and which is capable of incorporating the calcium channel agonist and/or other biologically active agent. Numerous such materials are known in the art. Useful controlled-release binders are materials that are metabolized slowly under physiological conditions following their delivery (for example, at a mucosal surface, or in the presence of bodily fluids). Appropriate binders include, but are not limited to, biocompatible polymers and copolymers well known in the art for use in sustained release formulations. Such biocompatible compounds are non-toxic and inert to surrounding tissues, and do not trigger significant adverse side effects, such as nasal irritation, immune response, inflammation, or the like. They are metabolized into metabolic products that are also biocompatible and easily eliminated from the body.

Exemplary polymeric materials for use in the present disclosure include, but are not limited to, polymeric matrices derived from copolymeric and homopolymeric polyesters having hydrolyzable ester linkages. A number of these are known in the art to be biodegradable and to lead to degradation products having no or low toxicity. Exemplary polymers include polyglycolic acids and polylactic acids, poly (DL-lactic acid-co-glycolic acid), poly(D-lactic acid-co-glycolic acid), and poly(L-lactic acid-co-glycolic acid). Other useful biodegradable or bioerodable polymers include, but are not limited to, such polymers as poly (epsilon-caprolactone), poly(epsilon-caprolactone-CO-lactic acid), poly(epsilon.-caprolactone-CO-glycolic acid), poly(beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. Many methods for preparing such formulations are well known to those skilled in the art (see, for example, *Sustained and Controlled Release Drug Delivery Systems*, J. R. Robinson, ed., Marcel Dekker, Inc., New York, 1978). Other useful formulations include controlled-release microcapsules (U.S. Pat. Nos. 4,652,441 and 4,917,893), lactic acid-glycolic acid copolymers useful in making microcapsules and other formulations (U.S. Pat. Nos. 4,677,191 and 4,728,721) and sustained-release compositions for water-soluble peptides (U.S. Pat. No. 4,675,189).

The pharmaceutical compositions of the disclosure typically are sterile and stable under conditions of manufacture, storage and use. Sterile solutions can be prepared by incorporating the compound in the required amount in an appropriate solvent with one or a combination of ingredients enumerated herein, as required, followed by filtered sterilization. Generally, dispersions are prepared by incorporating the compound and/or other biologically active agent into a sterile vehicle that contains a basic dispersion medium and the required other ingredients from those enumerated herein. In the case of sterile powders, methods of preparation include vacuum drying and freeze-drying which yields a powder of the compound plus any additional desired ingredient from a previously sterile-filtered solution thereof. The prevention of the action of microorganisms can be accomplished by various antibacterial and antifungal agents, for example, parabens, chlorobutanol, phenol, sorbic acid, thimerosal, and the like.

In accordance with the various treatment methods of the disclosure, the calcium channel agonist can be delivered to a subject in a manner consistent with conventional methodologies associated with management of the disorder for which treatment or prevention is sought. In accordance with the disclosure herein, a prophylactically or therapeutically effective amount of the calcium channel agonist is administered to a subject in need of such treatment for a time and under conditions sufficient to inhibit, and/or ameliorate a selected disease or condition or one or more symptom(s) thereof.

The administration of the calcium channel agonist of the disclosure can be for either prophylactic or therapeutic purpose. When provided prophylactically, the calcium channel agonist is provided in advance of any symptom. The prophylactic administration of the calcium channel agonist serves to inhibit or ameliorate any subsequent disease process. When provided therapeutically, the calcium channel agonist is provided at (or shortly after) the onset of a symptom of disease.

For prophylactic and therapeutic purposes, the calcium channel agonist can be administered to the subject by the oral route or in a single bolus delivery, via continuous delivery (for example, continuous transdermal, mucosal or intravenous delivery) over an extended time period, or in a repeated administration protocol (for example, by an hourly, daily or weekly, repeated administration protocol). The therapeutically effective dosage of the calcium channel agonist can be provided as repeated doses within a prolonged prophylaxis or treatment regimen that will yield clinically significant results to alleviate one or more symptoms or detectable conditions associated with a targeted disease or condition as set forth herein. Determination of effective dosages in this context is typically based on animal model studies followed up by human clinical trials and is guided by administration protocols that significantly reduce the occurrence or severity of targeted disease symptoms or conditions in the subject. Suitable models in this regard include, for example, murine, rat, avian, porcine, feline, non-human primate, and other accepted animal model subjects known in the art. Alternatively, effective dosages can be determined using in vitro models. Using such models, only ordinary calculations and adjustments are required to determine an appropriate concentration and dose to administer a therapeutically effective amount of the calcium channel agonist (for example, amounts that are effective to elicit a desired increase in calcium channel activity or alleviate one or more symptoms of a targeted disease).

The actual dosage of the calcium channel agonist will vary according to factors such as the disease indication and particular status of the subject (for example, the subject's age, size, fitness, extent of symptoms, susceptibility factors, and the like), time and route of administration, other drugs or treatments being administered concurrently, as well as the specific pharmacology of the compound for eliciting the desired activity or biological response in the subject. Dosage regimens can be adjusted to provide an optimum therapeutic response. A therapeutically effective amount is also one in which any toxic or detrimental side effects of the compound and/or other biologically active agent is outweighed in clinical terms by therapeutically beneficial effects. A non-limiting range for a therapeutically effective amount of a compound and/or other biologically active agent within the methods and formulations of the disclosure is about 0.01 mg/kg body weight to about 20 mg/kg body weight, such as about 0.05 mg/kg to about 5 mg/kg body weight, or about 0.2 mg/kg to about 2 mg/kg body weight.

Dosage can be varied by the attending clinician to maintain a desired concentration at a target site (for example, the lungs or systemic circulation). Higher or lower concentrations can be selected based on the mode of delivery, for example, trans-epidermal, rectal, oral, pulmonary, or intranasal delivery versus intravenous or subcutaneous delivery. Dosage can also be adjusted based on the release rate of the administered formulation, for example, of an intrapulmonary spray versus powder, sustained release oral versus injected particulate or transdermal delivery formulations, and so forth.

The calcium channel agonists disclosed herein may be co-administered with an additional therapeutic agent. Such agents include, but are not limited to, acetylcholinesterase inhibitors, immunosuppressants, intravenous immunoglobulins, glucocorticoids, ascorbic acid, anti-cancer agents (e.g., if the calcium channel dysfunction is caused by underlying malignancy), potassium channel blockers, copper supplementation (if the calcium channel dysfunction is caused by copper deficiency), analgesics, antidepressants, muscle relaxants, and combinations thereof. The calcium channel agonist also may be co-administered with adjunct therapies, such as plasmapheresis, ventilator assistance (e.g., for Guillain-Barré syndrome or amyotrophic lateral sclerosis), braces, physical therapy, occupational therapy, or combinations thereof. Co-administration may be performed simultaneous or sequentially.

In certain embodiments, when the condition to be treated is LEMS, the calcium channel agonist may be co-administered with a therapeutically effective amount of 3,4-diaminopyridine (DAP, a potassium channel blocker). In combination, a calcium channel agonist according to general formula I and DAP may exert synergistic effects on transmitter release when both are applied at concentrations that are lower than what is required for effects when given alone, thereby lowering the therapeutically effective amount of one or both compounds. Because DAP broadens the presynaptic action potential, calcium channels will open for a longer period of time during the action potential, and the open channel binding of the calcium channel agonist would be expected to occur more frequently. Therefore, DAP administered in combination with an embodiment of the disclosed calcium channel agonists may result in a stronger effect that provides an even greater reversal of neuromuscular weakness.

The instant disclosure also includes kits, packages and multi-container units containing the herein described pharmaceutical compositions, active ingredients, and/or means for administering the same for use in the prevention and treatment of diseases and other conditions in mammalian subjects. The calcium channel agonist may be formulated in a pharmaceutical preparation for delivery to a subject. The calcium channel agonist is optionally contained in a bulk dispensing container or unit or multi-unit dosage form. Optional dispensing means can be provided, for example a pulmonary or intranasal spray applicator. Packaging materials optionally include a label or instruction indicating for what treatment purposes and/or in what manner the pharmaceutical agent packaged therewith can be used.

B. An Experimental Tool for Studying $Ca^{2+}$ Channel Subtypes

Historically, calcium channel gating modifiers have been valuable experimental tools. Because voltage-gated calcium channels have a relatively small conductance and brief mean open time, single channel gating has been relatively difficult to study in detail. Further, studies of physiological effects of calcium channels can be aided by the use of gating modifiers. Relatively few calcium channel agonists have been identified (the most well-known among them is BayK 8644), and those that have been developed only bind selectively to L-type calcium channels. These L-type agonists have provided an experimental opportunity to increase mean open time for L-type calcium channels. With this tool, investigators have been better able to determine conductance in physiological calcium concentrations, test for a role of L-type channels in the regulation of transmitter release at synapses, study the structural motifs within the L-type calcium channel that regulate gating, study the influence of ion permeation on gating, and examine cell signaling that employs L-type calcium channels, among many other experimental uses.

Independent of its therapeutic potential for treatment of diseases characterized by neuromuscular weakness, a selective and potent $Ca^{2+}$ channel agonist of the P/Q- and N-type $Ca^{2+}$ channels would serve as an important experimental tool for studying the basic properties of these $Ca^{2+}$ channel subtypes. Just as the L-type $Ca^{2+}$ channel agonists BayK 8644 and FPL64176 were important in studies of L-type channel gating, conductance, and kinetics, an agonist of the P/Q- and N-type channels would be equally as useful in the study of their properties. Furthermore, embodiments of the disclosed compounds may serve as a useful probe molecule in studies of the calcium control of chemical transmitter release. Even though (R)-roscovitine is an agonist of the P/Q-and N-type channel subtypes, certain embodiments of the disclosed calcium channel agonists (e.g., compound 13x) are more selective and potent than (R)-roscovitine, and thus likely to be more useful for studies on basic P/Q- and N-type $Ca^{2+}$ channel function.

V. Examples

General Information:

All moisture and air-sensitive reactions were performed using syringe-septum cap techniques under an inert atmosphere ($N_2$ or Ar) in glassware that was dried in an oven at 140° C. for at least 2 h prior to use. Reactions carried out at a temperature below 0° C. employed a $CO_2$/acetone bath. All reagents and solvents were used as received unless otherwise specified. Triethylamine, N,N-dimethylaniline and pyridine were distilled over $CaH_2$. THF and $Et_2O$ were distilled over sodium/benzophenone ketyl. Dichloromethane and toluene were purified using an alumina column filtration system. Anhydrous MeOH and $Et_2O$ were purchased from Acros Organics and Fisher Scientific, respectively. Anhydrous DMF was purchased from Acros Organics or distilled and stored over 4 A molecular sieves. Analytical thin-layer chromatography (TLC) was performed on pre-coated $SiO_2$ 60 F254 plates (250 μm layer thickness) available from Merck. Visualization was accomplished by UV irradiation at 254 nm and/or by staining with Vaughn's reagent (4.8 g $(NH_4)_6Mo_7O_{24}\cdot4H_2O$ and 0.2 g $Ce(SO_4)_2\cdot4H_2O$ in 100 mL of a 3.5 N $H_2SO_4$ solution), a $KMnO_4$ solution (1.5 g $KMnO_4$ and 1.5 g $K_2CO_3$ in 100 mL of a 0.1% NaOH solution), a ninhydrin solution (2 g ninhydrin in 100 mL of ethanol (EtOH)), a PMA solution (5 g of phosphomolybdic acid in 100 mL of EtOH), or a p-anisaldehyde solution (2.5 mL of p-anisaldehyde, 2 mL of acetic acid and 3.5 mL of conc. aq. $H_2SO_4$ in 100 mL of EtOH). Preparative thin-layer chromatography was performed on pre-coated $SiO_2$ GF ($UV_{254}$) 1000 microns (20×20 cm) plates available from Analtech. Flash column chromatography was performed using $SiO_2$ 60 (particle size 0.040-0.055 mm, 230-400 mesh, or Silicycle SiliaFlash® P60, 40-63 μm). Melting points were determined on a Meltemp capillary melting point apparatus fitted with a Fluke 51 II digital thermometer. Infrared spectra were recorded on a Smiths IdentifyIR ATR spectrometer or a Perkin Elmer Spectrum 100 FT-IR spectrometer using the Universal ATR Sampling Accessory for both oil and solid compounds. $^1$H NMR and $^{13}$C NMR spectra were obtained on Bruker Avance 300, 400 or 600 instruments at 300/75 MHz, 400/100 MHz or 600/150 MHz, respectively. Chemical shifts were reported in parts per million (ppm) as referenced to residual solvent. $^1$H NMR spectra were tabulated as follows: chemical shift, multiplicity (app=apparent, b=broad, s=singlet, d=doublet, t=triplet, q=quartet, quint=quintuplet, sext=sextuplet, sept=septuplet, m=multiplet), number of protons, coupling constant(s). $^{13}$C NMR spectra were obtained using a proton-decoupled pulse sequence. Mass spectra were obtained on a Waters Autospec double focusing mass spectrometer (EI) or a Waters Q-Tof mass spectrometer (ESI).

Compound Synthesis and Characterization:

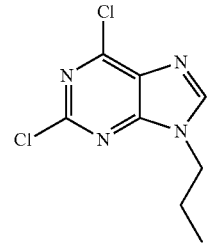

15a 2,6-Dichloro-9-propyl-9H-purine (15a). To a solution of 2,6-dichloro-9H-purine 14 (0.490 mg, 2.59 mmol) in anhydrous DMSO (3.0 mL) was added $K_2CO_3$ (1.10 g, 7.96 mmol) followed by 1-bromopropane (1.62 g, 13.1 mmol) at 16-18° C. (isopropanol (i-PrOH) bath in a Dewar flask covered with aluminum foil). The reaction mixture was stirred at 16-18° C. for 17 h, quenched with water and extracted with ethyl acetate (EtOAc). The combined organic layers were washed with brine, dried (MgSO4), concentrated, and purified by chromatography on SiO2 (hexanes, 100%, to hexanes/EtOAc, 1:1) to yield 15a (0.465 g, 2.01 mmol, 78% yield) as an off-white solid: IR (ATR, neat) 3677, 3078, 2974, 2939, 2880, 1596, 1553, 1496, 1466, 1442, 1408, 1383, 1370, 1347, 1312, 1270, 1229, 1196, 1180, 1141, 1084, 957, 901, 875, 860, 812, 785, 774, 681 $cm^{-1}$; $^1$ H NMR (600 MHz, $CDCl_3$) δ 8.10 (s, 1 H), 4.21 (t, 2 H, J=7.2 Hz), 1.93 (sext, 2 H, J=7.4 Hz), 0.94 (t, 3 H, J=7.5 Hz); $^{13}$C NMR (151 MHz, $CDCl_3$) δ 153.2, 152.7, 151.5, 146.0, 46.2, 23.1, 11.1.

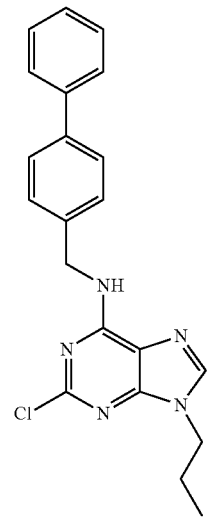

16a

N-(Biphenyl-4-ylmethyl)-2-chloro-9-propyl-9H-purin-6-amine (16a). To a solution of 15a (58.0 mg, 0.251 mmol) in n-butanol (n-BuOH) (1.0 mL) were added 4-phenylbenzylamine (52.0 mg, 0.267 mmol) and triethylamine (40.6 mg, 0.402 mmol) under an $N_2$ atmosphere at room temperature. The reaction mixture was heated in a microwave at 120° C. for 20 min. The solvent was evaporated, and the crude residue was dissolved in EtOAc and washed with water. The aqueous phase was further extracted with EtOAc, and the combined organic extracts were dried (MgSO$_4$) and concentrated to yield a colorless solid, which was resuspended (hexanes/Et$_2$O, 3:1), filtered, triturated (hexanes/Et$_2$O, 3:1) and dried under high-vacuum to yield 16a (86.2 mg, 0.228 mmol, 91% yield) as a colorless solid: IR (ATR, neat) 3145, 2964, 1619, 1577, 1304, 1254 cm$^{-1}$; $^1$H NMR (600 MHz, CDCl$_3$) δ 7.56 (d, 2 H, J=8.4 Hz), 7.56 (d, 2 H, J=7.8 Hz), 7.47-7.40 (m, 5 H), 7.35 (t, 1 H, J=7.5 Hz), 6.88 (bm, 1 H), 4.87 (bs, 2 H), 4.05 (t, 2 H, J=6.6 Hz), 1.85 (sext, 2 H, J=7.4 Hz), 0.91 (t, 3 H, J=6.9 Hz); $^{13}$C NMR (151 MHz, CDCl$_3$) δ 155.3, 154.7, 150.4, 140.7, 140.4, 137.2, 128.9, 128.6, 127.5 (2 C), 127.2, 118.8, 45.6, 44.5, 23.4, 11.2.

128.1, 127.2, 127.0, 114.3, 68.2, 56.2, 45.0, 44.0, 25.0, 23.1, 11.2, 10.9; HRMS (ES$^+$) m/z calcd for $C_{25}H_{31}N_6O$ [M+H]$^+$ 431.2559, found 431.2532.

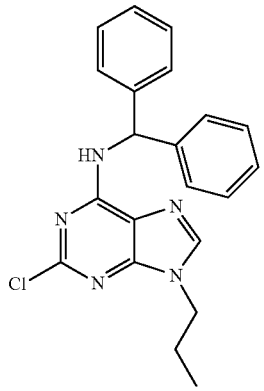

16b

2-Chloro-N-(2,2-diphenylethyl)-9-propyl-9H-purin-6-amine (16b). To a solution of 15a (71.0 mg, 0.307 mmol) in n-BuOH (1.0 mL) was added aminodiphenylmethane (61.5 mg, 0.326 mmol) and triethylamine (50.1 mg, 0.495 mmol) under an $N_2$ atmosphere. The reaction mixture was heated in a microwave reactor at 120° C. for 20 min. The solvent was evaporated, and the residue was dissolved in EtOAc and washed with water. The aqueous phase was further extracted with EtOAc, and the combined organic extracts were dried (MgSO$_4$) and concentrated to yield a colorless solid, which was resuspended (hexanes/Et$_2$O, 3:1), filtered, and triturated (hexanes/Et$_2$O, 3:1) to obtain an off-white solid. The filtrate was concentrated, resuspended (hexanes/Et$_2$O, 3:1), and filtered to obtain additional product. After drying on high-vacuum, 16b (74.4 mg, 0.197 mmol, 65%) was obtained as an off-white solid: IR (ATR, neat) 3250, 2964, 1612, 1574, 1304, 1218 cm$^{-1}$; $^1$H NMR (600 MHz, CDCl$_3$) δ 7.54 (bs, 1 H), 7.35-7.20 (m, 9 H), 7.17 (s, 1 H), 6.78 (d, 1 H, J=6.6 Hz), 4.09-3.90 (bm, 2 H), 1.95-1.69 (bm, 2 H), 0.90 (t, 3 H, J=6.9 Hz); $^{13}$C NMR (151 MHz, CDCl$_3$) δ 154.4, 154.2, 150.3, 141.3, 140.4, 127.7, 127.5, 127.3, 118.5, 57.1, 45.4, 23.2, 11.0; LCMS (ES$^+$) m/z calcd for $C_{21}H_{21}N_5Cl$ [M+H]$^+$ 378.1, found 378.1.

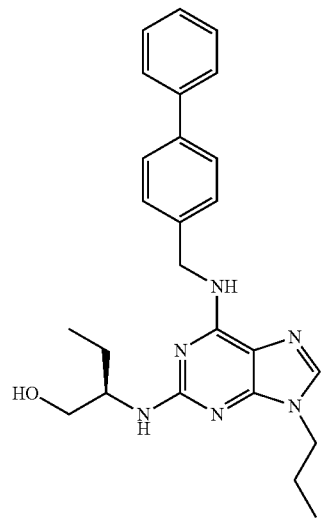

13a (R)-2-(6-(Biphenyl-4-ylmethylamino)-9-propyl-9H-purin-2-ylamino)butan-1-ol (13a). A mixture of 16a (50.0 mg, 0.128 mmol) and (R)-(−)-2-amino-1-butanol (60.9 mg, 0.642 mmol) was heated in a microwave vial immersed in an oil bath at 170° C. for 8 h. The reaction mixture was cooled to room temperature, diluted with water, and extracted with EtOAc (4×). The combined organic layers were washed with warmed water (50-55° C., 2×), dried (MgSO$_4$), concentrated, and dried under high vacuum at 50° C. (oil bath) for 2 h to yield a yellow solid. Upon the addition of Et$_2$O to the yellow solid, an off-white solid precipitated. The solid was further washed with Et$_2$O (3×) and dried under high-vacuum at 40° C. overnight to yield 13a (32.6 mg, 0.0757 mmol, 59%) as an off-white solid: Mp 130-131° C.; IR (ATR, neat) 3270, 2962, 2931, 1599, 1488, 1349 cm$^{-1}$; $^1$H NMR (600 MHz, CDCl$_3$) δ 7.57 (app d, 2 H, J=7.8 Hz), 7.54 (app d, 2 H, J=7.8 Hz), 7.47-7.38 (m, 4 H), 7.37-7.28 (m, 2 H), 6.46 (bs, 1 H), 5.26-5.08 (bm, 1 H), 4.97 (s, 1 H), 4.91-4.66 (bm, 2 H), 3.92 (t, 2 H, J=6.9 Hz), 3.90-3.85 (bm, 1 H), 3.81 (bd, 1 H, J=12.0 Hz), 3.63 (app t, 1 H, J=9.0 Hz), 1.82 (sext, 2 H, J=7.2 Hz), 1.67-1.49 (m, 2 H), 1.00 (t, 3 H, J=7.2 Hz), 0.91 (t, 3 H, J=7.2 Hz); $^{13}$C NMR (151 MHz, CDCl$_3$) δ 160.2, 154.9, 150.7, 140.7, 140.2, 137.9, 137.1, 128.7,

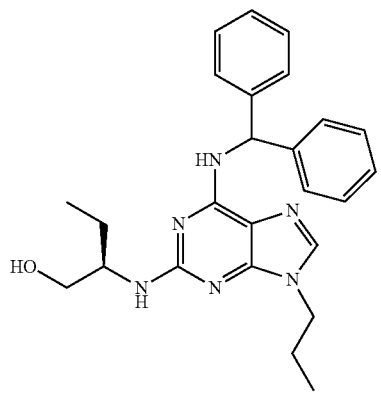

13b (R)-2-(6-(2,2-Diphenylethylamino)-9-propyl-9H-purin-2-ylamino)butan-1-ol (13b). A mixture of 16b (50.0 mg, 0.128 mmol) and (R)-(−)-2-amino-1-butanol (60.9 mg, 0.642 mmol) were heated in a vial immersed in an oil bath at 170° C. for 8 h. The reaction mixture was cooled to room temperature, diluted with water, and extracted with EtOAc (4×). The combined organic phases were washed with warm water (50-55° C., 2×), dried (MgSO$_4$), concentrated, and dried under high-vacuum at 50° C. (oil bath) for 2 h to yield a solid-yellow oil. Upon addition of Et$_2$O, an off-white solid precipitated. The solid was rinsed with Et$_2$O (3×) and dried under high-vacuum at 40° C. to yield 13b (36.9 mg, 0.0857 mmol, 67%) as an off-white solid: Mp 160-163° C.; IR (ATR, neat) 3269, 2960, 1606, 1556, 1439 cm$^{-1}$; $^1$H NMR (600 MHz, CDCl$_3$) δ 7.40-7.26 (m, 8 H), 7.25-7.16 (m, 2 H), 6.64-6.29 (m, 2 H), 4.80 (d, 1 H, J=4.8 Hz), 3.89 (t, 2 H, J=6.9 Hz), 3.79-3.69 (bm, 1 H), 3.69-3.61 (bm, 1 H), 3.55-3.41 (bm, 1 H), 1.79 (sext, 2 H, J=6.6 Hz), 1.61-1.37 (m, 2 H), 1.05-0.90 (m, 6 H); $^{13}$C NMR (151 MHz, CDCl$_3$) δ 160.0, 153.9, 142.2, 137.2, 128.5 (2 C), 127.6, 127.2 (2 C), 114.3, 67.7, 57.9, 56.0, 45.0, 24.8, 23.1, 11.2, 10.8; HRMS (ES$^+$) m/z calcd for C$_{25}$H$_{31}$N$_6$O [M+H]$^+$ 431.2559, found 431.2596.

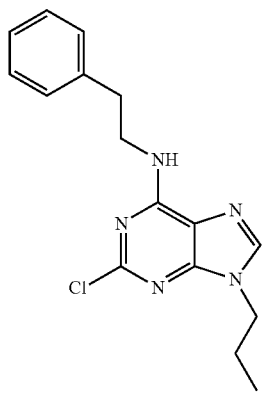

16c

2-Chloro-N-phenethyl-9-propyl-9H-purin-6-amine (16c). To a solution of 15a (58.0 mg, 0.251 mmol) in n-BuOH (1.0 mL) was added phenethylamine (32.8 mg, 0.269 mmol) and triethylamine (40.6 mg, 0.402 mmol) under an N$_2$ atmosphere. The reaction mixture was heated under microwave irradiation at 120° C. for 30 min. n-BuOH was evaporated and the residue was dissolved in EtOAc and washed with water. The aqueous phase was further extracted with EtOAc and the combined organic layers were dried (MgSO$_4$) and concentrated to yield a colorless solid, which was resuspended (hexanes/Et$_2$O, 3:1, filtered, triturated (hexanes/Et$_2$O, 3:1) and dried under high-vacuum to yield 16c (67.0 mg, 0.212 mmol, 85%) as an amorphous off-white solid: IR (ATR, neat) 3218, 2960, 1620, 1576, 1355, 1307, 1232 cm$^{-1}$; $^1$H NMR (600 MHz, CDCl$_3$) δ 7.47-7.30 (m, 1 H), 7.25-7.19 (m, 2 H), 7.19-7.09 (m, 3 H), 6.91-6.63 (m, 1 H), 4.15-3.98 (bm, 2 H), 3.95-3.67 (bm, 2 H), 3.00-2.87 (bm, 2 H), 1.98-1.78 (bm, 2 H), 0.92 (bt, 3 H, J=6.3 Hz); $^{13}$C NMR (151 MHz, CDCl$_3$) δ 155.1, 154.4, 149.9, 139.8, 138.8, 128.7, 128.4, 126.2, 118.5, 45.3, 41.8, 35.4, 23.2, 11.0.

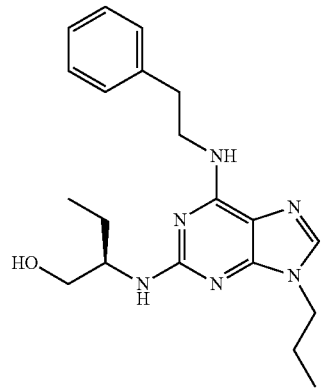

13c (R)-2-(6-(Phenethylamino)-9-propyl-9H-purin-2-ylamino)butan-1-ol (13c). A mixture of 16c (50.0 mg, 0.158 mmol) and (R)-(−)-2-amino-1-butanol (76.0 mg, 0.801 mmol) was heated in a microwave vial immersed in an oil bath at 170° C. for 7 h. The reaction mixture was cooled to room temperature, diluted with water, and extracted with EtOAc (3×). The combined organic phases were washed with warm water (50-55° C., 2×), dried (MgSO$_4$), concentrated, and dried under high-vacuum at 50° C. (oil bath) for 2 h to yield an oily yellow residue. Upon the addition of Et$_2$O and a few drops of hexanes, an off-colorless solid precipitated. The solid was rinsed (Et$_2$O, 3×) by pipetting out the supernatant, and the solid was dried under high-vacuum at 40° C. overnight to yield 13c (18.7 mg, 0.0508 mmol, 32%) as an off-white solid: Mp 105-107° C.; IR (ATR, neat) 3276, 2956, 2929, 1603, 1520 cm$^{-1}$; $^1$H NMR (600 MHz, CDCl$_3$) δ 7.43 (bs, 1 H), 7.40-7.32 (m, 2 H), 7.32-7.22 (m, 3 H), 5.80 (bs, 1 H), 5.40 (bs, 1 H), 5.04-4.84 (bm, 1 H), 3.99 (t, 2 H, J=6.6 Hz), 3.97-3.91 (bm, 1 H), 3.91-3.75 (bm, 3 H), 3.69 (t, 1 H, J=9.0 Hz), 2.99 (t, 2 H, J=6.3 Hz), 1.89 (sext, 2 H, J=6.6 Hz), 1.75-1.55 (m, 2 H), 1.08 (t, 3 H, J=7.2 Hz), 0.98 (t, 3 H, J=7.2 Hz); $^{13}$C NMR (151 MHz, CDCl$_3$) δ 160.2, 154.9, 139.0, 137.0, 128.8, 128.6, 126.4, 114.4, 68.6, 56.4, 45.0, 41.7, 35.9, 25.0, 23.2, 11.2, 10.9; HRMS (ES$^+$) m/z calcd for C$_{20}$H$_{29}$N$_6$O [M+H]$^+$ 369.2403, found 369.2422.

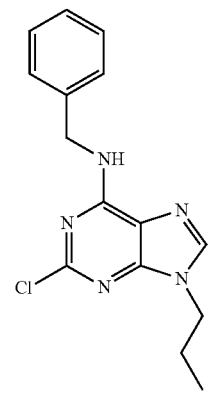

16d

N-Benzyl-2-chloro-9-propyl-9H-purin-6-amine (16d). To a solution of 15a (63.0 mg, 0.273 mmol) in n-BuOH (1.0 mL) was added benzylamine (31.4 mg, 0.287 mmol) and triethylamine (43.6 mg, 0.430 mmol) under an N$_2$ atmosphere. The reaction mixture was heated under microwave irradiation at 120° C. for 30 min. n-BuOH was evaporated, and the residue was dissolved in EtOAc and washed with water. The aqueous phase was further extracted with EtOAc and the combined organic extracts were dried (MgSO$_4$) and concentrated to yield a colorless solid, which was resuspended (hexanes/Et$_2$O, 3:1), filtered, triturated (hexanes/Et$_2$O, 3:1), and dried under high-vacuum to yield 16d (66.3 mg, 0.220 mmol, 81%) as a colorless solid: IR (ATR, neat) 3189, 2966, 1623, 1304, 1253 cm$^{-1}$; $^1$H NMR (600 MHz, CDCl$_3$) δ 7.44-7.27 (m, 6 H), 7.10-6.75 (bm, 1 H), 4.82 (bs, 2 H), 4.20-4.00 (bm, 2 H), 1.95-1.80 (bm, 2 H), 0.93 (t, 3 H, J=6.6 Hz); $^{13}$C NMR (151 MHz, CDCl$_3$) δ 155.1, 154.5, 150.2, 140.2, 138.0, 128.6, 127.9, 127.5, 118.6, 45.4, 44.6, 23.3, 11.1.

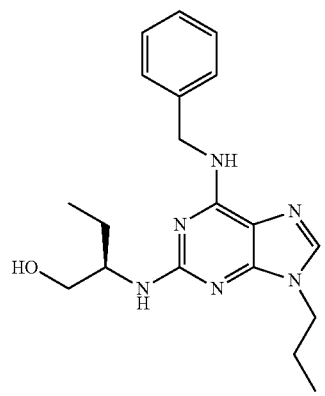

13d (R)-2-(6-(Benzylamino)-9-propyl-9H-purin-2-ylamino)butan-1-ol (13d). A mixture of 16d (50.0 mg, 0.166 mmol) and (R)-(−)-2-amino-1-butanol (78.9 mg, 0.831 mmol) was heated in a microwave vial immersed in an oil bath at 170° C. for 7 h. The reaction mixture was cooled to room temperature, diluted with water, and extracted with EtOAc (3×). The combined organic phases were washed with warm water (50-55° C., 2×) dried (MgSO$_4$), concentrated, and dried under high-vacuum at 50° C. (oil bath) for 2 h to yield a yellow solid. Upon the addition of Et$_2$O to the yellow solid, an off-white solid precipitated. The solid was rinsed (Et$_2$O, 3×) by pipetting out the supernatant and dried under high-vacuum at 40° C. overnight to yield 13d (38.6 mg, 0.109 mmol, 66%) as an off-white solid: Mp 153-155° C.; IR (ATR, neat) 3262, 3201, 2961, 1624, 1603, 1513 cm$^{-1}$; $^1$H NMR (CDCl$_3$, 600 MHz) δ 7.23-7.40 (m, 6 H), 6.22 (bs, 1 H), 5.19 (bs, 1 H), 4.88-4.96 (m, 1 H), 4.75 (bs, 2 H), 3.92-3.97 (m, 2 H), 3.85-3.92 (m, 1 H), 3.81 (d, 1 H, J=10.8 Hz), 3.62 (t, 1 H, J=8.7 Hz), 1.90-1.80 (m, 2 H), 1.70-1.50 (m, 2 H), 1.02 (t, 3 H, J=7.2 Hz), 0.94 (t, 3 H, J=6.6 Hz); $^{13}$C NMR (CDCl$_3$, 150 MHz) δ 160.2, 154.8, 150.6, 138.7, 137.1, 128.5, 127.7, 127.3, 114.3, 68.4, 56.3, 45.0, 44.4, 25.0, 23.2, 11.2, 10.9; HRMS (ES) m/z calcd for C$_{19}$H$_{26}$N$_6$O [M+H] 355.2246, found 355.2241.

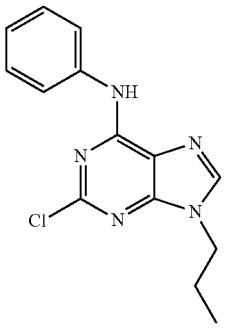

16e

2-Chloro-N-phenyl-9-propyl-9H-purin-6-amine (16e). To a solution of 15a (72.0 mg, 0.312 mmol) in n-BuOH (1.0 mL) were added aniline (30.2 mg, 0.324 mmol) and triethylamine (50.1 mg, 0.495 mmol) under an N$_2$ atmosphere. The reaction mixture was heated under microwave irradiation at 120° C. for 30 min n-BuOH was evaporated, and the residue was dissolved in EtOAc and washed with water. The aqueous phase was further extracted with EtOAc, and the combined organic extracts were dried (MgSO$_4$) and concentrated to yield a colorless solid. The solid was resuspended (hexanes/Et$_2$O, 3:1), filtered, triturated (hexanes/Et$_2$O, 3:1), and dried under high-vacuum to yield 16e (52.7 mg, 0.183 mmol, 59%) as an off-white amorphous solid: IR (ATR, neat) 3179, 2967, 1611, 1572, 1346, 1301 cm$^{-1}$; $^1$H NMR (CDCl$_3$, 600 MHz) δ 8.31 (bs, 1 H), 7.67-7.81 (m, 3 H), 7.36 (t, 2 H, J=7.8 Hz), 7.12 (t, 1 H, J=7.2 Hz), 4.11 (t, 2 H, J=7.2 Hz), 1.89 (sext, 2 H, J=7.2 Hz), 0.94 (t, 3 H, J=7.2 Hz); $^{13}$C NMR (CDCl$_3$, 150 MHz) δ 153.9, 152.3, 150.7, 141.0, 138.0, 128.9, 123.9, 120.3, 119.1, 45.5, 23.2, 11.0.

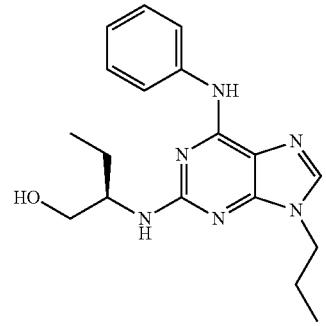

13e (R)-2-(6-(Phenylamino)-9-propyl-9H-purin-2-ylamino)butan-1-ol (13e). A mixture of 16e (41.0 mg, 0.142 mmol) and (R)-(−)-2-amino-1-butanol (68.4 mg, 0.721 mmol) was heated in a microwave vial immersed in an oil bath at 170° C. for 12 h. The reaction mixture was cooled to room temperature, diluted with water, and extracted with EtOAc (3×). The combined organic phases were washed with warm water (50-55° C., 2×), dried (MgSO$_4$), concentrated, and dried under high-vacuum to yield a light-green solid. The crude solid was adsorbed onto SiO$_2$ and purified by chromatography on SiO$_2$ (hexanes/EtOAc, 1:1 to EtOAc, 100% with 1% Et$_3$N to 10% MeOH in EtOAc with 1% Et$_3$N) to yield 13e (23.6 mg, 0.0693 mmol, 49%) as an off-white solid: Mp 190-194° C.; IR (ATR, neat) 3338, 2970, 1644, 1583, 1498, 1474, 1442 cm$^{-1}$; $^1$H NMR (CDCl$_3$, 600 MHz) δ 7.75 (d, 2 H, J=7.8 Hz), 7.65 (bs, 1 H), 7.51 (s, 1 H), 7.35

(t, 2 H, J=7.8 Hz), 7.08 (t, 1 H, J=7.8 Hz), 5.03 (d, 1 H, J=6.6 Hz), 3.93-4.02 (m, 3 H), 3.87 (dd, 1 H, J=10.8, 1.8 Hz), 3.68 (dd, 1 H, J=10.8, 7.2 Hz), 1.87 (sext, 2 H, J=7.2 Hz), 1.57-1.73 (m, 2 H), 1.05 (t, 3 H, J=7.2 Hz), 0.96 (t, 3 H, J=7.2 Hz); $^{13}$C NMR δ (CDCl$_3$, 150 MHz) δ 159.9, 152.4, 150.9, 139.0, 137.6, 128.9, 123.0, 120.0, 114.8, 56.1, 45.1, 29.7, 25.0, 23.2, 11.2, 10.9; HRMS (EI) m/z calcd for C$_{18}$H$_{24}$N$_6$O 340.2012, found 340.2009.

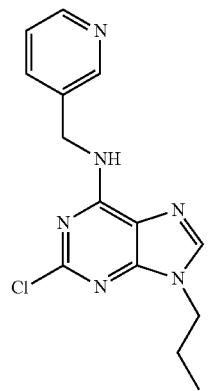

16f

2-Chloro-9-propyl-N-(pyridin-3-ylmethyl)-9H-purin-6-amine (16f). To a solution of 15a (58.0 mg, 0.251 mmol) in n-BuOH (1.0 mL) were added 3-(aminomethyl)-pyridine (28.6 mg, 0.265 mmol) and triethylamine (40.6 mg, 0.402 mmol) under an N$_2$ atmosphere. The reaction mixture was heated under microwave irradiation at 120° C. for 30 min. n-BuOH was evaporated, and the residue was dissolved in EtOAc and washed with water. The aqueous phase was further extracted with EtOAc, and the combined organic extracts were dried (MgSO$_4$) and concentrated to yield a colorless solid. The solid was resuspended (hexanes/Et$_2$O, 3:1), filtered, triturated (hexanes/Et$_2$O, 3:1), and dried under high-vacuum to yield 16f (53.9 mg, 0.178 mmol, 71%) as a yellow amorphous solid: IR (ATR, neat) 3155, 2964, 1626, 1572, 1308, 1232 cm$^{-1}$; $^1$H NMR (CDCl$_3$, 600 MHz) δ 8.57 (s, 1 H), 8.52-8.44 (m, 1 H), 7.64 (d, 1 H, J=7.8 Hz), 7.50 (bs, 1 H), 7.33 (s, 1 H), 7.18 (dd, 1 H, J=7.2, 4.8 Hz), 4.79 (bs, 2 H), 4.05 (t, 2 H, J=7.2 Hz), 1.83 (sext, 2 H, J=7.2 Hz), 0.89 (t, 3 H, J=7.2 Hz); $^{13}$C NMR (CDCl$_3$, 150 MHz) δ 154.9, 154.3, 151.0, 149.2, 148.8, 140.2, 135.5, 133.7, 123.4, 118.5, 45.4, 41.8, 23.2, 11.0.

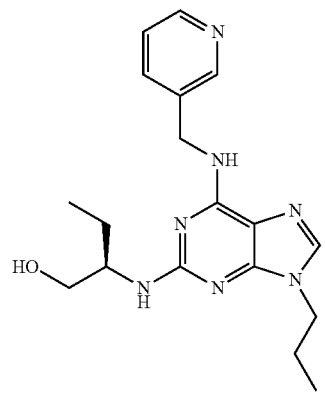

13f (R)-2-(9-Propyl-6-(pyridin-3-ylmethylamino)-9H-purin-2-ylamino)butan-1-ol (13f). A mixture of 16f (35.0 mg, 0.116 mmol) and (R)-(−)-2-amino-1-butanol (55.1 mg, 0.581 mmol) was heated in a microwave vial immersed in an oil bath at 170° C. for 12 h. The reaction mixture was cooled to room temperature, diluted with water, and extracted with EtOAc (3×). The combined organic phases were washed with warm water (50-55° C., 2×), dried (MgSO$_4$), concentrated, and dried under high-vacuum to yield an oily yellow residue. Upon the addition of Et$_2$O and hexanes (drops), a sticky, yellow solid precipitated. The solid was carefully crushed with a glass rod to yield an off-white solid, which was rinsed with Et$_2$O (3×) by pipetting out the supernatant and dried under high-vacuum overnight to yield 13f (27.0 mg, 0.0760 mmol, 66%) as an off-white solid: Mp 129-132° C.; IR (ATR, neat) 3257, 3209, 2964, 1601, 1530, 1477 cm$^{-1}$; $^1$H NMR (CDCl$_3$, 600 MHz) δ 8.68 (s, 1 H), 8.54 (d, 1 H, J=4.8 Hz), 7.73 (d, 1 H, J=7.8 Hz), 7.46 (s, 1 H), 7.30-7.28 (m, 1 H), 5.99 (bs, 1 H), 4.89-4.86 (m, 1 H), 4.81 (bs, 2 H), 4.00 (t, 2 H, J=7.2 Hz), 3.92-3.86 (m, 1 H), 3.81 (d, 1 H, J=10.2 Hz), 3.63 (dd, 1 H, J=10.2, 7.8 Hz), 1.89 (sext, 2 H, J=7.2 Hz), 1.73-1.63 (m, 2 H), 1.63-1.53 (m, 1 H), 1.04 (t, 3 H, J=7.2 Hz), 0.97 (t, 3 H, J=7.2 Hz); $^{13}$C NMR (CDCl$_3$, 150 MHz) δ 160.1, 154.7, 150.9, 149.3, 148.6, 137.3, 135.3, 134.5, 123.4, 114.3, 67.9, 56.1, 45.1, 41.8, 24.9, 23.1, 11.2, 10.9; HRMS (EI) m/z calcd for C$_{18}$H$_{25}$N$_7$O 355.2121, found 355.2124.

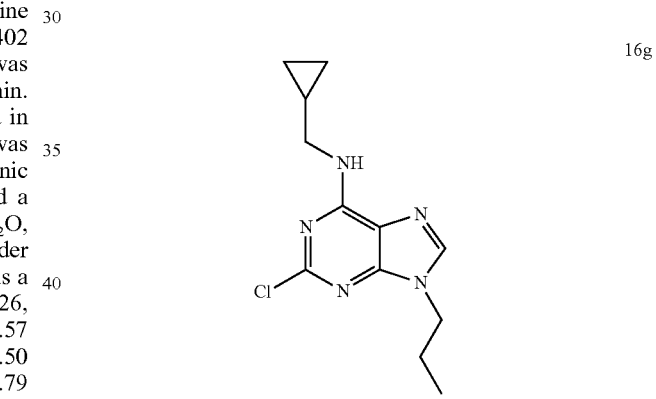

16g

2-Chloro-N-(cyclopropylmethyl)-9-propyl-9H-purin-6-amine (16g). To a solution of 15a (80.0 mg, 0.346 mmol) in n-BuOH (1 mL) were added aminomethyl-cyclopropane (28.7 mg, 0.391 mmol) and triethylamine (56.6 mg, 0.560 mmol) under an N$_2$ atmosphere. The reaction mixture was heated under microwave irradiation at 120° C. for 30 min. n-BuOH was evaporated, and the residue was dissolved in EtOAc and washed with water. The aqueous phase was further extracted with EtOAc, and the combined organic extracts were dried (MgSO$_4$), filtered, concentrated, and dried under high-vacuum overnight to yield 16g (87.1 mg, 0.328 mmol, 95%) as an amorphous colorless solid: IR (ATR, neat) 3260, 2970, 1621, 1578, 1302, 1253 cm$^{-1}$; $^1$H NMR (CDCl$_3$, 600 MHz) δ 7.67 (s, 1 H), 6.26 (bs, 1 H), 4.06 (t, 2 H, J=7.2 Hz), 3.45-3.35 (m, 2 H), 1.84 (sext, 2 H, J=7.2 Hz), 1.10-1.00 (m, 1 H), 0.89 (t, 2 H, J=7.2 Hz), 0.48 (dd, 2 H, J=13.8, 4.8 Hz), 0.23 (dd, 2 H, J=9.6, 4.8 Hz); $^{13}$C NMR (CDCl$_3$, 150 MHz) δ 155.0, 154.3, 149.9, 139.8, 118.4, 60.2, 45.6, 45.3, 23.2, 10.9, 10.5, 3.4.

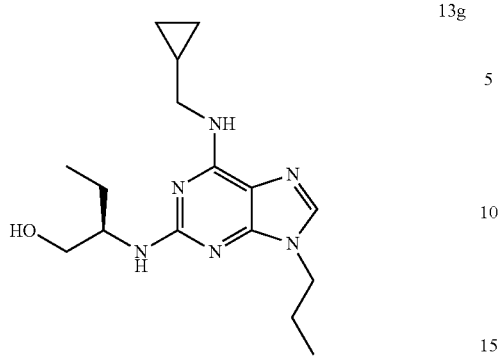

13g (R)-2-(6-(Cyclopropylmethylamino)-9-propyl-9H-purin-2-ylamino)butan-1-ol (13g). A mixture of 15a (50.0 mg, 0.188 mmol) and (R)-(−)-2-amino-1-butanol (89.2 mg, 0.941 mmol) was heated in a pressure tube immersed in an oil bath at 170° C. for 10 h. The reaction mixture was cooled to room temperature, diluted with water, and extracted with EtOAc (3×). The combined organic phases were washed with warm water (50-55° C., 2×), dried (MgSO$_4$), concentrated, and dried under high-vacuum to yield a yellow solid. Upon the addition of Et$_2$O to the solid, an off-white solid was precipitated. The solid was rinsed (Et$_2$O, 3×) by pipetting out the supernatant and dried under high-vacuum to yield 13g (37.4 mg, 0.117 mmol, 62%) as an off-white solid: Mp 146-149° C.; IR (ATR, neat) 3319, 2966, 2847, 1611, 1489 cm$^{-1}$; $^1$H NMR (CDCl$_3$, 600 MHz) δ 7.42 (s, 1 H), 5.81 (bs, 1 H), 5.51 (bs, 1 H), 4.96-4.88 (m, 1 H), 3.94 (t, 2 H, J=7.2 Hz), 3.91-3.85 (m, 1 H), 3.82 (d, 1 H, J=10.2 Hz), 3.63 (dd, 1 H, J=10.2, 8.4 Hz), 3.38 (bs, 2 H), 1.84 (sext, 2 H, J=7.2 Hz), 1.68-1.49 (m, 2 H), 1.15-1.05 (m, 1 H), 1.01 (t, 3 H, J=7.2 Hz), 0.92 (t, 3 H, J=7.2 Hz), 0.55-0.50 (m, 2 H), 0.28-0.23 (m, 2 H); $^{13}$C NMR (CDCl$_3$, 150 MHz) δ 160.2, 154.8, 150.5, 136.9, 114.2, 68.4, 56.3, 45.4, 45.0, 25.0, 23.1, 11.1, 10.9, 10.8, 3.4; HRMS (EI) m/z calcd for C$_{16}$H$_{26}$N$_6$O 318.2168, found 318.2168.

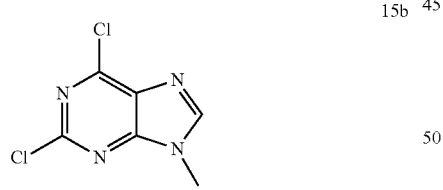

15b 2,6-Dichloro-9-methyl-9H-purine (15b). To a solution of 2,6-dichloro-9H-purine (0.120 g, 0.635 mmol) in anhydrous DMF (1.0 mL) was added K$_2$CO$_3$ (0.270 g, 1.95 mmol) followed by iodomethane (0.20 mL, 3.21 mmol) at 0° C. The reaction mixture was stirred for 5 h at 0° C., quenched with water and extracted with EtOAc. The organic layers were combined, washed with brine, dried (MgSO$_4$), concentrated, and purified by chromatography on SiO$_2$ (hexanes, 100%, to EtOAc, 100%) to yield 15b (83.0 mg, 0.409 mmol, 64% yield) as a colorless solid: IR (ATR, neat) 3067, 1554, 1360, 1333, 1223, 1147 cm$^{-1}$; $^1$H NMR (CDCl$_3$, 600 MHz) δ 8.09 (s, 1 H), 3.89 (s, 3H); $^{13}$C NMR (CDCl$_3$, 150 MHz) δ 153.3, 152.7, 151.3, 146.4, 130.4, 30.4.

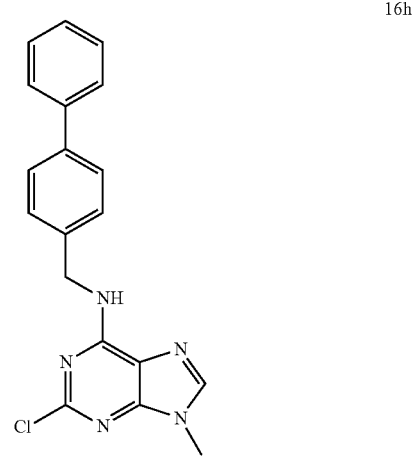 [SMILES: Cn1cnc2c(NCc3ccc(-c4ccccc4)cc3)nc(Cl)nc21]

16h

N-(Biphenyl-4-ylmethyl)-2-chloro-9-methyl-9H-purin-6-amine (16h). To a solution of 15b (60.0 mg, 0.296 mmol) in n-BuOH (1.0 mL) were added 4-phenylbenzylamine (58.6 mg, 0.310 mmol) and triethylamine (48.6 mg, 0.476 mmol) under an N$_2$ atmosphere. The reaction mixture was heated under microwave irradiation at 120° C. for 30 min n-BuOH was evaporated, and the residue was dissolved in EtOAc and washed with water. The aqueous phase was further extracted with EtOAc, and the combined organic layers were dried (MgSO$_4$) and concentrated to yield a colorless solid. The solid was resuspended (hexanes/Et$_2$O, 2:1), filtered, triturated (hexanes/Et$_2$O, 2:1), and dried under high-vacuum to yield 16h (89.0 mg, 0.254 mmol, 86%) as an off-white solid: IR (ATR, neat) 3214, 2387, 1620, 1602, 1482, 1308, 1233 cm$^{-1}$; $^1$H NMR (CDCl$_3$/CD$_3$OD, 9/1, 600 MHz) δ 7.64 (bs, 1 H), 7.49 (d, 4 H, J=7.8 Hz), 7.38 (d, 2 H, J=7.8 Hz), 7.34 (t, 2 H, J=7.8 Hz), 7.25 (t, 1 H, J=7.8 Hz), 4.74 (bs, 2 H), 3.77 (s, 3 H); $^{13}$C NMR (CDCl$_3$/CD$_3$OD, 9/1, 150 MHz) δ 154.7, 154.5, 150.1, 140.5, 140.4, 140.3, 136.7, 128.6, 128.2, 127.1, 126.8, 117.8, 44.1, 29.8.

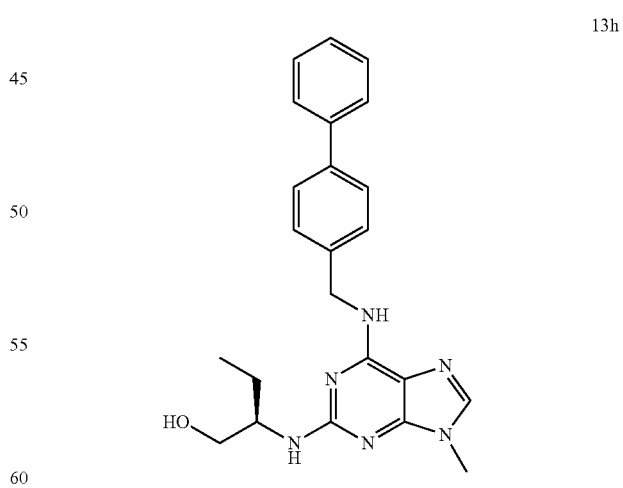

13h (R)-2-(6-(Biphenyl-4-ylmethylamino)-9-methyl-9H-purin-2-ylamino)butan-1-ol (13h). A mixture of 16h (50.0 mg, 0.143 mmol) and (R)-(−)-2-amino-1-butanol (68.4 mg, 0.721 mmol) was heated in a microwave vial immersed in an oil bath at 170° C. for 15 h. The reaction mixture was cooled to room temperature, diluted with water, and extracted with EtOAc (3×). The combined organic phases were washed with warm water (50-55° C., 2×) dried (MgSO$_4$), concentrated, and dried under high-vacuum to yield an oily, yellow-green residue. Addition of Et$_2$O and hexanes resulted in the precipitation of a light green solid. The solid was rinsed (Et$_2$O, 3×) by pipetting out the supernatant and dried under high-vacuum at 40° C. to yield impure product (90% purity). The solid and filtrate were combined, preadsorbed onto SiO$_2$ and purified by chromatography on SiO$_2$ (hexanes/EtOAc, 1:1, to EtOAc/Et$_3$N, 99:1, to EtOAc/MeOH/Et$_3$N, 98:10:1) to yield 13h (35.7 mg, 0.0887 mmol, 62%) as a light green solid: Mp 133-136° C.; IR (ATR, neat) 3290, 2927, 1600, 1487 cm$^{-1}$; $^1$H NMR (CDCl$_3$, 600 MHz) δ 7.59 (d, 2 H, J=7.2 Hz), 7.56 (d, 2 H, J=7.8 Hz), 7.47-7.43 (m, 4 H), 7.41 (s, 1 H), 7.35 (t, 1 H, J=7.2 Hz), 6.00 (bs, 1 H), 4.97-4.87 (m, 1 H), 4.83 (bs, 2 H), 4.00-3.90 (m, 1 H), 3.83 (dd, 1 H, J=10.8, 2.4 Hz), 3.66 (s, 3 H), 3.64 (dd, 1 H, J=10.8, 7.8 Hz), 1.68-1.52 (m, 2 H), 1.03 (t, 3 H, J=7.2 Hz); $^{13}$C NMR (CDCl$_3$, 150 MHz) δ 160.3, 154.8, 151.0, 140.8, 140.2, 137.8, 137.6, 128.7, 128.1, 127.3, 127.0, 114.2, 68.2, 56.2, 44.1, 29.4, 25.0, 10.9; HRMS (EI) m/z calcd for C$_{23}$H$_{26}$N$_6$O 402.2168, found 402.2178.

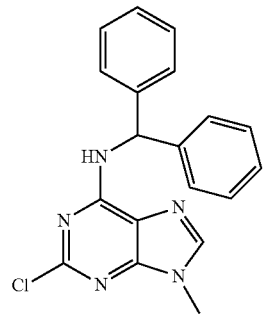

16i

2-Chloro-N-(2,2-diphenylethyl)-9-methyl-9H-purin-6-amine (16i). To a solution of 15b (68.0 mg, 0.335 mmol) in n-BuOH (1.0 mL) was added aminodiphenylmethane (66.2 mg, 0.350 mmol) and triethylamine (55.1 mg, 0.539 mmol) under an N$_2$ atmosphere. The reaction mixture was heated under microwave irradiation at 120° C. for 30 min. n-BuOH was evaporated, and the residue was dissolved in EtOAc and washed with water. The aqueous phase was further extracted with EtOAc, and the combined organic extracts were dried (MgSO4) and concentrated to yield a colorless solid. The solid was resuspended (hexanes/Et$_2$O, 2:1), filtered, triturated (hexanes/Et$_2$O, 2:1), and dried under high-vacuum to yield 16i (83.0 mg, 0.237 mmol, 71%) as an off-white, crude solid that was used without further purification: Characteristic signals: $^1$H NMR (CDCl$_3$, 600 MHz) δ 7.40-7.20 (m, 12 H), 6.75 (bs, 1 H), 3.69 (s, 3 H); $^{13}$C NMR (CDCl$_3$, 150 MHz) δ 154.5, 154.2, 150.7, 141.3, 140.9, 128.5, 127.6, 127.4, 118.4, 57.3, 29.9.

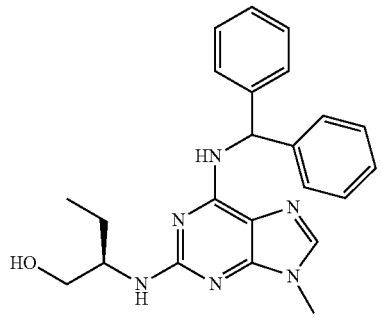

13i (R)-2-(6-(2,2-Diphenylethylamino)-9-methyl-9H-purin-2-ylamino)butan-1-ol (13i). A mixture of 16i (50.0 mg, 0.143 mmol) and (R)-(−)-2-amino-1-butanol (68.4 mg, 0.721 mmol) was heated in a microwave vial immersed in an oil bath at 170° C. for 15 h. The reaction mixture was cooled to room temperature, diluted with water, and extracted with EtOAc (3×). The combined organic phases were washed with warm water (50-55° C., 2×) dried (MgSO$_4$), concentrated, and dried under high-vacuum at 50° C. (oil bath) for 2 h to yield an oily green residue. The crude residue was adsorbed onto SiO$_2$ and purified by chromatography on SiO$_2$ (hexanes/EtOAc, 1:1, to EtOAc/Et$_3$N, 99:1, to EtOAc/MeOH/Et$_3$N, 94:5:1) to yield 13i (36.5 mg, 0.0907 mmol, 63%) as an off-white solid: Mp 130-134° C.; IR (ATR, neat) 3301 (br), 2932, 1597, 1474 cm$^{-1}$; $^1$H NMR (CDCl$_3$, 600 MHz) δ 7.40-7.20 (m, 10 H), 6.60-6.40 (m, 2 H), 4.83 (d, 1 H, J=6.0 Hz), 3.80-3.75 (m, 1 H), 3.70-3.65 (m, 1 H), 3.59 (s, 3 H), 3.60-3.50 (m, 1 H), 1.60-1.40 (m, 2 H), 0.94 (t, 3H, J=7.2 Hz); $^{13}$C NMR (CDCl$_3$, 150 MHz) δ 160.1, 153.9, 151.2, 142.1, 137.6, 128.51, 128.48, 127.57, 127.55, 127.3, 127.2, 114.1, 67.5, 58.0, 55.8, 29.3, 24.8, 10.8; HRMS (EI) m/z calcd for C$_{23}$H$_{26}$N$_6$O 402.2168, found 402.2170.

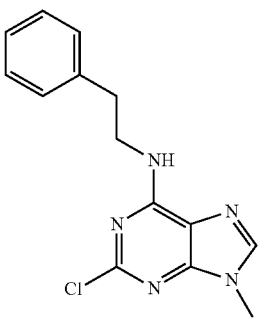

16j

2-Chloro-9-methyl-N-phenethyl-9H-purin-6-amine (16j). To a solution of 15b (60.0 mg, 0.296 mmol) in n-BuOH (1.0 mL) was added phenethylamine (38.0 mg, 0.312 mmol) and triethylamine (47.9 mg, 0.474 mmol) under an N$_2$ atmosphere. The reaction mixture was heated under microwave irradiation at 120° C. for 30 min. n-BuOH was evaporated, and the residue was dissolved in EtOAc and washed with water. The aqueous phase was further extracted with EtOAc, and the combined organic extracts were dried (MgSO$_4$) and concentrated to yield a colorless solid. The solid was resuspended (hexanes/Et$_2$O, 3:1), filtered, triturated (hexanes/Et$_2$O, 3:1), and dried under high-vacuum to yield 16j (71.0 mg, 0.247 mmol, 83%) as an off-white amorphous solid: IR (ATR, neat) 3233, 1615, 1578, 1299, 1231 cm$^{-1}$; $^1$H NMR (CDCl$_3$, 600 MHz) δ 7.49 (bs, 1 H), 7.27 (d, 2 H, J=7.2 Hz), 7.24-7.18 (m, 3 H), 6.41 (bs, 1 H), 3.93-3.83 (m, 2 H), 3.77 (s, 3 H), 2.97 (t, 2H, J=7.2 Hz); $^{13}$C NMR (CDCl$_3$, 150 MHz) δ 155.1, 154.6, 150.3, 140.5, 138.7, 128.8, 128.5, 126.4, 118.5, 41.9, 35.5, 29.9.

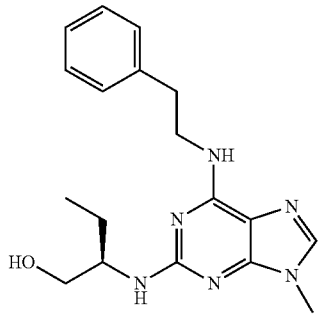

13j (R)-2-(9-Methyl-6-(phenethylamino)-9H-purin-2-ylamino)butan-1-ol (13j). A mixture of 16j (50.0 mg, 0.174 mmol) and (R)-(-)-2-amino-1-butanol (83.6 mg, 0.882 mmol) was heated in a microwave vial immersed in an oil bath at 170° C. for 15 h. The reaction mixture was cooled to room temperature, diluted with water, and extracted with EtOAc (3×). The combined organic phases were washed with warm water (50-55° C., 2×), dried (MgSO$_4$), concentrated, and dried under high-vacuum to yield an oily yellow residue. Addition of Et$_2$O and a few drops of hexanes to the solid resulted in the precipitation of an off-white solid. The solid was rinsed (Et$_2$O, 3×) by pipetting out the supernatant and dried under high-vacuum at 40° C. The solid and the filtrate were combined, adsorbed onto SiO$_2$, and purified by chromatography on SiO$_2$ (hexanes/EtOAc, 1:1, to EtOAc/Et$_3$N, 99:1, to EtOAc/MeOH/Et$_3$N, 94:5:1) to yield 13j (37.8 mg, 0.111 mmol, 64%) as a light green solid: Mp 108-110° C.; IR (ATR, neat) 3922 (br), 2931, 1598, 1488 cm$^{-1}$; $^1$H NMR (CDCl$_3$, 600 MHz) δ 7.39 (s, 1 H), 7.32-7.24 (m, 4 H), 7.22 (t, 1 H, J=7.2 Hz), 5.65 (bs, 1 H), 5.13 (bs, 1 H), 4.93-4.85 (m, 1 H), 3.97-3.90 (m, 1 H), 3.90-3.75 (m, 3 H), 3.673.63 (m, 1 H), 3.63 (s, 3 H), 2.96 (t, 2 H, J=7.2 Hz), 1.70-1.55 (m, 2 H), 1.04 (t, 3 H, J=7.2 Hz); $^{13}$C NMR (CDCl$_3$, 150 MHz) δ 160.3, 154.9, 150.9, 139.0, 137.5, 128.8, 128.6, 126.4, 114.2, 68.3, 56.2, 41.7, 35.9, 29.3, 25.0, 10.9; HRMS (EI) m/z calcd for C$_{18}$H$_{24}$N$_6$O 340.2012, found 340.2014.

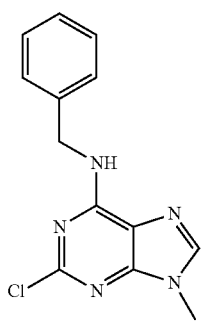

16k

N-Benzyl-2-chloro-9-methyl-9H-purin-6-amine (16k). To a solution of 15b (71.0 mg, 0.350 mmol) in n-BuOH (1.0 mL) were added benzylamine (40.50 mg, 0.370 mmol) and triethylamine (56.6 mmol, 0.560 mmol) under an N$_2$ atmosphere. The reaction mixture was heated under microwave irradiation at 120° C. for 30 min. n-BuOH was evaporated, and the residue was dissolved in EtOAc and washed with water. The aqueous phase was further extracted with EtOAc, and the combined organic extracts were dried (MgSO$_4$) and concentrated to yield a colorless solid. The solid was resuspended (hexanes/Et$_2$O, 3:1), filtered, triturated (hexanes/Et$_2$O, 3:1), and dried under high-vacuum to yield 16k (65.5 mg, 0.239 mmol, 68%) as a colorless solid: IR (ATR, neat) 2385, 1596, 1572, 1325, 1232 cm$^{-1}$; $^1$H NMR (CDCl$_3$/CD$_3$OD, 9/1, 600 MHz) δ 7.72 (bs, 1 H), 7.40 (d, 2 H, J=7.2 Hz), 7.35 (t, 2 H, J=7.2 Hz), 7.29 (t, 1 H, J=7.2 Hz), 4.79 (bs, 2 H), 3.79 (s, 3H); $^{13}$C NMR (CDCl$_3$/CD$_3$OD, 9/1, 150 MHz) δ 154.7, 154.5, 150.1, 140.5, 137.6, 128.4, 127.7, 127.4, 117.8, 44.4, 29.8.

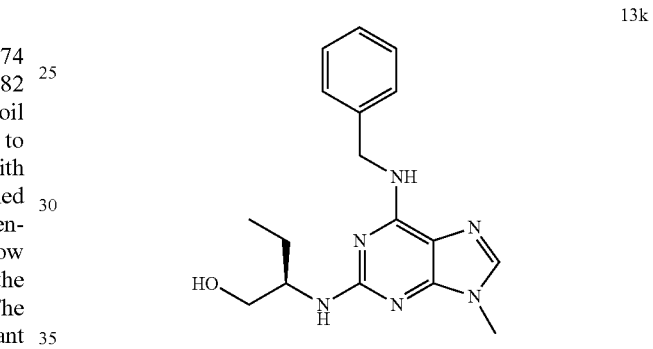

13k (R)-2-(6-(Benzylamino)-9-methyl-9H-purin-2-ylamino)butan-1-ol (13k). A mixture of 16k (49.0 mg, 0.179 mmol) and (R)-(-)-2-amino-1-butanol (85.5 mg, 0.902 mmol) was heated in a microwave vial immersed in an oil bath at 170° C. for 11 h. The reaction mixture was cooled to room temperature, diluted with water, and extracted with EtOAc (3×). The combined organic phases were washed with warm water (50-55° C., 2×), dried (MgSO$_4$), concentrated, and dried under high-vacuum at 50° C. (oil bath) for 2 h to yield a yellow solid. The addition of Et2O to the solid resulted in the precipitation of an off-white solid. The solid was rinsed (Et20, 3×) by pipetting out the supernatant and dried under high-vacuum overnight at 40° C. to yield an off-white solid. The crude mixture was purified by chromatography on SiO$_2$ (hexanes/EtOAc, 1:1, to EtOAc/MeOH/Et3N, 94:5:1, to EtOAc/MeOH/Et3N, 85:14:1) to yield 13k (35.5 mg, 0.109 mmol, 61%) as a light yellow solid: Mp 118-120° C.; IR (ATR, neat) 3261 (br), 2958, 1610, 1493 cm$^{-1}$; $^1$H NMR (CDCl$_3$, 600 MHz) δ 7.40-7.25 (m, 6 H), 6.20 (bs, 1 H), 5.00-4.92 (m, 1 H), 4.74 (bs, 2 H), 3.95-3.90 (m, 1 H), 3.81 (dd, 1 H, J=10.8, 2.4 Hz), 3.62 (s, 3 H), 3.67-3.58 (m, 1 H), 1.67-1.52 (m, 2 H), 1.01 (t, 3 H, J=7.2 Hz); $^{13}$C NMR (CDCl$_3$, 150 MHz) δ 160.3, 154.8, 151.0, 138.7, 137.5, 128.5, 127.6, 127.2, 114.1, 67.9, 56.0, 44.3, 29.3, 24.9, 10.9; HRMS (EI) m/z calcd for C$_{17}$H$_{22}$N$_6$O 326.1855, found 326.1843.

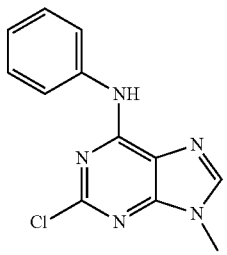

161

2-Chloro-9-methyl-N-phenyl-9H-purin-6-amine (161). To a solution of 15b (72.0 mg, 0.355 mmol) in n-BuOH (1.0 mL) were added aniline (34.0 mg, 0.365 mmol) and triethylamine (57.4 mg, 0.567 mmol) under an $N_2$ atmosphere. The reaction mixture was heated under microwave irradiation at 120° C. for 30 min n-BuOH was evaporated, and the residue was dissolved in EtOAc and washed with water. The aqueous phase was further extracted with EtOAc, and the combined organic extracts were dried (MgSO$_4$) and concentrated to yield a colorless solid. The solid was resuspended (hexanes/Et$_2$O, 3:1), filtered, triturated (hexanes/Et$_2$O, 3:1), and dried under high-vacuum to yield 161 (59.7 mg, 0.230 mmol, 65%) as a colorless amorphous solid: IR (ATR, neat) 3286, 1620, 1574, 1437, 1308, 1236 cm$^{-1}$; $^1$H NMR (CDCl$_3$, 600 MHz) δ 7.85 (bs, 1 H), 7.80-7.70 (m, 3 H), 7.45-7.35 (m, 2 H), 7.20-7.10 (m, 1 H), 3.84 (s, 3 H); $^{13}$C NMR (CDCl$_3$, 150 MHz) δ 154.2, 152.3, 151.0, 141.4, 137.9, 129.1, 124.0, 120.2, 119.1, 30.1.

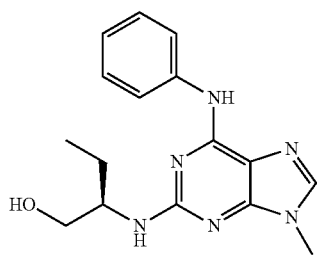

131

(R)-2-(9-Methyl-6-(phenylamino)-9H-purin-2-ylamino) butan-1-ol (131). A mixture of 161 (46.0 mg, 0.177 mmol) and (R)-(−)-2-amino-1-butanol (85.5 mg, 0.902 mmol) was heated in a microwave vial immersed in an oil bath at 170° C. for 11 h. The reaction mixture was cooled to room temperature, diluted with water, and extracted with EtOAc (3×). The combined organic phases were washed with warm water (50-55° C., 2×) dried (MgSO$_4$), concentrated, and dried under high-vacuum to yield a light green solid. The solid was preadsorbed on SiO$_2$ and purified by chromatography on SiO$_2$ (hexanes/EtOAc, 1:1, to EtOAc/Et$_3$N, 99:1, to EtOAc/MeOH/Et$_3$N, 90:9:1) to yield 131 (29.8 mg, 0.0954 mmol, 54%) as an off-white, slightly light green solid: Mp 202-206° C.; IR (ATR, neat) 3222, 3133 (br), 2930, 1579, 1498, 1442 cm$^{-1}$; $^1$H NMR (CDCl$_3$/CD$_3$OD, 9/1, 600 MHz) δ 7.66 (dd, 2 H, J=7.2, 1.2 Hz), 7.43 (s, 1 H), 7.25 (t, 2 H, J=7.2 Hz), 6.97 (td, 1 H, J=7.2, 1.2 Hz), 3.90 (s, 3 H), 3.92-3.85 (m, 1 H), 3.67 (dd, 1 H, J=10.8, 3.6 Hz), 3.57-3.53 (m, 1 H), 1.65-1.50 (m, 2 H), 0.92 (t, 3 H, J=7.2 Hz); $^{13}$C NMR (CDCl$_3$/CD$_3$OD, 9/1, 150 MHz) δ 159.6, 152.1, 151.1, 138.9, 137.79, 137.78, 128.6, 122.9, 119.9, 113.5, 65.2, 55.0, 29.1, 24.3, 10.4; HRMS (EI) m/z calcd for C$_{16}$H$_{20}$N$_6$O 312.1699, found 312.1693.

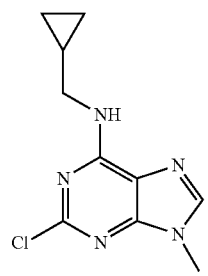

16m

2-Chloro-N-(cyclopropylmethyl)-9-methyl-9H-purin-6-amine (16m). To a solution of 15b (70.0 mg, 0.345 mmol) in n-BuOH (1.0 mL) were added aminomethyl-cyclopropane (30.0 mg, 0.4092 mmol) and triethylamine (55.9 mg, 0.552 mmol) under an $N_2$ atmosphere. The reaction mixture was heated under microwave irradiation at 120° C. for 30 min. n-BuOH was evaporated, and the residue was dissolved in EtOAc and washed with water. The aqueous phase was further extracted with EtOAc, and the combined organic extracts were dried (MgSO$_4$), concentrated, and dried under high-vacuum overnight to yield 16m (77.9 mg, 0.328 mmol, 95% yield) as a colorless solid: IR (ATR, neat) 3260, 1618, 1581, 1301, 1234 cm$^{-1}$; $^1$H NMR (CDCl$_3$, 600 MHz) δ 7.68 (s, 1 H), 6.07 (bs, 1 H), 3.78 (s, 3 H), 3.50-3.40 (m, 2 H), 1.13-1.07 (m, 1 H), 0.55 (dd, 2 H; J=12.6, 4.8 Hz), 0.30 (dd, 2 H, J=9.6, 4.8 Hz); $^{13}$C NMR (CDCl$_3$, 150 MHz) δ 155.1, 154.6, 150.3, 140.5, 118.5, 45.8, 30.0, 10.5, 3.5.

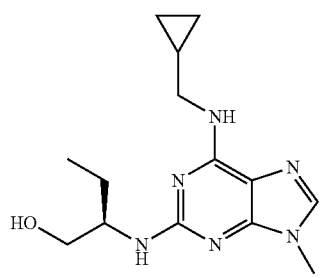

13m

(R)-2-(6-(Cyclopropylmethylamino)-9-methyl-9H-purin-2-ylamino)butan-1-ol (13m). A mixture of 16m (50.0 mg, 0.210 mmol) and (R)-(−)-2-amino-1-butanol (95.0 mg, 1.00 mmol) was heated in a microwave vial immersed in an oil bath at 170° C. for 11 h. The reaction was cooled to room temperature, diluted with water, and extracted with EtOAc (3×). The combined organic phases were washed with warm water (50-55° C., 2×), dried (MgSO$_4$), concentrated, and dried under high-vacuum to yield a green solid. Addition of Et$_2$O to the solid resulted in the precipitation of an off-white solid. The solid was rinsed (Et$_2$O, 3×) by pipetting out the supernatant and dried under high-vacuum to yield a light green solid. The crude residue was purified by chromatography on SiO$_2$ (hexanes/EtOAc, 1:1, to EtOAc/MeOH/Et$_3$N, 94:5:1, to EtOAc/MeOH/Et$_3$N, 84:15:1) to yield 13m (35.8 mg, 0.123 mmol, 59%) as a crystalline green solid: Mp 147-150° C.; IR (ATR, neat) 3328, 3078, 2849, 1610, 1490 cm$^{-1}$; $^1$H NMR (CDCl$_3$, 600 MHz) δ 7.40 (s, 1 H), 5.83 (bs, 1H), 5.37 (bs, 1 H), 5.00-4.87 (m, 1 H), 3.95-3.88 (m, 1 H), 3.82 (d, 1 H, J=10.8 Hz), 3.67-3.58 (m, 1 H), 3.62 (s, 3 H), 3.39 (bs, 2 H), 1.68-1.50 (m, 2 H), 1.131.03 (m, 1 H), 1.02 (t, 3 H, J=7.2 Hz), 0.58-0.48 (m, 2 H), 0.31-0.21 (m, 2 H); $^{13}$C NMR (CDCl$_3$, 150 MHz) δ 160.3, 154.8, 150.8, 137.3, 114.0, 68.1, 56.1, 45.4, 29.3, 25.0, 10.9, 10.8, 3.4; HRMS (EI) m/z calcd for C$_{14}$H$_{22}$N$_6$O 290.1855, found 290.1850.

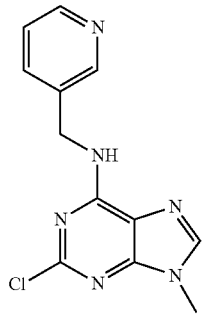

16n

2-Chloro-9-methyl-N-(pyridin-3-ylmethyl)-9H-purin-6-amine (16n). To a solution of 15b (72.0 mg, 0.355 mmol) in n-BuOH (1.0 mL) was added 3-(aminomethyl)pyridine (39.7 mg, 0.367 mmol) and triethylamine (57.5 mg, 0.568 mmol) under an N$_2$ atmosphere. The reaction mixture was heated under microwave irradiation at 120° C. for 30 min. n-BuOH was evaporated, and the residue was dissolved in EtOAc and washed with water. The aqueous phase was further extracted with EtOAc, and the combined organic extracts were dried (MgSO$_4$) and concentrated to yield a colorless solid. The solid was resuspended (hexanes/Et$_2$O, 1:1), filtered, triturated (hexanes/Et$_2$O, 1:1), and dried under high-vacuum to yield 16n (76.0 mg, 0.277 mmol, 78%) contaminated with a small amount (~10%) of EtOAc and Et$_2$O as a fine yellow amorphous solid that was used for the next reaction without further purification: IR (ATR, neat) 3076, 2401, 1603, 1579, 1313, 1232 cm$^{-1}$; $^1$H NMR (CDCl$_3$/CD3OD, 9/1, 600 MHz) δ 8.50 (bs, 1 H), 8.35 (bs, 1 H), 7.71 (d, 1 H, J=7.8 Hz), 7.65 (s, 1 H), 7.25-7.20 (m, 1 H), 4.70 (bs, 2 H), 3.68 (s, 3 H); $^{13}$C NMR (CDCl$_3$/CD3OD, 9/1, 150 MHz) δ 154.6, 154.3, 148.6, 147.9, 140.7, 136.2, 134.1, 123.6, 117.8, 41.6, 29.8.

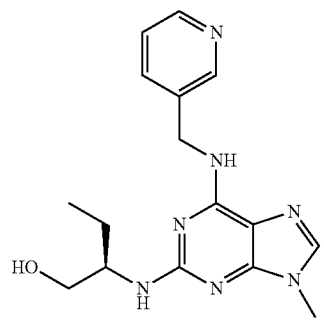

13n (R)-2-(9-Methyl-6-(pyridin-3-ylmethylamino)-9H-purin-2-ylamino)butan-1-ol (13n). A mixture of 16n (70.0 mg, 0.255 mmol) and (R)-(−)-2-amino-1-butanol (124 mg, 1.30 mmol) was heated in a microwave vial immersed in an oil bath at 170° C. for 8.5 h. The reaction mixture was cooled to room temperature, diluted with water, and extracted with EtOAc (3×). The combined organic phases were washed with warmed water (50-55° C., 2×) dried (MgSO$_4$), concentrated, and dried under high-vacuum to yield an oily, green solid. Addition of Et$_2$O and a few drops of hexanes to the solid resulted in the precipitation of a dark green solid. The solid was carefully crushed with a glass rod, rinsed (Et$_2$O, 3×) by pipetting out the supernatant, and dried under high-vacuum overnight to yield a light green solid. The crude residue was purified by chromatography on SiO$_2$ (hexanes/EtOAc, 1:1, to EtOAc/MeOH/Et$_3$N, 78:20:2) to yield 16n (32.6 mg, 0.0936 mmol, 37%) as a green-gray solid: Mp 136-139° C.; IR (ATR, neat) 3256 (br), 2930, 1603, 1551, 1477 cm$^{-1}$; $^1$H NMR (CDCl$_3$, 600 MHz) δ 8.59 (d, 1 H, J=1.8 Hz), 8.47 (dd, 1 H, J=4.8, 1.8 Hz), 7.65 (d, 1 H, J=7.8 Hz), 7.36 (s, 1 H), 7.20 (dd, 1 H, J=7.8, 4.8 Hz), 6.58 (bs, 1 H), 5.08-5.00 (m, 1 H), 4.72 (bs, 2 H), 3.94-3.88 (m, 1 H), 3.76 (dd, 1 H, J=10.8, 2,4 Hz), 3.61 (s, 3 H), 3.59 (dd, 1 H, J=10.8, 7.2 Hz), 1.66-1.59 (m, 1 H), 1.55-1.49 (m, 1 H), 0.98 (t, 3 H, J=7.2 Hz); $^{13}$C NMR (CDCl$_3$, 150 MHz) δ 160.0, 154.5, 151.1, 149.2, 148.5, 137.7, 135.3, 134.5, 123.4, 113.9, 67.3, 55.9. 41.8, 29.4, 24.9, 10.8; IR (ATR, neat) 3256 (br), 2930, 1603, 1551, 1477 cm$^{-1}$; HRMS (EI) m/z calcd for C$_{16}$H$_{21}$N$_7$O 327.1808, found 327.1806.

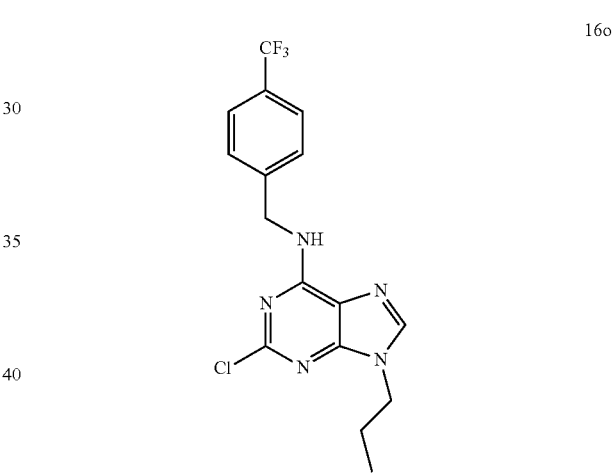

16o

2-Chloro-9-propyl-W-(4-(trifluoromethyl)benzyl)-9H-purin-6-amine (16o). To a solution of 15a (80.0 mg, 0.346 mmol) in n-BuOH (1.0 mL) were added 4-(trifluoromethyl) benzylamine (63.9 mg, 0.358 mmol) and triethylamine (55.9 mg, 0.552 mmol) under an N$_2$ atmosphere. The reaction mixture was heated under microwave irradiation at 120° C. for 30 min. n-BuOH was evaporated, and the residue was dissolved in EtOAc and washed with water. The aqueous phase was further extracted with EtOAc, and the combined organic extracts were dried (MgSO$_4$), and concentrated to yield a colorless solid. The solid was resuspended (hexanes/Et$_2$O, 3:1), filtered, triturated (hexanes/Et$_2$O, 3:1), and dried under high-vacuum to yield 16o (78.0 mg, 0.211 mmol, 61%) as a colorless amorphous solid: IR (ATR, neat) 3261, 1630, 1580, 1325, 1308, 1253 cm$^{-1}$; $^1$H NMR (CDCl$_3$, 600 MHz) δ 7.58 (d, 2 H, J=7.8 Hz), 7.52-7.45 (m, 3 H), 6.96 (bs, 1 H), 4.90 (bs, 2H), 4.09 (t, 2 H, J=7.2 Hz), 1.87 (sext, 2 H, J=7.2 Hz), 0.94 (t, 3 H, J=7.2 Hz); $^{13}$C NMR (CDCl$_3$, 150 MHz) δ 155.0, 154.4, 150.4, 142.3, 140.3, 129.8 (q, J=33 Hz), 128.0, 125.5 (q, J=3 Hz), 124.0 (q, J=270 Hz), 118.6, 45.5, 43.9, 23.3, 11.0.

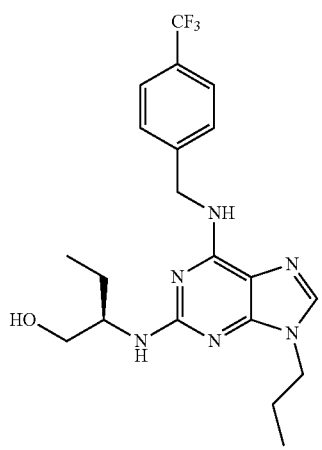

13o (R)-2-(9-Propyl-6-(4-(trifluoromethyl)benzylamino)-9H-purin-2-ylamino)butan-1-ol (13o). A mixture of 16o (50.0 mg, 0.135 mmol) and (R)-(−)-2-amino-1-butanol (71.3 mg, 0.751 mmol) was heated in a microwave vial immersed in an oil bath at 170° C. for 12 h. The reaction mixture was cooled to room temperature, diluted with water, and extracted with EtOAc (3×). The combined organic phases were washed with warm water (50-55° C., 2×), dried (MgSO$_4$), concentrated, and dried under high-vacuum to yield a yellow solid. Addition of Et$_2$O/hexanes (1:1) to the solid resulted in the precipitation of a light green solid. The solid was rinsed (Et$_2$O/hexanes, 1:1) by pipetting out the supernatant and dried under high-vacuum overnight at 40° C. to yield 13o (38.3 mg, 0.0907 mmol, 67%) as a light green crystalline solid: Mp 124-127° C.; IR (ATR, neat) 3266, 2962, 1600, 1545, 1326, 1104 cm$^{-1}$; $^1$H NMR (CDCl$_3$, 600 MHz) δ 7.56 (d, 2 H, J=8.4 Hz), 7.46 (d, 2 H, J=7.8 Hz), 7.38 (s, 1 H), 6.40 (bs, 1 H), 4.91 (d, 1 H, J=6.0 Hz), 4.95-4.75 (m, 2 H), 3.95 (t, 2 H, J=7.2 Hz), 3.89-3.82 (m, 1 H), 3.80 (dd, 1 H, J=10.8, 1.8 Hz), 3.61 (dd, 1 H, J=10.8, 7.8 Hz), 1.85 (sextet, 2 H, J=7.2 Hz), 1.64-1.49 (m, 2 H), 0.99 (t, 3 H, J=7.2 Hz), 0.94 (t, 3H, J=7.2 Hz); $^{13}$C NMR (CDCl$_3$, 150 MHz) δ 160.1, 154.7, 150.8, 143.2, 137.3, 129.4 (q, J=33 Hz), 127.7, 125.4 (q, J=3 Hz), 124.1 (q, J=270 Hz), 114.3, 68.2, 56.2, 45.1, 43.8, 24.9, 23.2, 11.2, 10.9; HRMS (EI) m/z calcd for C$_{20}$H$_{25}$F$_3$N$_6$O 422.2042, found 422.2038.

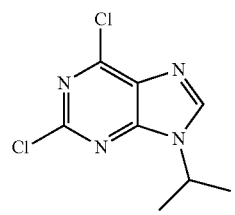

15c 2,6-Dichloro-9-isopropyl-9H-purine (15c). To a solution of 2,6-dichloro-9H-purine (0.500 g, 2.65 mmol) in anhydrous DMSO (3.0 mL) cooled to 15° C. was added K$_2$CO$_3$ (1.10 g, 7.96 mmol) followed by 2-iodopropane (1.35 mL, 13.4 mmol). The mixture was stirred overnight at room temperature, quenched with water and extracted with EtOAc. The organic layers were combined, washed with brine, dried (MgSO$_4$), concentrated, and purified by chromatography on SiO$_2$ (hexanes, 100%, to hexanes/EtOAc, 1:1) to yield 15c (0.415 g, 1.80 mmol, 68%) as a colorless solid: Mp 149-151° C.; IR (ATR, neat) 1587, 1554, 1356, 1214 cm$^{-1}$; $^1$H NMR (CDCl$_3$, 600 MHz) δ 8.18 (s, 1 H), 4.92 (hept, 1 H, J=6.6 Hz), 1.65 (d, 6 H, J=6.6 Hz); $^{13}$C NMR (CDCl$_3$, 150 MHz) δ 152.7, 152.6, 151.6, 143.5, 131.0, 48.3, 22.5; HRMS (EI) m/z calcd for C$_8$H$_8$Cl$_2$N$_4$ 230.0126, found 230.0120.

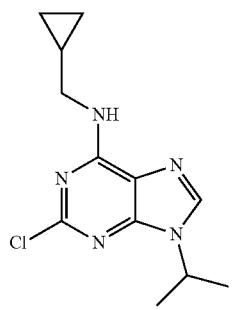

16p

2-Chloro-N-(cyclopropylmethyl)-9-isopropyl-9H-purin-6-amine (16p). To a solution of 15c (100 mg, 0.433 mmol) in n-BuOH (1.5 mL) were added cyclopropylmethanamine (36.9 mg, 0.519 mmol) and Et$_3$N (70.9 mg, 0.692 mmol). The reaction was heated under microwave irradiation at 120° C. for 20 min. n-BuOH was evaporated in vacuo. The residue was diluted with water (5.0 mL), and the mixture was extracted with EtOAc (3×7.0 mL). The combined organic extracts were dried (MgSO$_4$), filtered, and concentrated to yield a pale yellow solid. The residue was resuspended (hexanes/Et$_2$O, 2:1), filtered, and washed (hexanes/Et$_2$O, 3:1). The solid was filtered and dried under high-vacuum to yield 16p (60.3 mg, 0.227 mmol, 52%) as a pale yellow solid: Mp 70.2-72.7° C.; IR (ATR) 3286, 3086, 3068, 3055, 3038, 3030, 1647, 1627, 1592, 1575, 1560, 1446, 1314, 1273, 1204, 1174, 1159, 1150, 1075, 1027, 997, 943, 936, 917, 865, 813, 764, 719, 701, 691 cm$^{-1}$; $^1$H NMR (CDCl$_3$, 300 MHz) δ 7.80 (s, 1 H), 6.03 (bs, 1 H), 4.88-4.79 (hept, 1 H, J=6.9 Hz), 3.49 (bs, 2 H), 1.58 (d, 6 H, J=6.9 Hz), 1.20-1.10 (m, 1 H), 0.59 (q, 2 H, J=5.7 Hz), 0.32 (q, 2 H, J=4.5 Hz); $^{13}$C NMR (CDCl$_3$, 75 MHz) δ 155.2, 137.4, 118.9, 46.9, 45.9, 29.7, 22.8, 10.7, 3.6; EIMS m/z 265 (M+, 71), 238 (63), 236 (91), 230 (86), 194 (72), 182 (57), 86 (94), 84 (100); HRMS (EI) m/z calcd for C$_{12}$H$_{16}$ClN$_5$ 265.1094, found 265.1096.

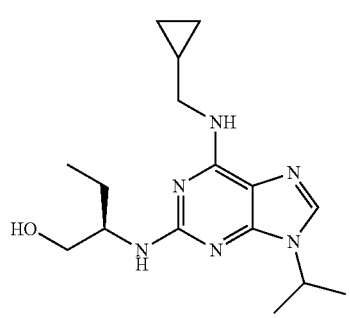

13p (R)-2-(6-(Cyclopropylmethylamino)-9-isopropyl-9H-purin-2-ylamino)butan-1-ol (13p). A mixture of 16p (50.0 mg, 0.188 mmol) and (R)-(−)-2-amino-1-butanol (124.0 mg, 1.40 mmol) was heated in a microwave vial immersed in an oil bath at 170° C. for 15 h. The reaction mixture was cooled to room temperature, diluted with water (7.0 mL), and extracted with EtOAc (4×10.0 mL). The combined organic phases were washed with warm water (50-55° C., 2×5.0 mL), dried (MgSO₄), concentrated, and dried under high-vacuum overnight to yield a yellow oil. The yellow oil was dissolved in EtOAc and suspended in Et₂O. Dropwise addition of hexanes (minimal solvent added to achieve a homogeneous supernatant) precipitated an off-white solid. The solid was rinsed (Et₂O/hexanes, 2:1) by pipetting out the supernatant and dried to obtain crude 13p (51.0 mg, 0.160 mmol, 85%) as an oil that was used without further purification: IR (ATR) 3286, 3086, 3068, 3055, 3038, 3030, 1647, 1627, 1592, 1575, 1560, 1446, 1314, 1273, 1204, 1174, 1159, 1150, 1075, 1027, 997, 943, 936, 917, 865, 813, 764, 719, 700, 691 cm$^{-1}$; $^1$H NMR (CDCl₃, 300 MHz) δ 7.52 (s, 1 H), 5.85 (bs, 1 H), 4.91 (bs, 1 H), 4.58(hept, 1 H, J=6.3 Hz), 3.92-3.80 (m, 2 H), 3.72-3.60 (m, 1 H), 3.60-3.30 (m, 2 H), 1.53 (d, 6 H, J=5.7 Hz), 1.40-0.90 (m, 4 H), 1.03 (t, 3 H, J=6.3 Hz), 0.57-0.52 (m, 2 H), 0.28 (bs, 2 H); $^{13}$C NMR (CDCl₃, 75 MHz) δ 160.1, 154.9, 134.4, 119.0, 114.6, 68.7, 56.4, 46.4, 29.7, 25.1, 22.6, 11.0, 3.5; EIMS m/z 318 (M⁺, 46), 288 (54), 287 (100), 265 (36), 236 (82), 230 (71), 194 (41), 134 (46), 119 (32); HRMS (EI) m/z calcd for C₁₆H₂₆N₆O 318.2168, found 318.2164.

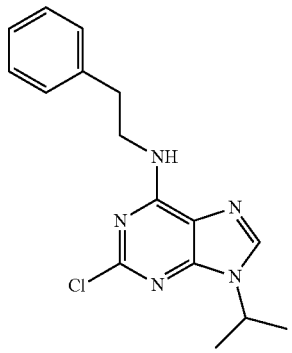

16q

2-Chloro-9-isopropyl-N-phenethyl-9H-purin-6-amine (16q). To a solution of 15c (100 mg, 0.433 mmol) in n-BuOH (1.5 mL) were added 2-phenylethylamine (62.9 mg, 0.519 mmol) and Et₃N (70.8 mg, 0.692 mmol). The reaction mixture was heated under microwave irradiation at 120° C. for 60 min. n-BuOH was evaporated in vacuo, the residue was diluted with water, and extracted with EtOAc (3×7.0 mL). The combined organic extracts were dried (MgSO₄) and concentrated to yield a pale yellow solid. The solid was resuspended (hexanes/Et₂O, 2:1), filtered, and subsequently rinsed (hexanes/Et₂O, 3:1). The filtered solid was dried under high-vacuum to yield 16q (112 mg, 0.353 mmol, 82%) as a pale yellow solid: Mp 146.7-148.7° C.; IR (ATR) 3252, 3217, 3211, 3205, 3123, 2974, 1616, 1580, 1569, 1457, 1444, 1347, 1308, 1292, 1221, 1198, 1059, 745 cm$^{-1}$; $^1$H NMR (CDCl₃, 300 MHz) δ 7.75 (bs, 1 H), 7.33-7.21 (m, 5 H), 5.99 (bs, 1 H), 4.83 (hept, 1 H, J=6.9 Hz), 3.91 (bs, 2 H), 3.00 (t, 2 H, J=7.2 Hz), 1.58 (d, 6 H, J=6.6 Hz); $^{13}$C NMR (CDCl₃, 75 MHz) δ 155.3, 149.7, 138.8, 137.5, 128.9, 128.6, 126.5, 118.9, 46.8, 42.0, 35.6, 22.9; EIMS m/z 315 (M⁺, 82), 337 (23), 226 (93), 213 (83), 169 (84), 146 (93), 119 (100), 104 (83), 77 (87), 65 (81); HRMS (EI) m/z calcd for C₁₆H₁₈ClN₅ 315.1251, found 315.1244.

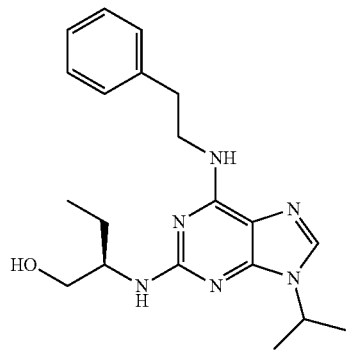

13q (R)-2-(9-Isopropyl-6-(phenethylamino)-9H-purin-2-ylamino)butan-1-ol (13q). A mixture of 16q (51.0 mg, 0.161 mmol) and (R)-(−)-2-amino-1-butanol (72.0 mg, 0.792 mmol) was heated in a microwave vial immersed in an oil bath at 170° C. for 15 h. The reaction mixture was cooled to room temperature, diluted with water, and extracted with EtOAc (4×10.0 mL). The combined organic layers were washed with warm water (50-55° C., 2×5 mL), dried (MgSO₄), filtered, concentrated, and dried under high-vacuum at 70° C. (oil bath) for 2 h to yield an oily, yellow residue. The crude residue was purified by chromatography on SiO₂ (hexanes/EtOAc, 1:1, to EtOAc/MeOH/Et₃N, 84:5:1) to yield 13q (20.4 mg, 0.0554 mmol, 34%) as a light yellow oil: IR (ATR) 3252, 3217, 3211, 3205, 3123, 2974, 1616, 1580, 1569, 1457, 1444, 1347, 1308, 1292, 1220, 1198, 1059, 745, 727 cm$^{-1}$; $^1$H NMR (CDCl₃, 300 MHz) δ 7.49 (s, 1 H), 7.34-7.20 (m, 5 H), 5.76 (bs, 1 H), 4.90 (d, 1 H, J=5.7 Hz), 4.63 (hept, 1 H, J=6.9 Hz), 3.95-3.80 (m, 4 H), 3.66 (dd, 2 H, J=7.8, 10.5 Hz), 2.97 (t, 2 H, J=7.2 Hz), 1.70-1.50 (m, 2 H), 1.53 (d, 6 H, J=6.6 Hz), 1.05 (t, 3 H, J=7.5 Hz); $^{13}$C NMR (CDCl₃, 75 MHz) δ 160.4, 155.2, 139.3, 134.7, 129.1, 128.9, 126.7, 115.0, 69.0, 56.7, 46.6, 42.1, 36.3, 25.3, 22.9, 11.3; EIMS m/z 368 (M⁺, 84), 338 (77), 277 (43), 205 (77), 163 (77), 105 (85), 91 (100); HRMS (EI) m/z calcd for C₂₀H₂₈N₆O 368.2325, found 368.2308.

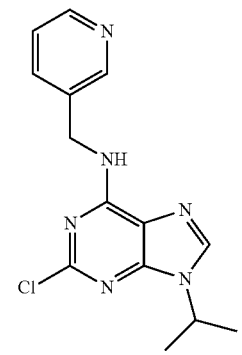

16r

2-Chloro-9-isopropyl-N-(pyridin-3-ylmethyl)-9H-purin-6-amine (16r). To a solution of 15c (99.0 mg, 0.423 mmol) in n-BuOH (1.5 mL) were added 3-pyridinemethanamine (55.6 mg, 0.514 mmol) and Et₃N (70.1 mg, 0.685 mmol). The reaction mixture was heated under microwave irradiation at 120° C. for 20 min n-BuOH was evaporated in vacuo. The residue was diluted with water (5.0 mL) and extracted with EtOAc (3×7.0 mL). The combined organic extracts were dried (MgSO$_4$), filtered, and concentrated to yield a pale yellow solid. The solid residue was resuspended (hexanes/Et$_2$O, 2:1), filtered, and the solid was rinsed (hexanes/Et$_2$O, 3:1). The filtered solid was dried under high-vacuum to yield 16r (112.0 mg, 0.389 mmol, 86%) as a pale yellow solid: $^1$H NMR (CDCl$_3$, 300 MHz) δ 8.65 (s, 1 H), 8.54 (dd, 2 H, J=1.2, 4.5 Hz), 7.73-7.70 (m, 1H), 7.28-7.23 (m, 1 H), 6.62 (bs, 1 H), 5.00-4.75 (m, 2 H), 4.83 (hept, 1 H, J=6.9 Hz), 1.57 (d, 6H, J=6.6 Hz).

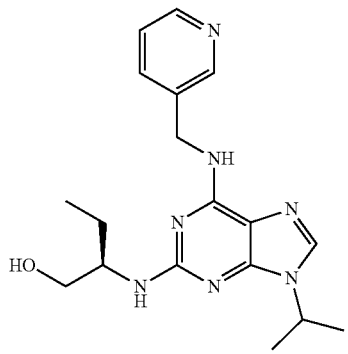

13r (R)-2-(9-Isopropyl-6-(pyridin-3-ylmethylamino)-9H-purin-2-ylamino)butan-1-ol (13r). A mixture of 16r (50.0 mg, 0.165 mmol) and (R)-(-)-2-amino-1-butanol (73.6 mg, 0.826 mmol) was heated in a microwave vial immersed in an oil bath at 170° C. for 15 h. The reaction mixture was cooled to room temperature, diluted with water (5.0 mL), and extracted with EtOAc (4×10 mL). The combined organic phases were washed with warm water (50-55° C., 2×5 mL), dried (MgSO$_4$), filtered, concentrated, and dried under high-vacuum overnight to yield a yellow oil. The oil was dissolved in EtOAc and Et$_2$O, and upon drop-wise addition of hexanes an off-white solid precipitated. The solid was rinsed (Et$_2$O/hexanes, 2:1, 3x) by pipetting out the supernatant. After drying the solid under high-vacuum, 13r (35.9 mg, 0.101 mmol, 61%) was obtained as a colorless amorphous solid: IR (ATR) 3252, 3217, 3211, 3205, 3123, 2974, 1616, 1580, 1569, 1457, 1444, 1347, 1308, 1292, 1221, 1198, 1059, 745, 727 cm$^{-1}$; $^1$H NMR (CDCl$_3$, 300 MHz) δ 8.60 (d, 1 H, J=1.5 Hz), 8.48 (dd, 1 H, J=1.2, 4.5 Hz), 7.70-7.65 (m, 1 H), 7.507.44 (m, 1 H), 7.20 (dd, 1 H, J=4.8 Hz, 7.8 Hz), 6.57 (bs, 1 H), 4.98-4.95 (m, 1 H), 4.804.70 (m, 2 H), 4.58 (hept, 1 H, J=6.9 Hz), 3.91-3.86 (m, 1 H), 3.77 (dd, 1 H, J=3.0, 7.8 Hz), 3.61 (dd, 2 H, J=7.2, 10.8 Hz), 1.75-1.40 (m, 2H), 1.50 (d, 6 H, J=6.6 Hz), 0.97 (t, 3 H, J=7.5 Hz).

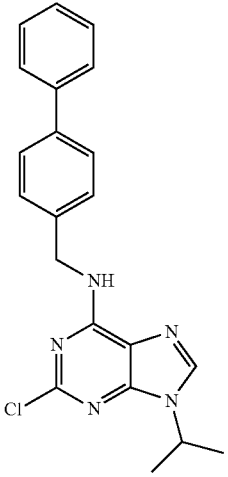

16s

N-(Biphenyl-4-ylmethyl)-2-chloro-9-isopropyl-9 H-purin-6-amine (16s). To a solution of 15c (150.0 mg, 0.649 mmol) in n-BuOH (1.5 mL) were added 4-phenylbenzylamine (0.125 0.682 mmol) and triethylamine (108.0 mg, 1.06 mmol) under an N$_2$ atmosphere. The reaction mixture was heated under microwave irradiation at 120° C. for 20 min. n-BuOH was evaporated, and the residue was dissolved in EtOAc and washed with water. The aqueous phase was further extracted with EtOAC, and the combined organic extracts were dried (MgSO$_4$) and concentrated to yield a colorless solid. The solid was resuspended (hexanes/Et$_2$O, 3:1), filtered, and rinsed (hexanes/Et$_2$O, 3:1). The solid was dried under high-vacuum to yield 16s (187.0 mg, 0.495 mmol, 76%) as an off-white solid: Mp 98-100° C.; IR (ATR, neat) 1615, 1571, 1350, 1308 cm$^{-1}$; $^1$H NMR (CDCl$_3$, 600 MHz) δ 7.68 (bs, 1 H), 7.61-7.57 (rm 4 H), 7.487.42 (m, 4 H), 7.36 (L 1 H J=7.8 Hz), 6.55 (bs, 1H), 4.88 (bs, 2 H), 4.82 (hept, 1 H, J=6.6 Hz), 1.56 (d, 6 H, J=6.6 Hz); $^{13}$C NMR (CDCl$_3$, 150 MHz) δ 155.1, 154.3, 149.8, 140.6, 137.7, 137.0, 128.8, 128.4, 127.4, 127.3, 127.1, 118.9, 46.9, 44.3, 22.8; HRMS (ES) m/z calcd for C$_{21}$H$_{20}$ClN$_5$ [M+Na]$^+$ 400.1305, found 400.1308.

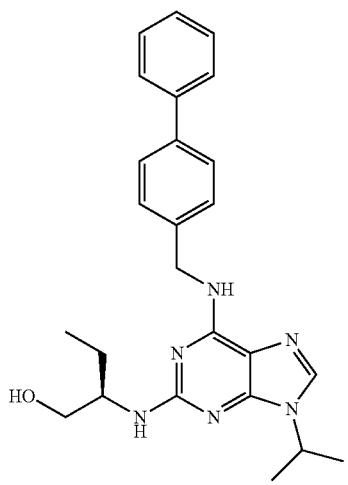

13s (R)-2-(6-(Biphenyl-4-ylmethylamino)-9-isopropyl-9H-purin-2-ylamino)butan-1-ol (13s). A mixture of 16s (32.0 mg, 0.0821 mmol), potassium fluoride (1.50 mg, 0.0258 mmol), and (R)-(−)-2-amino-1-butanol (61.8 mg, 0.651 mmol) was heated in a microwave vial immersed in an oil bath at 170° C. for 12 h. The reaction mixture was cooled to room temperature, diluted with water, and extracted with EtOAc (4×). The combined organic phases were washed with warm water (50-55° C., 2×), dried (MgSO$_4$), filtered, concentrated, and dried under high-vacuum at 70° C. (oil bath) for 2 h to yield an amorphous yellow semi-solid. After addition of Et$_2$O, the product was precipitated from the solution by drop-wise addition of hexanes (added in a minimal amount to achieve a homogeneous mixture). The solid was rinsed (Et$_2$O/hexanes, 2:1) by pipetting out the supernatant. The solid was dried under high-vacuum at 40° C. overnight (to eliminate a volatile impurity, ~0.9 ppm) to obtain 13s (25 mg, 0.0581 mmol, 71%) as a light yellow solid: Mp 116-119° C.; IR (ATR, neat) 3265, 1600, 1542, 1485 cm$^{-1}$; $^1$H NMR (CDCl$_3$, 600 MHz) δ 7.60-7.52 (m, 4H), 7.46-7.39 (m, 5 H), 7.34 (t, 1 H, J=7.8 Hz), 6.52 (bs, 1 H), 4.97 (s, 1 H), 4.80 (bs, 2 H), 4.59 (hept, 1 H, J=6.6 Hz), 3.96-3.88 (m, 1 H), 3.83 (dd, 1 H, J=10.8, 2.4 Hz), 3.51 (dd, 1 H, J=10.8, 7.8 Hz), 1.68-1.50 (m, 2 H), 1.51 (d, 6 H, J=6.6 Hz), 1.02 (t, 3 H, J=7.8 Hz); $^{13}$C NMR (CDCl$_3$, 150 MHz) δ 160.0, 154.8, 150.1, 140.8, 140.2, 138.0, 134.5, 128.7, 128.1, 127.3, 127.2, 127.0, 114.6, 68.3, 56.2, 46.4, 44.0, 25.0, 22.5, 22.4, 10.9; HRMS (ES) m/z calcd for C$_{25}$H$_{30}$N$_6$O [M+H]$^+$ 431.2559, found 431.2538.

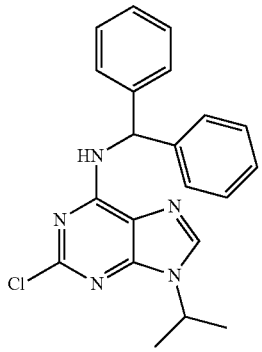

16t

N-Benzhydryl-2-chloro-9-isopropyl-9H-purin-6-amine (16t). To a solution of 15c (100.0 mg, 0.433 mmol) in n-BuOH (1.5 mL) were added diphenylamine (95.2 mg, 0.519 mmol) and Et$_3$N (70.8 mg, 0.692 mmol). The reaction mixture was heated under microwave irradiation at 120° C. for 20 min n-BuOH was evaporated in vacuo, and the residue was diluted with water (5.0 mL), and extracted with EtOAc (3×7.0 mL). The combined organic extracts were dried (MgSO4), filtered, and concentrated to yield a pale yellow solid that was resuspended (hexanes/Et$_2$O, 2:1), filtered, and washed hexanes/Et$_2$O, 3:1). The filtrate was dried under high-vacuum to obtain 16t (117 mg, 0.310 mmol, 72%) as a pale yellow solid: Mp 191.1-193.2° C.; IR (ATR) 3252, 3217, 3211, 3205, 3123, 2974, 1616, 1580, 1569, 1457, 1444, 1347, 1308, 1292, 1221, 1198, 1059, 745, 727 cm$^{-1}$; $^1$H NMR (CDCl$_3$, 300 MHz) δ 7.63 (bs, 1 H), 7.32-7.26 (m, 10 H), 6.76 (bs, 1 H), 4.80 (hept, 1 H, J=6.6 Hz), 1.55 (d, 6 H, J=6.9 Hz); $^{13}$C NMR (CDCl$_3$, 75 MHz) δ 154.4, 150.0, 141.5, 137.9, 128.8, 127.7, 127.5, 127.2, 118.8, 57.3, 46.9, 22.8; EIMS m/z 377 (M+, 98), 379 (35), 334 (25), 182 (44), 167 (100), 165 (61); HRMS (EI) m/z calcd for C$_{21}$H$_{20}$ClN$_5$ 377.1407, found 377.1400.

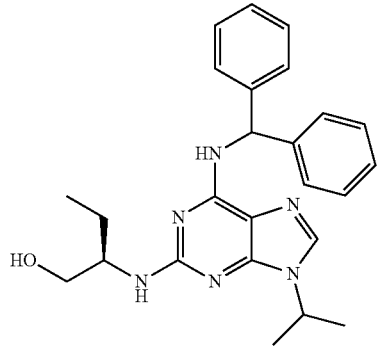

13t (R)-2-(6-(Benzhydrylamino)-9-isopropyl-9H-purin-2-ylamino)butan-1-ol (13t). A mixture of 16t (50.0 mg, 0.132 mmol) and (R)-(−)-2-amino-1-butanol (87.5 mg, 0.981 mmol) was heated in a microwave vial immersed in an oil bath at 170° C. for 15 h. The reaction mixture was cooled to room temperature, diluted with water (5.0 mL), and extracted with EtOAc (4×10.0 mL). The combined organic layers were washed with warm water (50-55° C., 2×5.0 mL), dried (MgSO$_4$), filtered, concentrated, and dried under high-vacuum overnight to obtain a yellow oil. The oil was dissolved in EtOAc, resuspended in Et$_2$O, and hexanes was added drop-wise to achieve a homogeneous supernatant. An off-white solid precipitated from the solution, and the solid was rinsed (Et$_2$O/hexanes, 2:1) by pipetting out the supernatant and dried under high-vacuum to obtain 13t (36.4 mg, 0.0845 mmol, 64%) as an off-white solid: Mp 72.2-75.0° C.; IR (ATR) 3286, 3086, 3068, 3055, 3038, 3030, 1647, 1627, 1592, 1575, 1560, 1446, 1314, 1273, 1204, 1174, 1159, 1150, 1075, 1027, 997, 943, 936, 917, 865, 813, 764, 719, 701, 691 cm$^{-1}$; $^1$H NMR (CDCl$_3$, 300 MHz): δ 7.46 (s, 1 H), 7.34-7.26 (m, 10 H), 6.53 (bs, 1 H), 6.41 (bs, 1 H), 4.81 (d, 1 H, J=5.1 Hz), 4.59 (hept, 1 H, J=6.6 Hz), 3.78-3.70 (m, 2 H), 3.57-3.51 (dd, 2 H, J=7.5, 9.9 Hz), 1.6-1.3 (m, 2 H), 1.51 (d, 6 H, J=6.6 Hz), 0.96 (t, 3 H, J=7.5 Hz); $^{13}$C NMR (CDCl$_3$, 75 MHz) δ 159.9, 153.9, 142.2, 134.6, 128.5, 127.6, 127.3, 114.6, 67.9, 57.9, 56.1, 46.4, 24.9, 22.6, 10.9; EIMS m/z 430 (M$^+$, 89), 400 (78), 399 (100), 358 (36), 168 (63), 165 (91), 152 (59); HRMS (EI) m/z calcd for C$_{25}$H$_{30}$N$_6$O 430.2481, found 430.2486.

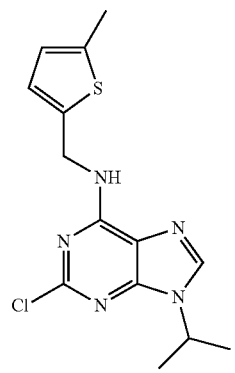

16u

2-Chloro-9-isopropyl-N-((5-methylthiophen-2-yl)methyl)-9H-purin-6-amine (16u). To a solution of 15c (74.4 mg, 0.322 mmol) in n-BuOH (1.25 mL) was added (5-methylthien-2-yl)methylamine·HCl (55.7 mg, 0.340 mmol) and freshly distilled Et₃N (98.0 mg, 0.969 mmol) under an N₂ atmosphere. The reaction mixture was subjected to microwave irradiation at 120° C. for 30 min. White crystals were observed upon completion of the heating. n-BuOH was evaporated in vacuo, and the residue was dissolved in EtOAc (20.0 mL) and deionized water (10.0 mL). The aqueous phase was further extracted with EtOAc (3×10.0 mL), and the combined organic layers were dried (MgSO₄), filtered, and concentrated to yield a light yellow solid. The solid was resuspended (hexanes/Et₂O, 3:1), and the precipitated solid was filtered through a fritted funnel and dried under high-vacuum overnight to obtain 16u (96.9 mg, 0.301 mmol, 94%) as light yellow amorphous solid: IR (ATR, neat) 3340, 3256, 3213, 3184, 3137, 3120, 3064, 2977, 2967, 2921, 1705, 1676, 1620, 1569, 1538, 1463, 1351, 1310, 1290, 1256, 1224, 1200, 1159, 1098, 1070, 1036, 1010, 969, 956, 798, 787, 761, 736, 725, 695, 678, 658 cm⁻¹; ¹H NMR (300 MHz, CDCl₃) δ 7.77 (bs, 1 H), 6.85 (d, 1 H, J=3.3 Hz), 6.60 (d, 1 H, J=3.3 Hz), 6.25 (bs, 1 H), 4.89 (bs, 2 H), 4.83 (sept, 1 H, J=6.7 Hz), 2.45 (s, 3 H), 1.58 (d, 6 H, J=6.6 Hz); ¹³C NMR (75 MHz, CDCl₃) δ 154.8, 154.2, 149.9, 139.9, 138.5, 137.8, 126.0, 124.7, 118.8, 46.9, 39.6, 22.8, 15.4; HRMS (ES) m/z calcd for C₁₄H₁₆N₅SCl 321.0850, found 321.0813.

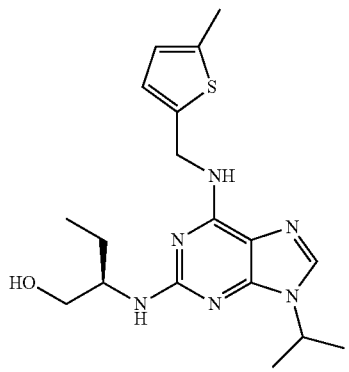

13u (R)-2-(9-Isopropyl-6-((5-methylthiophen-2-yl)methylamino)-9H-purin-2-ylamino)butan-1-ol (13u). A mixture of 16u (65.3 mg, 0.203 mmol) and (R)-2-aminobutan-1-ol (96.2 mg, 101 µL, 1.01 mmol, 5 equiv) were heated in a microwave vial immersed in an oil bath at 170° C. for 8 h. The reaction mixture was cooled to room temperature, diluted with water (15 mL), and extracted with EtOAc (3×20.0 mL). The combined organic phases were washed with warm water (2×10.0 mL, 50-55° C.), dried (MgSO₄), filtered, concentrated, and dried under high-vacuum at 50° C. (oil bath) for 2 h to yield a yellow solid. The crude residue was purified by chromatography on SiO₂ (hexanes/EtOAc, 9:1) to yield 13u (61.8 mg, 0.165 mmol, 81%) as a light yellow foam: IR (ATR, neat) 3341, 3272, 3121, 2964, 2925, 2052, 2185, 1681, 1605, 1544, 1512, 1493, 1456, 1380, 1311, 1253, 1202, 1161, 1102, 1042, 1025, 971, 904, 861, 800, 755, 727, 723, 694, 675 cm⁻¹; ¹H NMR (400 MHz, CDCl₃) δ 7.47 (s, 1 H), 6.79 (d, 1 H, J=3.6 Hz), 6.58-6.56 (m, 1 H), 5.98 (bs, 1 H), 5.25-5.00 (b, 1 H), 4.90 (app d, 1 H, J=5.6 Hz), 4.82 (bs, 1 H), 4.59 (sept, 1 H, J=6.8 Hz), 3.96-3.88 (m, 1 H), 3.84 (dd, 1 H, J=10.4, 2.0 Hz), 3.65 (dd, 1 H, J=10.8, 8.0 Hz), 2.42 (s, 3 H), 1.70-1.50 (m, 2 H), 1.52 (d, 6 H, J=6.8 Hz), 1.04 (t, 3 H, J=7.6 Hz); ¹³C NMR (100 MHz, CDCl₃) δ 160.0, 154.4, 150.4, 139.7, 139.0, 134.6, 125.8, 124.7, 114.7, 68.6, 56.4, 46.5, 39.7, 29.7, 25.0, 22.6, 15.4, 11.0; HRMS (ESI) m/z calcd for C₁₈H₂₇N₆OS [M+Na]⁺ 397.1767, found 397.1787.

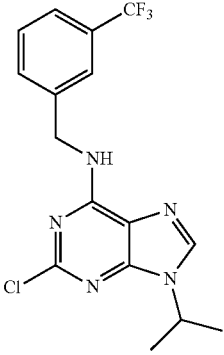

16v

2-Chloro-9-isopropyl-N-(3-(trifluoromethyl)benzyl)-9H-purin-6-amine (16v). To a solution of 15c (65.8 mg, 0.273 mmol) in n-BuOH (1.0 mL) were added 3-(trifluoromethyl)benzylamine (52.4 mg, 0.300 mmol) and Et₃N (46.1 mg, 0.456 mmol) under a nitrogen atmosphere. The reaction mixture was heated with microwave irradiation at 120° C. for 30 min. The n-BuOH was evaporated, and the residue was dissolved in EtOAc (20.0 mL) and washed with water (10.0 mL). The aqueous phase was further extracted with EtOAc (2×10.0 mL), and the combined organic extracts were dried (MgSO₄), filtered, and concentrated to yield a colorless solid. The solid was resuspended (hexanes/Et₂O, 3:1), filtered, washed (hexanes/Et₂O, 3:1), and dried under high-vacuum to yield 16v (63.0 mg, 0.170 mmol, 60%) as a colorless amorphous solid: IR (ATR, neat) 3250, 3150, 2990, 2925, 1625, 1446, 1313, 1230, 1159, 1140, 1099, 980, 930, 700 cm⁻¹; ¹H NMR (300 MHz, CDCl₃) δ 7.77 (s, 1 H), 7.63 (s, 1 H), 7.59 (d, 1 H, J=7.5 Hz), 7.56 (d, 1 H, J=7.8 Hz), 7.47 (t, 1 H, J=7.5 Hz), 6.33 (bs, 1 H), 4.90 (bs, 2 H), 4.83 (sept, 1 H, J=6.8 Hz), 1.58 (d, 6H, J=6.9 Hz); ¹³C NMR (75 MHz, CDCl₃) δ 155.1, 154.2, 150.0, 139.4, 137.8, 131.2, 130.9 (q, J=32.2 Hz), 129.3, 124.4, 124.3, 124.0 (q, J=270.1 Hz), 118.8, 47.0, 43.9, 22.7; HRMS [EI] m/z calcd for [C₁₆H₁₅ClF₃N₅] 369.0968, found 369.9640.

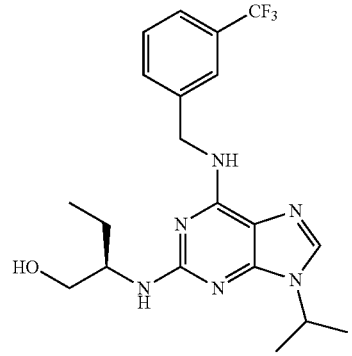

13v (R)-2-(9-Isopropyl-6-(3-(trifluoromethyl)benzylamino)-9H-purin-2-ylamino)butan-1-ol (13v). A mixture of 16v (56.2 mg, 0.152 mmol) and (R)-(−)-2-aminobutan-1-ol (95.0 mg, 1.07 mmol) was heated in a microwave vial immersed in an oil bath at 170° C. for 8 h. The reaction mixture was cooled to room temperature, diluted with water (10.0 mL), and extracted with EtOAc (2×15.0 mL). The combined organic phases were washed with warm water (2×5.0 mL, 50-55° C.), dried (MgSO$_4$), filtered, concentrated, and dried under high-vacuum at 50° C. (oil bath temperature) for 2 h to yield a yellow solid. After addition of Et$_2$O, an off-white solid precipitated. The solid was rinsed (Et$_2$O, 3×) by pipetting out the supernatant and dried under high-vacuum overnight at 40° C. to yield 13v (16.1 mg, 0.0381 mmol, 25%) as a colorless amorphous solid: Mp 149.9-153.6° C.; IR (ATR, neat) 3254, 3059, 2934, 1621, 1599, 1535, 1323, 1260, 1161, 1118, 1062, 797, 701 cm$^{-1}$; $^1$H NMR (300 MHz, CDCl$_3$) δ 7.77 (s, 1 H), 7.58-7.51 (m, 3 H), 7.44 (t, 1 H, J=7.5 Hz), 6.22 (bs, 1H), 4.89 (d, 1 H, J=5.7 Hz), 4.83 (bs, 2 H), 4.62 (sept, 1 H, J=6.8 Hz), 3.95-3.80 (m, 1 H), 3.82 (dd, 1 H, J=2.7, 10.5 Hz), 3.63 (dd, 1 H, J=7.5, 10.5 Hz), 1.70-1.40 (m, 2 H), 1.54 (d, 6 H, J=6.9 Hz), 1.01 (t, 3 H, J=7.5 Hz); $^{13}$C NMR (175 MHz, CDCl$_3$) δ 159.9, 154.6, 150.3, 140.0, 134.7, 130.9, 130.8 (q, J=31.5 Hz), 129.0, 124.4 (q, J=3.5 Hz), 124.1 (q, J=3.5 Hz), 124.1 (q, J=271.3 Hz), 114.5, 68.2, 56.2, 46.5, 43.8, 24.9, 22.5 (2C), 10.8; HRMS (ES) m/z calcd for C$_{20}$H$_{26}$F$_3$N$_6$O [M+H]$^+$ 423.2120, found 423.2103.

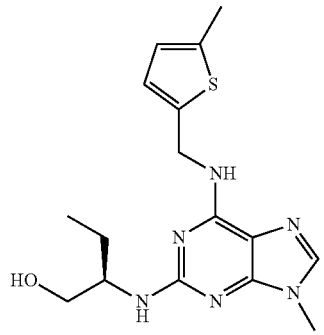

16w

2-Chloro-9-methyl-N-[(5-methylthiophen-2-yl)methyl]-9H-purin-6-amine (16w). To a solution of 15b (30.0 mg, 0.148 mmol, 1 eq) in dry n-BuOH (0.6 mL, 0.25 M) were added (5-methylthien-2-yl)methylamine.HCl (25.4 mg, 0.155 mmol, 1.05 eq) and freshly distilled triethylamine (44.9 mg, 0.443 mmol, 3 eq, 0.06 mL) under nitrogen. The reaction mixture was subjected to microwave irradiation at 120° C. for 35 min The n-BuOH was evaporated, and the residue was dissolved in EtOAc (20 mL) and deionized water (10 mL). The layers were separated and the aqueous layer was further extracted with EtOAc (3×10 mL). The combined organic layers were dried (MgSO$_4$) and concentrated under reduced pressure to yield a yellow solid. The solid was washed with Et$_2$O and dried under high-vacuum to yield 16w (37.5 mg, 0.128 mmol, 86%) as a light yellow solid: Mp 217.5-219.6° C.; IR (ATR, neat) 3058, 1607, 1575, 1340, 1303, 1232, 1094, 917, 796, 693 cm$^{-1}$; $^1$H NMR (400 MHz, DMSO-d$_6$) δ 8.76 (bs, 1 H), 8.11 (s, 1 H), 6.79 (d, 1 H, J=3.3 Hz), 6.60 (app d, 1H, J=2.2 Hz), 4.68 (d, 2 H, J=5.6 Hz), 3.69 (s, 3 H), 2.34 (s, 3 H); $^{13}$C NMR (100 MHz, DMSO-d$_6$) δ 154.4, 152.9, 150.4, 142.1, 139.6, 138.4, 125.7, 124.6, 118.1, 38.5, 29.6, 14.9; HRMS (ES) m/z calcd for C$_{12}$H$_{11}$N$_5$SCl [M−H]$^+$ 292.0424, found 292.0428.

13w (2R)-2-[(9-Methyl-6-{[(5-methylthiophen-2-yl)methyl]amino}-9H-purin-2-yl)amino]butan-1-ol (13w). A mixture of 16w (18.2 mg, 0.0620 mmol, 1 eq) and 2-amino-1-butanol (27.6 mg, 0.029 mL, 0.276 mmol, 5 eq) was heated in a sealed vial in an oil bath at 170° C. for 15 h. The reaction mixture was cooled at room temperature, treated with water (15 mL) and then extracted with EtOAc (3×20 mL). The combined organic layers were washed with warm water (2×10 mL, 50-55° C.), dried (MgSO$_4$), filtered and concentrated. Purification by chromatography on SiO$_2$ (EtOAc/MeOH/Et$_3$N, 94:5:1) gave a yellow oil which was dried under high-vacuum at 50° C. for 2 h to yield 13w (20.0 mg, 0.0577 mmol, 93%) as a yellow oil which solidified to a dark yellow solid: Mp 56.4-58.3° C.; IR (ATR, neat) 2934, 1601, 1545, 1512, 1415, 1215, 785 cm$^{-1}$; $^1$H NMR (400 MHz, CDCl$_3$) δ 7.35 (s, 1 H), 6.77 (d, 1 H, J=3.2 Hz), 6.55 (app d, 1 H, J=2.3 Hz), 6.20 (bs, 1 H), 4.97 (d, 1 H, J=6.1 Hz), 4.80 (bs, 2 H), 3.95 (app pent, 1 H, J=5.8 Hz), 3.82 (dd, 1 H, J=10.7, 2.6 Hz), 3.63 (dd, 1 H, J=10.7, 7.5 Hz), 3.61 (s, 3 H), 2.41 (s, 3 H), 1.66-1.52 (m, 2 H), 1.02 (t, 3 H, J=7.4 Hz); $^{13}$C NMR (100 MHz, CDCl$_3$) δ 160.2, 154.3, 151.1, 139.5, 139.1, 137.6, 125.7, 124.6, 114.1, 67.9, 56.0, 39.5, 29.3, 25.0, 15.3, 10.9; HRMS (ES) m/z calcd for C$_{16}$H$_{23}$N$_6$OS [M+H]$^+$ 347.1654, found 347.1659.

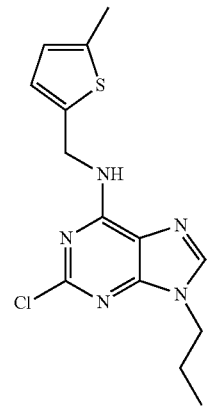

16x

2-Chloro-N-[(5-methylthiophen-2-yl)methyl]-9-propyl-9H-purin-6-amine (16x). To a solution of 15a (33.9 mg, 0.147 mmol, 1 eq.) in n-BuOH (0.6 mL, 0.25 M) were added (5-methylthien-2-yl)methylamine·HCl (25.2 mg, 0.153 mmol, 1.05 eq.) and freshly distilled triethylamine (44.5 mg, 0.440 mmol, 3.00 equiv). The reaction mixture was subjected to microwave irradiation at 120° C. for 30 min. The residue was dissolved in EtOAc (20 mL) and deionized water (10 mL). The aqueous phase was further extracted with EtOAc (3×10 mL), and the combined organic layers were dried (MgSO$_4$), filtered and concentrated under reduced pressure. Purification on SiO$_2$ (EtOAc/hexanes, 1:1) gave 16x (42.1 mg, 0.131 mmol, 89%) as a colorless solid: Mp 150.3-151.4° C.; IR (ATR, neat) 3256, 3208, 2994, 2872, 1616, 1573, 1538, 1472, 1303, 1251, 1219, 1085, 811 cm$^{-1}$; $^1$H NMR (400 MHz, CDCl$_3$) δ 7.57 (bs, 1 H), 6.80 (d, 1 H, J=3.3 Hz), 6.75 (bs, 1 H), 6.57 (app dd, 1 H, J=3.3, 1.0 Hz), 4.87 (bs, 2 H), 4.09 (t, 2 H, J=7.2 Hz), 2.42 (s, 3 H), 1.88 (sext, 2H, J=7.4 Hz), 0.94 (t, 3 H, J=7.4 Hz); $^{13}$C NMR (100 MHz, CDCl$_3$) δ 154.8, 154.5, 150.5, 140.4, 140.2, 138.1, 126.4, 124.9, 118.7, 45.6, 39.8, 23.5, 15.5, 11.2; HRMS (ES) m/z calcd for C$_{14}$H$_{17}$N$_5$SCl [M+H]$^+$ 322.0893, found 322.0890.

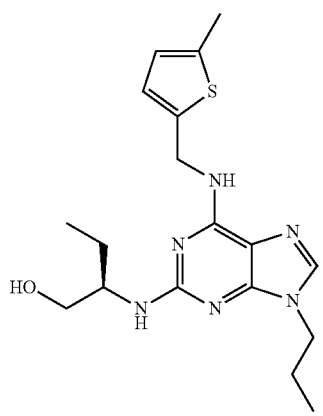

13x (2R)-2-[(6-{[(5-Methylthiophen-2-yl)methyl]amino}-9-propyl-9H-purin-2-yl)amino]butan-1-ol (13x). A mixture of 16x (20.0 mg, 0.0621 mmol, 1 equiv) and (R)-(−)2-amino-1-butanol (27.7 mg, 0.311 mmol, 5 equiv) was heated in a sealed vial in an oil bath at 170° C. for 15 h. The reaction mixture was cooled to room temperature and water was added (15 mL). The mixture was extracted with EtOAc (3×20 mL), dried (MgSO$_4$), filtered and concentrated. Purification by chromatography on SiO$_2$ (EtOAc/MeOH, 98:2) provided 13x (21.2 mg, 0.0566 mmol, 91%) as a colorless solid: Mp 124.8-129.6° C.; IR (ATR, neat) 3418, 3374, 3260, 2958, 1605, 1512, 1402, 1333, 1215, 798, 796, 783 cm$^{-1}$; $^1$H NMR (400 MHz, CDCl$_3$) δ 7.40 (s, 1 H), 6.79 (d, 1 H, J=3.4 Hz), 6.57-6.56 (m, 1 H), 6.04 (bs, 1 H), 4.96 (app d, 1 H, J=5.5 Hz), 4.82 (bs, 2 H), 3.97-3.88 (m, 3 H), 3.83 (dd, 1 H, J=10.7, 2.5 Hz), 3.64 (dd, 1 H, J=10.7, 7.7 Hz), 2.42 (s, 3 H), 1.84 (sext, 2H, J=7.2 Hz), 1.70-1.51 (m, 2 H), 1.03 (t, 3 H, J=7.4 Hz), 0.93 (t, 3 H, J=7.2 Hz); $^{13}$C NMR (100 MHz, CDCl$_3$) δ 160.1, 154.4, 151.0, 139.8, 139.1, 137.4, 126.0, 124.8, 114.5, 68.6, 56.5, 45.2, 39.7, 25.2, 23.3, 15.5, 11.3, 11.1; HRMS (ES) m/z calcd for C$_{18}$H$_{27}$N$_6$OS [M+H]+ 375.1967, found 375.1968.

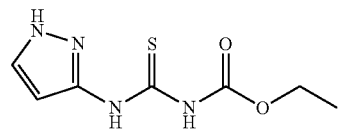

1

N-Ethoxycarbonyl-N'-(pyrazol-3-yl)thiourea(1). A solution of 1 H-pyrazol-3-amine (2.731 g, 32.54 mmol, 1.130 eq) in THF (37 mL) was cooled to 0° C. under nitrogen. In a dropwise fashion, ethoxycarbonyl isothiocyanate (3.5 mL, 28 mmol, 1.0 eq) was added to the mixture over approximately 5 min. The reaction mixture was allowed to stir for 1 h at 0° C. Solvent was then removed in vacuo to give 1 as a yellow solid (7.20 g, 28.2 mmol, 98%). This compound was used in the next step without further purification: 1 H NMR (CDCl 3, 300 MHz) δ 1.34 (t, 3 H, J=7.1 Hz), 4.30 (q, 2 H, J=7.1 Hz), 7.04 (d, 2 H, J=2.4 Hz), 7.55 (d, 2 H, J=2.4 Hz), 8.28 (s, 1 H,), 11.9 (s, 1 H).

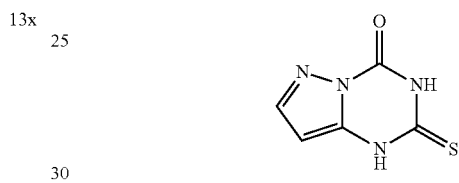

2

2-Thioxo-2,3-dihydropyrazolo[1,5-a][1,3,5]triazin-4 (1H)-one (2). A solution of 1 (494 mg, 2.30 mmol, 1.00 eq) in 2 N NaOH (4.8 mL, 10 mmol, 4.2 eq) was stirred at room temperature for 2 h. The reaction mixture was cooled in an ice bath and in a dropwise fashion, 2 N H$_2$SO$_4$ (6.9 mL, 13 mmol, 6.0 eq,) was added. The resulting precipitate was collected by vacuum filtration, washed with water, and dried under vacuum to give 2 as an off white powder (337 mg, 2.01 mmol, 87%). This compound was used in the next step without further purification: $^1$H NMR (DMSO-d$_6$, 300 MHz) δ 2.50 (s, 3 H), 5.88 (d, 1 H, J=1.5 MHz), 7.86 (d, 1 H, J=1.8 MHz), 12.78 (broad s, 1 H), 13.44 (broad s, 1 H).

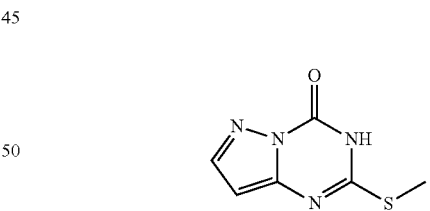

3

2-(Methylthio)pyrazolo[1,5-a][1,3,5]triazin-4(3H)-one (3). To a solution of 2 (4.97 g, 24.2 mmol, 1.00 eq.) in EtOH (97 mL) was added aqueous 2 N NaOH (25 mL, 70 mmol, 2.0 eq.) and methyl iodide (1.51 mL, 24.2 mmol, 1.00 eq.). The slurry was stirred at room temperature for 1.5 h. The reaction was then filtered and the solid was dissolved in water (246 mL). Then 2 N H2SO4 was added (14 mL, 28 mmol, 1.2 eq.) and the resulting solid filtered, washed with water, and dried under high vacuum at 60° C. for 5 h to give 3 as a white solid (3.15 g, 14.7 mmol, 60%). This compound was used in the next step without further purification: 1 H NMR (DMSO-d6, 400 MHz) δ 2.53 (s, 3 H), 6.35 (d, 1 H, J=2.0 Hz), 7.97 (d, 1 H, J=1.6 Hz), 12.89 (s, 1 H).

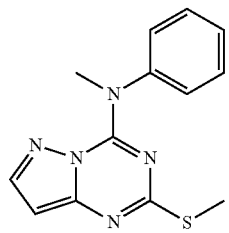

N-Methyl-2-(methylthio)-N-phenylpyrazolo[1,5-a][1,3,5]triazin-4-amine (4). To a flame dried round bottom flask was added 3 (497 mg, 2.73 mmol, 1.00 eq.), POCl3 (8.1 mL, 87 mmol, 32 eq.), and DMAP (1181 mg, 9.67 mmol, 3.548 eq.).

The mixture was then heated at reflux for 3.5 h. Excess POCl3 was removed under reduced pressure and the resulting light brown residue dried under high vacuum overnight. The solid was dissolved in dichloromethane (21 mL), placed under nitrogen, and cooled to 0° C. Triethylamine (2.40 mL, 17.2 mmol 6.31 eq.) and N-methylaniline (1.67 mL, 14.9 mmol, 5.47 eq.) were added and, after 10 min, the reaction was allowed to warm to room temperature and stirred for 7 h. The mixture was then diluted with dichloromethane (5 mL), washed with water (4×8 mL), extracted once with dichloromethane (10 mL), rinsed with brine (8 mL) and dried (MgSO4). After concentration, the residue was purified by chromatography on silica gel (3:2, hexanes: dichloromethane, then dichloromethane) to give 4 as a off white solid (564 mg, 1.91 mmol, 70%): 1 H NMR (CDCl3, 400 MHz) δ 2.53, (s, 3 H), 3.73 (s, 3 H), 6.5 (d, 1 H, J=2.0 Hz), 7.17-7.19 (m, 2 H), 7.36-7.41(m, 3 H), 7.64, (d, 1 H, J=2.4 Hz).

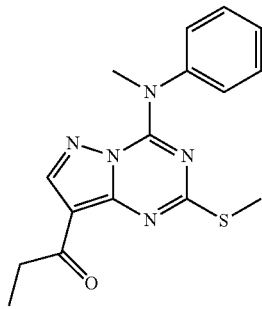

1-(4-(Methyl(phenyl)amino)-2-(methylthio)pyrazolo[1,5-a][1,3,5]triazin-8-yl)propan-1-one (5). To an oven dried vial was added 4 (587 mg, 2.07 mmol, 1.00 eq.), propionyl chloride (0.36 mL, 4.1 mmol, 2.0 eq.) and 1M tin(IV) chloride in dichloromethane (10 mL, 10 mmol, 5.0 eq.). The vial was sealed and allowed to heat at 85° C. for 17 h. The reaction mixture was then poured over crushed ice, diluted with water (10 mL) and dichloromethane (5 mL) and allowed to stir for 15 min. The layers were separated, the aqueous layers extracted with dichloromethane (10 mL), the combined organic fractions washed with water and brine (10 mL each), and dried (MgSO4). Following concentration, the crude residue was purified by chromatography on silica gel (98:2 dicloromethane:ethyl acetate) to give 5 as a white solid (590 mg, 1.892 mmol, 83%): mp=147.6-148.2° C.; 1 H NMR (CDCl3, 300 MHz) δ 1.20 (t, 3H, J=7.4 Hz), 2.59 (s, 3 H), 3.11 (q, 2 H, J=5.5 Hz), 3.74 (s, 3 H), 7.15-7.18 (m, 2 H), 7.35-7.43 (m, 3 H), 8.09 (s, 1 H); 13C NMR (CDCl3, 100 MHz) δ 8.32, 14.37, 34.66, 42.42, 108.90, 126.11, 127.62, 129.20, 144.18, 145.65, 148.23, 151.07, 170.71, 195.46; IR v 2934, 1652, 1501 cm-1; HRMS: Calculated [M+H] for C16H17N5OS 328.12; found 328.1220.

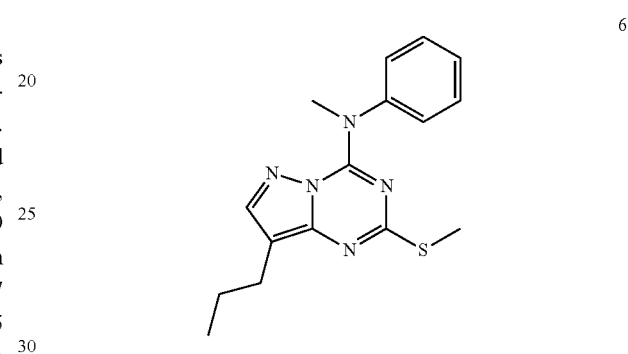

N-Methyl-2-(methylthio)-N-phenyl-8-propylpyrazolo[1,5-a][1,3,5]triazin-4-amine (6). To a solution of 5 (203 mg, 0.590 mmol, 1.00 eq) in 1:1 dichloromethane:ethanol (4 mL) at 0° C. was added LiCl (66 mg, 1.6 mmol, 2.7 eq) and NaBH4 (62 mg, 1.6 mmol, 2.7 eq). The reaction was then allowed to warm to room temperature and stirred for 15 h. A second portion of NaBH4 then was added (35 mg, 0.93 mmol, 1.6 eq.) and the reaction stirred an additional 5 h. The reaction was quenched with water (0.5 mL) and the organic solvents removed in vacuo. The residue was then diluted with dichloromethane (4 mL) and water (2 mL), extracted with dichloromethane (4 mL), washed with brine (2 mL), dried (MgSO4) and concentrated. The residue was then dissolved in dichloromethane (6 mL) and added to a solution of NaBH4 (227 mg, 5.94 mmol, 10.1 eq.) in trifluoroacetic acid (6.3 mL) at 0° C. The reaction was allowed to warm to room temperature and stirred for 4 h. The reaction was quenched with 1 M NaOH (10 mL) and diluted with dichloromethane (5 mL). The aqueous layer was then extracted with dichloromethane (3×5 mL) and the organic fractions rinsed with saturated sodium bicarbonate (2×7 mL), brine (10 mL), dried (MgSO4) and concentrated to give 6 as a yellow oil (158 mg, 448 mmol, 75%). This compound was used in the next step without further purification: 1 H NMR (CDCl3, 300 MHz) δ 0.93 (t, 3 H, J=7.4 Hz), 1.59-1.67 (m, 2 H), 2.55-2.60 (m, 5 H), 3.71 (s, 3 H), 7.15-7.18 (m, 2 H), 7.31-7.39 (m, 3 H), 7.52 (s, 1 H); 13C NMR (CDCl3, 100 MHz) δ 13.86, 14.16, 23.20, 24.50, 42.02, 107.31, 126.06, 126.91, 128.92, 144.78, 145.14, 148.27, 164.93; IR v 2954, 1534, 1508 cm-1; HRMS: Calculated [M+H] for C16H19N5S 314.14; found 314.1427.

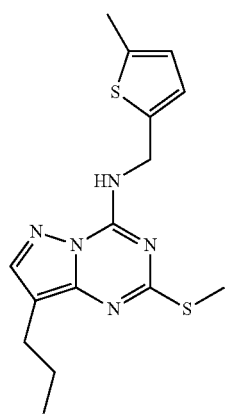

2-(Methylthio)-N-((5-methylthiophen-2-yl)methyl)-8-propylpyrazolo[1,5-a][1,3,5]triazin-4-amine (7). To a flame dried microwave vial was added mf-00521.014 (99 mg, 0.28 mmol, 1.0 eq.), triethylamine (0.78 mL, 5.6 mmol, 20 eq.), (5-methylthien-2-yl)methylamine HCl (234 mg, 1.38 mmol, 4.93 eq.), KF (21 mg, 0.36 mmol 1.3 eq), and absolute ethanol (0.93 mL). The vial was then sealed and allowed to heat at 130° C. for 36 h. The reaction mixture was then diluted with water (2 mL), extracted with dichloromethane (3×2 mL), washed with brine (2 mL), and dried (MgSO4). Following concentration, purification was performed by chromatography on silica gel (hexanes:ethyl acetate, 98:2, 95:5) to give 7 as an off white solid (47 mg, 0.13 mmol, 46%): mp=84.9-85.3° C.; 1H NMR (CDCl3, 500 MHz) δ 0.96 (t, 3 H, J=7.3 Hz), 1.65-1.72 (m,2 H), 2.45 (s, 3H), 2.45-2.63(m, 5 H), 4.86 (d, 2 H, J=5.5 Hz), 6.59 (d, 2 H, J=1.0 Hz), 6.79, (broad s, 1H), 6.59 (m, 1 H), 7.71 (s, 1 H); 13C NMR (CDCl3, 125 MHz) δ 13.86, 14.28, 15.31, 23.31, 24.58, 39.43, 108.76, 124.86, 126.85, 136.71, 140.58, 145.29, 146.22, 147.16, 166.02; IR ν 3247, 2954, 1618, 1588 cm-1; HRMS: Calculated [M+H] for C15H19N5S2 334.11; found 334.1153.

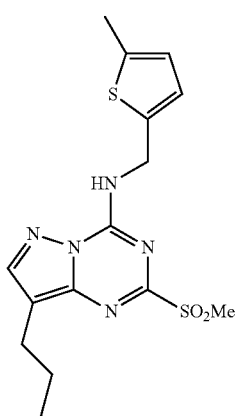

2-(Methylsulfonyl)-N-((5-methylthiophen-2-yl)methyl)-8-propylpyrazolo[1,5-a][1,3,5]triazin-4-amine (8). To a solution of 7 (47 mg, 0.0 mmol, 1.00 eq.) in acetone (2.2 mL) at 0° C. was added 3.17 M NaHCO3 (0.33 mL, 1.0 mmol, 8.0 eq.) followed by 0.39 M oxone in water (247 mg in 1.0 mL, 0.402 mmol 3.07 eq.). The slurry was then allowed to stir 16 h at room temperature. The reaction was quenched with 50% aqueous sodium bisulfite (0.16 mL), diluted with water (2 mL), extracted with dichloromethane (3×3 mL), washed with brine (3 mL), dried (MgSO4), and concentrated giving 8 as an opaque oil (48 mg, 0.12 mmol, 89%). This compound was used in the next step without further purification.

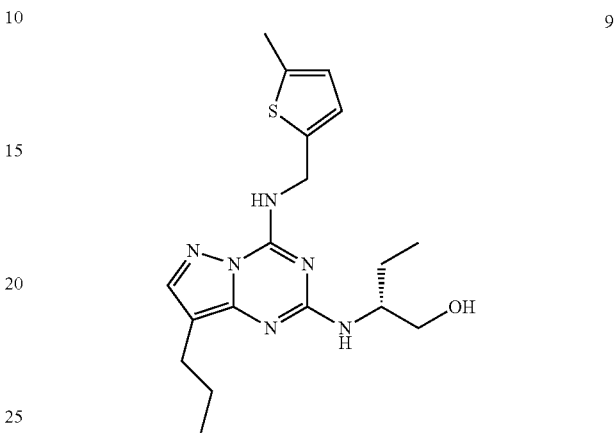

(R)-2-((4-(((5-Methylthiophen-2-yl)methyl)amino)-8-propylpyrazolo[1,5-a][1,3,5]triazin-2-yl)amino)butan-1-ol (9) (also referred to herein as compound MF-521-17). To a flame dried microwave vial was added 8 (47 mg, 0.011 mmol, 1.00 eq.), R-(−)-2-amino-1-butanol (0.056 mL, 0.57 mmol, 5.0 eq.), KF (34 mg, 0.0.57 mmol, 5.0 eq.), and 1,4 dioxane (0.31 mL). The vial was sealed and allowed to heat at 140° C. in a sand bath for 12 h. The reaction was then treated with water (2 mL), extracted with dichloromethane (2×3 mL), washed with brine (3 mL), dried (MgSO4), and concentrated. The crude mixture was then purified by chromatography on silica gel (3:1 dichloromethane:ethyl acetate) to give 9 as an off white solid (25 mg, 0.065 mmol, 57%): mp=118.3-120.1° C.; 1H NMR (CDCl3, 300 MHz) δ 0.954(t, 3 H, J=7.4 Hz),1.05 (t, 3 H, J=7.5 Hz),1.57-1.68 (m, 4 H), 2.44 (s, 3 H), 2.49 (t, 2 H, J=7.4 Hz), 3.68 (dd, 2 H, J=7.2, 10.8 Hz), 3.84 (d, 2 H, J=9.6 Hz), 3.95 (broad s, 1 H), 4.78 (d, 2 H, 6.0 Hz), 6.59 (m, 1 H), 6.70 (broad s, 1H), 6.82 (d, 1 H, J=3.3 Hz), 7.59 (s, 1 H); 13C NMR (CDCl3, 125 MHz) δ 10.80, 13.81, 15.29, 23.32, 24.52, 24.83, 39.31, 56.26, 67.90, 105.82, 124.82, 126.55, 136.96, 140.40, 145.58, 146.65, 148.44, 157.73; IR ν 3286, 2956, 2934, 1592, 1564 cm-1; HRMS: Calculated [M+H] for C18H26N6OS 375.19; found 375.1960.

EXAMPLE 1

Activity of Analogs 13a-13x tsA201 cells expressing calcium channels. Biological evaluations of the effects of (R)-roscovitine derivatives on N-type calcium channels were initially performed using a tsA201 cell line that stably expresses all of the subunits of the N-type $Ca^{2+}$ channel splice variant predominantly present in mammalian brain and spinal cord: $Ca_v2.2$ $rn\alpha_{1B-c}$ ($Ca_v2.2$ e[24a,Δ31a]), $Ca_v\beta_3$ and $Ca_v\alpha_2\delta_1$. For subsequent evaluation of effects on N-, P/Q-, or L-type channels, tsA-201 cells were transiently transfected with Cav2.2, Cav2.1, or Cav1.3, in combination with $Ca_v\beta_3$ and $Ca_v\alpha_2\delta_1$ (Addgene, Cambridge Mass.) using FuGENE 6 (Life Technologies, Grand Island, N.Y.). All cells were maintained in DMEM supplemented with 10% fetal bovine serum. For the stable cell line expressing N-type channels, 25 µg/mL zeocin, 5 µg/mL blasticidin, and 25 µg/mL hygromycin were added as selection agents.

Whole-cell patch clamp recordings of calcium current. To assess the biological effects of (R)-roscovitine derivatives, whole-cell currents through $Ca^{2+}$ channels were recorded using perforated patch methods. Briefly, the pipette solution consisted of 70 nM $Cs_2SO_4$, 60 mM CsCl, 1 mM $MgCl_2$, 10 mM 4-(2-hydroxyethyl)-1-piperazineethanesulfonic acid (HEPES) at pH 7.4. Cultured cells were bathed in a saline composed of 130 mM choline chloride (ChCl), 10 mM tetraethylammonium chloride (TEA-Cl), 2 mM $CaCl_2$, 1 mM $MgCl_2$, 10 mM HEPES, at pH 7.4. Patch pipettes were fabricated from borosilicate glass and pulled to a resistance of about 1 MΩ. Before each experiment, a stock solution consisting of 3 mg amphotericin-B dissolved into 50 µL anhydrous DMSO was made. Patch pipettes were tip-dipped into pipette solution that did not contain amphotericin-B for 5-10 seconds, and then backfilled with pipette solution that contained amphotericin-B (7 µL amphotericin-B stock solution mixed into 500 µL pipette solution, made fresh every hour). Using this approach, perforated patch access resistances were 7.41±1.75 MΩ (mean±SD, n=68). Capacitive currents and passive membrane responses to voltage commands were subtracted from the data. Currents were amplified by an Axopatch 200B amplifier, filtered at 5 KHz, and digitized at 10 KHz for subsequent analysis using pClamp software (Axon Instruments/Molecular Devices; Sunnyvale, Calif.). A liquid junction potential of −11.3 mV was subtracted during recordings. To measure effects on calcium channel tail currents, the tail current integral was measured before and after application of a derivative, with the integral of each trace being normalized to its peak. All experiments were carried out at room temperature (22° C.). All (R)-roscovitine derivatives were dissolved in DMSO as a 100 mM stock and stored at −20° C. For whole-cell recordings, (R)-roscovitine derivatives were diluted on the day of use into saline at a final concentration of 1-100 µM and bath applied via a glass pipette in a ~0.5 mL static bath chamber. Control recordings performed with 0.1-1% DMSO alone added to the drug delivery pipette solution revealed no significant effects on whole cell $Ca^{2+}$ currents. All other salts and chemicals were obtained from Sigma-Aldrich chemical company (St. Louis, Mo.).

Kinase inhibitory activity. Kinase inhibitory activities were determined using the EMD Millipore KinaseProfiler™ service (Millipore UK Ltd.). Each compound's kinase inhibitory activity was tested at three different concentrations (0.2 µM, 2 µM, and 20 µM) against five different kinases: Cdk1 cyclinB(h), cdk2 cyclinA(h), cdk5 p35(h), mitogen-activated protein kinase (MAPK1(h)) and myosin light-chain kinase (MLCK(h)).

Results. Compounds 13a-13x were evaluated to determine their N-type $Ca^{2+}$ channel agonist and cdk2 kinase inhibitory properties. The results are shown in Table 2. Compound 13d showed a ca. 2-fold increased agonism and a 22-fold decreased cdk2 kinase activity vs. the benchmark, (R)-roscovitine. The decreased kinase activity of 13d was attributed to the replacement of the i-propyl side chain at $R^1$ with the more flexible n-propyl group, a hypothesis that was supported by the similarly decreased cdk2 activity of 13g. The preference of the $R^1$ group for the branched i-propyl group with regard to cdk2 activity is quite pronounced, as shown for the methylated 13k, which also reduced the kinase activity ca. 8-fold. All modifications of the benzyl group at $R^2$, including the cyclopropyl-methyl group in 13g, led to complete loss of N-type $Ca^{2+}$ channel activity.

The first group at $R^2$ that proved to be an effective mimic of the benzyl group was the methylthiophenyl-substituted 13u. This compound had almost 4-fold improved $Ca^{2+}$ channel agonism, even though it was also a low nanomolar cdk2 inhibitor with a 22-fold decreased cdk2 activity compared to (R)-roscovitine. Since 13u was substituted with i-propyl at $R^1$, it was determined that replacing the i-propyl group with a methyl or an n-propyl group might produce reduced kinase inhibitory properties analogous to 13d, 13g and 13k. Indeed, this turned out to be the case. Both 13w and 13x had an $EC_{50}$=3 µM against cdk2, but the $R^1$=methyl substitution in 13w also decreased the channel activity ca. 3-fold vs 13u. In contrast, 13x proved to be a considerably more potent $Ca^{2+}$ channel agonist with an $EC_{50}$=7.2 µM for N-type channels. Thus, small changes in the $R^1$ substitution on the calcium channel affinity were surprisingly effective.

As seen in Table 2, three compounds in particular exhibited a strong agonist effect on the $Ca^{2+}$ channel tail currents: compounds 13u, 13w, and 13x (FIG. 3A). For comparison, the effect of (R)-roscovitine on N-type tail currents was also determined. By measuring the tail current integrals (first normalizing each trace to its peak tail current amplitude and then normalizing to control integrals), the $EC_{50}$ values of (R)-roscovitine, 13w, 13u and 13x were found to be 27.58 ±1.65 µM, 30.02±1.87 µM, 11.29±1.48 µM and 7.21±0.86 µM, respectively (FIG. 3B). Furthermore, the maximal fold increase in the tail current integral relative to control was ~8-fold, ~13-fold, ~25-fold and ~32-fold, when modified by (R)-roscovitine, 13w, 13u and 13x, respectively.

TABLE 2

| Compound | N-Type $Ca^{2+}$ Channel Activity $EC_{50}$ +/− SEM [µM][a] | Cdk2 Activity $EC_{50}$ +/− SEM [µM][b] |
|---|---|---|
| (R)-roscovitine | 27.58 +/− 1.65 | 0.151 +/− 0.004 |
| 13a | >100 | ND |
| 13b | >100 | ND |
| 13c | >100 | ND |
| 13d | 14.23 +/− 2.71 | 3.34 +/− 0.05 |
| 13e | >100 | ND |
| 13f | >100 | ND |
| 13g | >100 | 3.63 +/− 0.42 |
| 13h | >100 | ND |
| 13i | >100 | ND |
| 13j | >100 | ND |
| 13k | >70 | 1.44 +/− 0.02 |
| 13l | >100 | ND |
| 13m | >100 | ND |
| 13n | >100 | ND |
| 13o | >100 | ND |
| 13p | >100 | ND |
| 13q | >100 | ND |
| 13r | >100 | ND |
| 13s | >100 | ND |
| 13t | >100 | ND |
| 13u | 11.29 +/− 1.48 | 0.262 +/− 0.0002 |
| 13v | >100 | ND |
| 13w | 30.02 +/− 1.87 | 3.04 ± 0.17 |
| 13x | 7.21 ± 0.86 | 3.29 ± 0.43 |

[a]$Ca^{2+}$ channel agonist $EC_{50}$ were determined by whole cell perforated patch clamp recordings of deactivation currents from N-type channels as described in the Methods. Cpd 13k was only soluble up to 200 µM in saline with 1% DMSO, thus limiting our ability to accurately determine agonist properties.
[b]Cdk1 cyclinB(h) inhibitory $EC_{50}$ were determined in duplicate at 0.2, 2, and 20 µM agent concentrations, with roscovitine as the positive control.
ND = not determined.

In addition to increasing $Ca^{2+}$ channel agonist activity more strongly than (R)-roscovitine, a compound with reduced cdk antagonist activity was desired. A commercial kinase screen was used to test the effect of these novel compounds and (R)-roscovitine on several kinases, including cdk1, cdk2, cdk5, MAPK1, and MLCK. FIG. 3C shows the dose response curve of cdk2 inhibition by the parent molecule and the three novel compounds. The $IC_{50}$ values for cdk2 activity following exposure to (R)-roscovitine, 13w, 13u and 13x were 0.15±0.004 μM, 3.04 ±0.17 μM, 0.26±0.0002 μM and 3.29±0.43 μM, respectively (Table 3) Against cdk1, cdk5, MAPK1 and MLCK, 13x exhibited inhibitory activities $EC_{50}$=20.56±0.96, 3.03±0.32, >20, and >20 μM, respectively (Table 3), further illustrating a quite favorable low-activity kinase profile for this structure. In light of the large cellular ATP concentrations (in the 1-10 mM range), single-digit μM activities of 13x against some kinases are likely readily compensated for in vivo and are therefore not considered significant impediments from possible therapeutic applications of 13x as N/P/Q-type calcium channel agonist Taken together, the data on $Ca^{2+}$ channel and cdk activity show that 13x displays the most desirable properties of the compounds we have synthesized and tested thus far, as it displays both a greatly increased $Ca^{2+}$ channel agonist activity, and a decreased cdk2 antagonist activity, compared to the parent molecule (R)-roscovitine (Table 2). For this reason, 13x was selected as the lead compound of interest.

The agonist activity of 13x on P/Q-type channels ($Ca_v$ 2.1) and L-type ($Ca_v$ 1.3) channels was evaluated using the same voltage-clamp protocol. Compound 13x had a very similar effect on P/Q-type channels as it did on N-type channels ($EC_{50}$=8.8±1.1 μM vs. 7.21±0.86 μM for P/Q- and N-type channels, respectively). Additionally, 13x increased the tail current integral by ~33-fold compared to control, similar to its effect on N-type channels (~32-fold). Finally, 13x had no agonist activity ($EC_{50}$>100 μM) on the L-type α-subunit tested ($Ca_v$ 1.3; Table 3).

In summary, 13x greatly improved upon (R)-roscovitine in terms of our properties of interest, with a ~4-fold increase in efficacy as an agonist for N- and P/Q-type $Ca^{2+}$ channels, a ~3-4-fold increase in potentcy as an agonist for N- and P/Q-type $Ca^{2+}$ channels, and a ~20-fold decrease in potency as a cdk antagonist (FIGS. 4A-4C).

For 13x, agonist effects on P/Q-type ($EC_{50}$=9.9 uM) and L-type calcium channels ($EC_{50}$>100 uM) were evaluated. Error ranges for $EC_{50}$ values at N- and P/Q-type channels generated for 13x: 95% confidence interval for a fit to P/Q channels data=6.7-14.5 μM; 95% confidence interval for the fit to N-type channels=4.6-9.8 μM. Compound 13x was found to exhibit selectivity for N- and P/Q-type over L-type calcium channels.

EXAMPLE 2

Molecular Docking

Docking analyses to the cdk2/roscovitine complex were used to analyze predictions for interactions with (R)-roscovitine analogs. Flexible docking studies were performed using Molegro Virtual Docker (MVD, University of Aarhus, Denmark) to evaluate if the analogs bound to the (R)-roscovitine binding site of cdk2.[22] The basis of these docking studies was a new hybrid search algorithm, i.e., a guided differential evolution (DE) which combines DE optimization with a cavity prediction algorithm which is dynamically used during the docking process. Briefly, all individual ligands were initialized, evaluated and scored ($E_{score}$/MolDock Score) according to the fitness function, which is the sum of the intermolecular interaction energy between the ligand and the protein and the intramolecular interaction energy of the ligand: $E_{score}=E_{inter}+E_{intra}$, with $E_{inter}$ being the ligand-protein interaction energy and $E_{intra}$ being the internal energy of the ligand.

$E_{PLP}$ is a piecewise linear potential using two different sets of parameters: one set for approximating the steric van der Waals term between atoms and the other stronger potential for hydrogen bonds. $E_{clash}$, assigns a penalty of 1000 if the distance between two atoms (more than two bonds apart) is less than 2.0 Å. Thus, the $E_{clash}$ term punishes infeasible ligand conformations.

Offspring were created using a weighted difference of the parent solutions, which were randomly selected from the population. If, and only if, the offspring was fitter, it replaced the parent. Otherwise, the parent survived and was passed on to the next generation, representing an iteration of the algorithm. The search process was terminated when the number of fitness evaluations exceeded the maximum number of evaluations permitted.

Since the crystal structure of cdk2 (PDB ID: 3DDQ) contains (R)-roscovitine bound to the active site, it was possible to identify critical residues surrounding the binding pocket. The MolDock scoring function in combination with the MolDock SE search algorithm and Tabu clustering[23] and a search space volume of 25 Å radius encompassing the (R)-roscovitine binding domain was chosen for docking, and both the ligands and catalytic pocket residues were allowed to be flexible during the simulation. Each ligand was docked iteratively into the chosen cavity in ten independent runs, each of which consisted of 1500 steps. Poses generated from each run were subjected to Tabu clustering whereby the lowest energy pose below an energy threshold of 100 was generated as output. Thus, there were 10 poses per ligand

TABLE 3

Comparison of (R)-roscovitine and analog $EC_{50}/IC_{50}$ affinities (in μM) for activity at calcium channels and kinases

|  | N-type | P/Q-type | L-type | Cdk1 | Cdk2 | Cdk5 | MAPK | MLCK |
|---|---|---|---|---|---|---|---|---|
| (R)-roscovitine | 27.58 ± 1.65 | 120* | >100† | 0.89 ± 0.01 | 0.15 ± 0.004 | 0.14 ± 0.01 | >20‡ | >20‡ |
| 13w | 30.02 ± 1.87 | N.D. | N.D. | 10.46 ± 2.77 | 3.04 ± 0.17 | 2.81 ± 0.91 | >20‡ | >20‡ |
| 13u | 11.29 ± 1.48 | N.D. | N.D. | 1.77 ± 0.04 | 0.26 ± 0.0002 | 0.27 ± 0.01 | >20‡ | 19.45 ± 8.65 |
| 13x | 7.21 ± 0.86 | 8.81 ± 1.07 | >100† | >20‡ | 3.29 ± 0.43 | 3.03 ± 0.32 | >20‡ | >20‡ |

*Literature $EC_{50}$ values for (R)-roscovitine on N- and P/Q-type $Ca^{2+}$ channels taken from Buraei et al. (*Neuropharmacology* 2007, 52:883) and Buraei and Elmslie (*J. Neurochem* 2008, 105:1450). The experimentally measured EC50 value for (R)-roscovitine on N-type channels was 27.58 ± 1.65 μM.
†No measureable agonist effect on L-type calcium channels up to 100 μM.
‡20 μM was the highest concentration used in kinase screens, therefore an $IC_{50}$ above 20 μM could not be reliably determined.
N.D. = Not determined ranked by energy. The lowest energy pose of the 10 poses per ligand was selected for visual inspection.

For validation purposes docking was first applied to (R)-roscovitine, and the docked pose was computed to be very close to the position of the ligand in the X-ray structure (i.e. RMSD=0.27 Å). The binding free energy, as estimated by the MolDock Score (arbitrary units) was −140, which indicated a strong interaction with cdk2 binding site. The same protocol was then applied to all (R)-roscovitine analogs.

Figure 5:
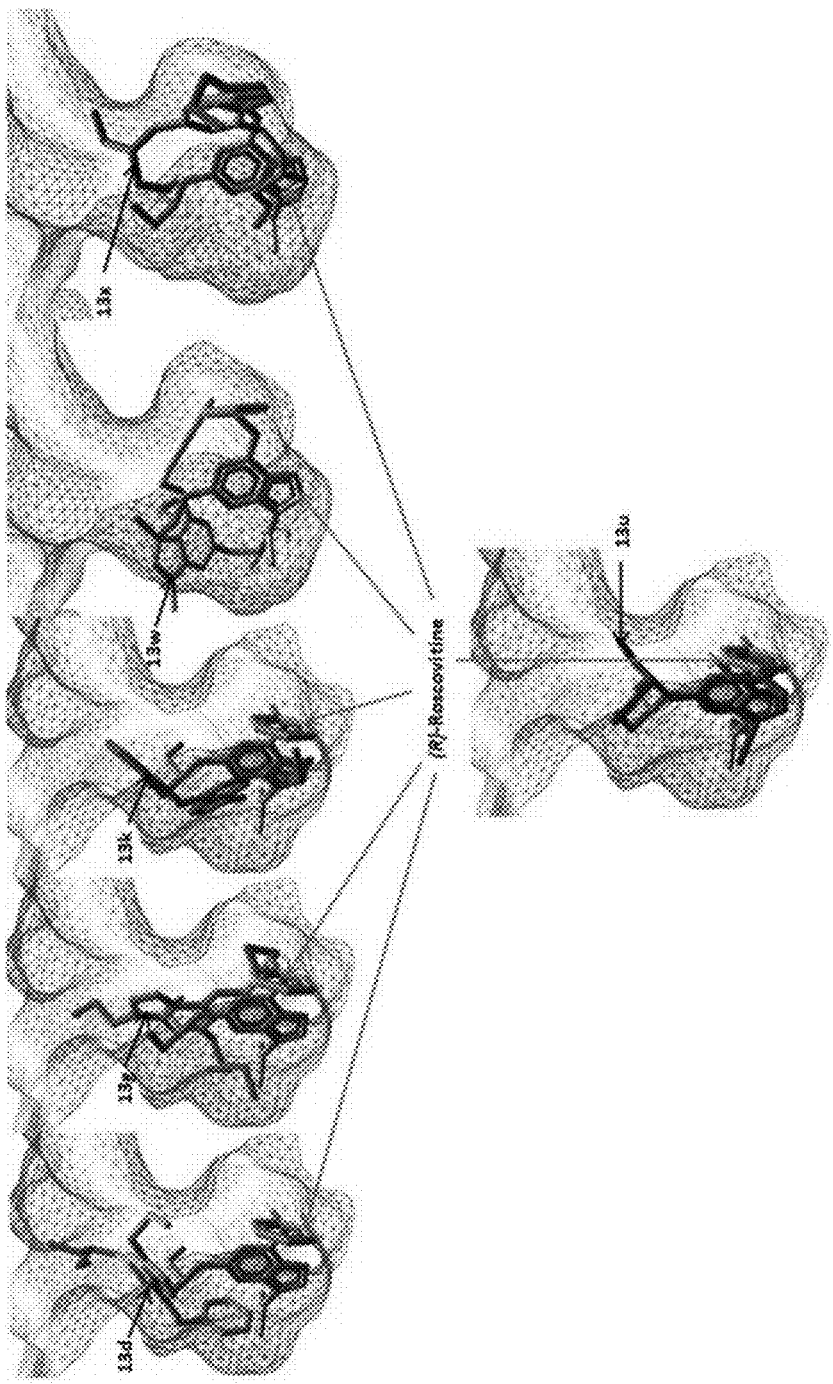
FIG. 5 illustrates molecular docking of compounds 13d, 13g, 13k, 13w, 13x and 13u to the cdk2/roscovitine complex. The electrostatic interaction surface at the binding site region is displayed and colored red for negative charge and blue for positive charge. Docking simulations were performed using Molegro Virtual Docker, taking into account side chain flexibility for all residues in the binding region.
Figure 6:
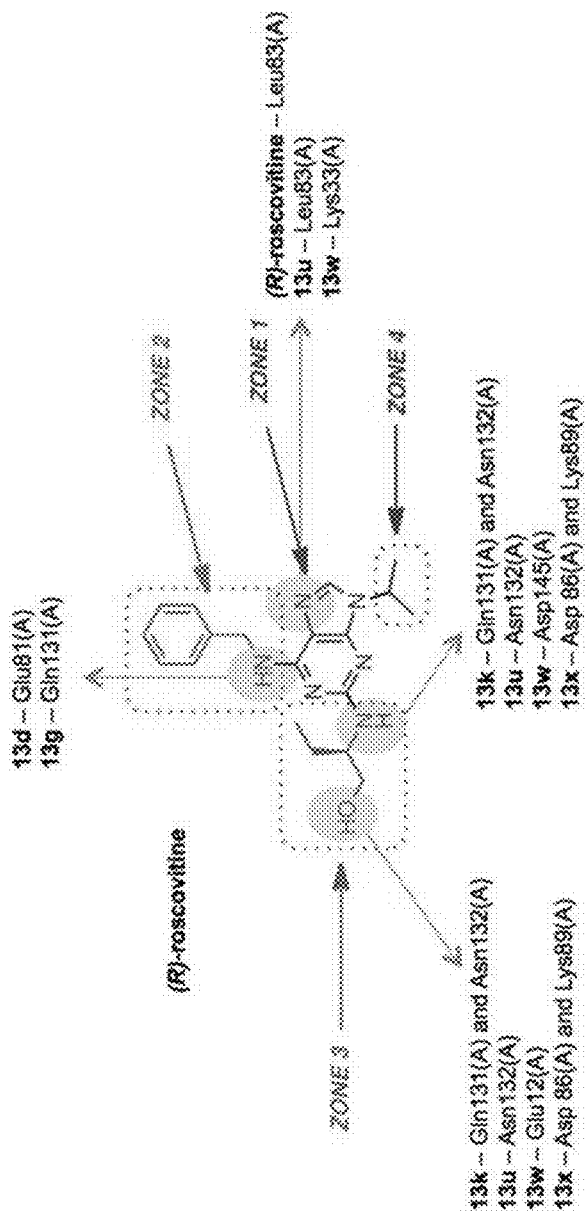
FIG. 6 illustrates hydrogen bond interactions between compounds 13d, 13g, 13k, 13u, 13w, 13x and cdk2. Interacting chemical groups of the analogs are shown in blue ellipses on the (R)-roscovitine scaffold.

The docking studies demonstrated that analogs 13d, 13g, 13k, 13w and 13x bound with a MolDock Score value between −127 and —143, and in a different orientation, less favorable than (R)-roscovitine. Compound 13u bound similarly to (R)-roscovitine with a MolDock Score of −142 (FIGS. 5 and 6). These results were consistent with the experimental data that showed this compound to retain cdk2 activity, while 13d, 13g, 13k, 13w and 13x displayed reduced cdk2 activities. These results are consistent with the experimental data that show this compound to retain cdk2 activity, while 13d, 13g, 13k, 13w and 13x displayed reduced cdk2 activities

EXAMPLE 3

Effects in LEMS Passive Transfer Model Mice

LEMS passive transfer. To test GV-58 in a LEMS model NMJ, an established LEMS passive transfer mouse model was utilized. To perform the passive transfer of LEMS, mice were injected with the serum of patients diagnosed with LEMS. Collection of serum from LEMS patients was performed following the guidelines set forth by the University of Pittsburgh Institutional Review Board (IRB). Each serum sample was tested for the presence of voltage-gated $Ca^{2+}$ channel antibodies using a $Ca^{2+}$ channel antibody radioimmune assay (Kronus RIA kit, Star, Id.). Control serum was obtained from the University of Pittsburgh Medical Center blood bank. Adult female CFW mice (2-3 months at beginning of passive transfer; 25-32 g; Charles River Laboratories) were divided into two groups: one group that received LEMS serum, and a control group that received control serum. Mice received an intraperitoneal (i.p.) injection on day 1 of the treatment phase with 300 mg/kg cyclophosphamide to suppress immune responses, and were injected i.p. once per day for 30 consecutive days with either 1.5 mL serum from LEMS patients or 1.5 mL control serum. In all cases, experimenters were blinded to the injection conditions.

Intracellular recordings at mouse NMJs. Following the passive transfer protocol, intracellular recordings to assess the LEMS-mediated deficit in transmitter release were made in an ex vivo nerve-muscle preparation. A thin upper arm muscle, the epitrochleoanconeus (ETA), was chosen for these recordings. This ex vivo nerve-muscle preparation was placed in a bath containing 118 mM NaCl, 3.45 mM KCl, 11 mM dextrose, 26.2 mM NaHCO3, 1.7 mM NaH2PO4, 0.7 mM MgCl2, 2 mM CaCl2, pH=7.4. The nerve was stimulated with a suction electrode and muscle contractions were blocked by exposure to 1 μM μ-conotoxin GIIIB (Alomone Labs). Microelectrode recordings were performed using ~40-60 MΩ borosilicate electrodes filled with 3 M potassium acetate. Spontaneous miniature synaptic events (mEPPs) were collected for 1-2 minutes in each muscle fiber, followed by single nerve evoked synaptic activity (10-30 EPPs) that was collected with an inter-stimulus interval of 10 seconds. A train of 10 EPPs was also collected in each muscle fiber using an inter-stimulus interval of 20 msec. To analyze the data, both the amplitudes and the areas under the waveforms (integral) were determined after correcting each digitized point in each trace for non-linear summation. Data were collected and analyzed using an Axoclamp 900A and the pClamp 10 suite of programs (Molecular Devices, Sunnyvale, Calif.).

Statistical Analysis. Statistical analysis was performed using either GraphPad Prism 5 (GraphPad Software, Inc.) or Origin 7 (OriginLab) software. For the dose-response analyses on $Ca^{2+}$ current, each concentration of the four different compounds was tested in 3-6 cells. For the dose-response analyses on kinase activity, each of the three concentrations was tested in duplicates (n=2) for every compound except (R)-roscovitine, which was sent for kinase screening three times (n=6 for each concentration). All $EC_{50}$ and $IC_{50}$ values and their respective errors were determined by performing 100 iterations of a logistic function curve fit. Data are presented as mean±s.e.m. unless otherwise noted.

Results. The effects of whole serum injections from 8 LEMS patients were tested by measuring the quantal content in mouse ETA neuromuscular junctions following the passive transfer protocol (FIG. 7A), and comparing them to the quantal content of mice that underwent a passive transfer protocol with injections of normal human serum. The clinical profile for each LEMS patient whose serum was studied is shown in Table 4. Several patients' serum caused no significant change in quantal content (FIG. 7A, black bars), whereas other patients' serum showed moderate to strong changes in quantal content (FIG. 7A, white bars).

TABLE 4

Clinical data of each LEMS patient from whom serum was obtained and tested.

| Patient | Age | Age at Diagnosis | CMAP increment | ANNA1 (+/−) | P/Q-type $Ca^{2+}$ channel antibodies (+/−) |
|---|---|---|---|---|---|
| PB | 62 | 52 | 500% | − | + |
| EB | 66 | 57 | 331% | − | + |
| PG | 71 | 68 | 1300% | − | + |
| JS | 56 | 42 | 109% | N.D. | − |
| aBC2 | 30 | 20 | 800-1600% | + | + |
| SH | 61 | 55 | 78% | + | + |
| LE | 54 | 45 | 400% | − | + |
| aCB | 71 | 65 | 315% | − | + |

CMAP increment is a common diagnostic marker for LEMS and refers to the increase in compound muscle action potential (CMAP) size following a short exercise period (~10 seconds; Oh et al., 2007).
ANNA1 = anti-neuronal nuclear antibody type I, which is also known as "anti-Hu".
N.D. = Not determined In addition to testing quantal content following the passive transfer protocol, an antibody radioimmune assay was also performed to determine the level of $Ca^{2+}$ channel antibodies in each patient's serum (FIG. 7B). In general, those serum samples that significantly decreased quantal content had detectable levels of $Ca^{2+}$ channel antibodies, although the level of these antibodies did not seem to correspond precisely to the level of quantal content decrease (FIGS. 7A and 7B).

The goal was to choose a single patient's serum for repeated testing of the novel calcium channel agonist (compound 13x) in order to have a consistent passive transfer effect in every mouse. For these studies, the serum from patient aBC2 was selected because the quantal content following the passive transfer with this serum (40.5±9.9; mean±SD, n=49 terminals) was significantly reduced compared to control serum (102.4±25.1; mean±SD, n=41 terminals, p<0.05, one-way ANOVA with Tukey's post-hoc test; FIG. 7A, 7C). EPP amplitude following passive transfer with aBC2 serum was also significantly smaller than EPP amplitude of NMJs injected with control serum (14.15±0.64 mV, n=49 vs. 34.61±1.37 mV, n=41 for aBC2 serum-treated NMJs and control serum-treated NMJs, respectively; p<0.05, Student's t-test), but mEPP amplitude was not significantly different between the two conditions (data not shown). Additionally, there was sufficient serum from this patient to perform all of the desired experiments. Therefore, all of the following studies were performed using mice that underwent the passive transfer protocol using serum aBC2.

Figures 8A, 8B, 8C, 8D, 8E:
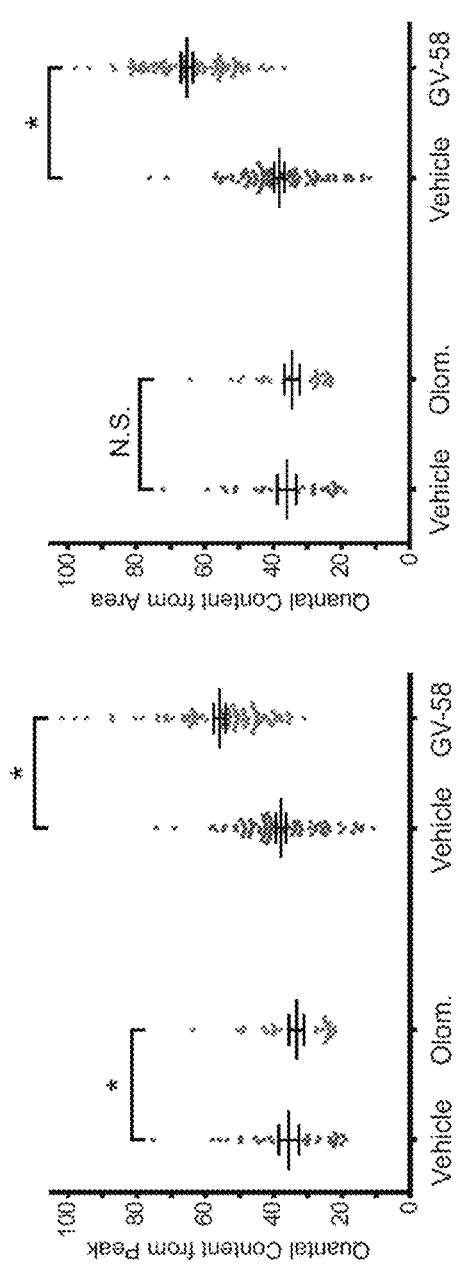
FIG. 8A shows sample traces (overlay of 10 traces in each example) showing the increase in EPP amplitude following a 30-minute incubation in 50 μM 13x relative to vehicle control (0.05% DMSO).
FIG. 8B is an average of 10 traces from the same NMJ before (vehicle) and after 30-minute incubation in 50 μM 13x show a 13x-induced widening of the EPP trace.
FIG. 8C shows representative mEPP traces from the same NMJ before and after 13x application.
FIG. 8D illustrates that the quantal content determined by measuring the peak (peak EPP amplitude divided by the average peak mEPP amplitude) was slightly, but significantly smaller following 50 µM oloumucine (Olom.) application, but was significantly increased following 13x application. The scatter plot represents the variability between individual synapses studied. Error bars indicate s.e.m.
FIG. 8E shows that the quantal content determined by measuring the area (EPP area divided by average mEPP area) was not significantly different following 50 µM oloumucine (Olom.) application, but was significantly increased following 13x application. The scatter plot represents the variability between individual synapses studied. Error bars indicate s.e.m.

Compound 13x was tested in the LEMS model mice. Having developed a consistent LEMS passive transfer protocol, the effect of compound 13x on action potential-evoked transmitter release from LEMS passive transfer mouse NMJs was evaluated. EPP amplitude and quantal content were determined in the vehicle (0.05%-0.1% DMSO) before a 30-minute incubation in 50 μM 13x (FIG. 8A), which was then followed by repeated EPP amplitude and quantal content measurements from the same NMJs with the 13x still present in the bath. EPP amplitude was significantly increased from 13.00±0.56 mV (n=73 terminals) in vehicle-treated aBC2 serum NMJs to 19.44±0.98 mV (n=73 terminals; p<0.05, Student's paired t-test) following application of 50 μM 13x. The quantal content (determined by dividing the EPP peak amplitude by the mEPP peak amplitude) in the LEMS passive transfer vehicle control NMJs was 38.0±12.8 (mean±SD, n=73 terminals), and was significantly increased after 13x exposure to 56.0±15.2 (mean±SD, n=73 terminals; p<0.05, Student's paired t-test; FIG. 8D). Furthermore, when the quantal content was determined from the area (integral) under EPP and mEPP waveforms, the quantal content in the vehicle controls was 38.3±12.7 (mean±SD, n=73 terminals), and was significantly increased to 65.6±15.0 (mean±SD, n=73 terminals; p<0.05, Student's paired t-test; FIG. 8E) following 13x application. The difference between the compound's effect on quantal content when measuring peak (~62% increase) compared with its effect on quantal content when measuring area (~92% increase) suggests that there is a broadening of the EPP waveform caused by the action of 13x on $Ca^{2+}$ channels (expected based on the 13x-mediated slowing of $Ca^{2+}$ current deactivation).

To further explore this possibility, both the full width at half maximum (FWHM) and the 90% to 10% decay time before and after 13x application were measured. FIG. 8B shows an overlay of the average EPP amplitudes in a sample NMJ before (vehicle) and after 13x application. The FWHM increased significantly from 3.39±0.06 ms in the vehicle controls (n=73 terminals) to 3.90±0.07 ms following 50 μM 13x application (n=73 terminals; p<0.05, Student's paired t-test). Similarly, the 90% to 10% decay time increased from 5.84 ±0.12 ms in vehicle controls (n=73 terminals) to 6.79±0.11 ms following 13x application (n=73 terminals; p<0.05, Student's paired t-test). This indicates that the effect of 13x cannot fully be appreciated by only observing changes in peak EPP amplitude. Overall, 13x was shown to increase the strength of neuromuscular transmission by about 50%. Because 13x increased the mean open time of the calcium channels that trigger transmitter release, a slight broadening of the time-course of acetylcholine release resulted in a slight, but significant expansion of the post-synaptic potentials (FIG. 8B). These studies demonstrated that calcium channel agonists like 13x can reverse neuromuscular weakness.

To ensure that the observed effect of 13x on transmitter release was not due to inhibition of cdks, we tested the effect of olomoucine on transmitter release at LEMS passive transfer mouse NMJs. Olomoucine is a compound that is structurally related to (R)-roscovitine and has potent cdk inhibitory activity, but no $Ca^{2+}$ channel activity.

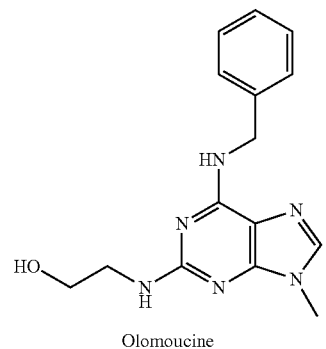 [SMILES: Cn1cnc2c(NCc3ccccc3)nc(NCCO)nc21]

Olomoucine

Application of 50 μM olomoucine caused a slight decrease in quantal content compared to vehicle controls when measuring quantal content from peak (35.7±15.0, mean±SD, n=23 vs. 33.4±11.3, mean±SD, n=23, for vehicle controls and olomoucine, respectively; n<0.05, Student's paired t-test; FIG. 8D). The quantal content measured from area in vehicle controls (36.1 ±14.3, mean±SD, n=23) did not significantly change after application of olomoucine (34.6±11.2, mean±SD, n=23; p=0.16, Student's paired t-test; FIG. 8E). Therefore, the effects of 13x on increasing action potential-evoked transmitter release at LEMS passive transfer NMJs appear to be due to effects on $Ca^{2+}$ channels rather than effects on cdks.

In addition to analyzing the changes in quantal content and EPP kinetics, the effect of 13x on spontaneous transmitter release was analyzed. FIG. 8C shows sample mEPP traces recorded in the vehicle control and following 50 uM 13x application. The mEPP frequency was significantly increased from 3.27±0.15 $s^{-1}$ (n=73) in vehicle controls to 10.45 ±0.64 $s^{-1}$ (n=73) following application of 50 μM 13x (p<0.05, Students paired t-test). Furthermore, the mEPP amplitude did not significantly change following addition of 13x (mean change in amplitude following 13x=1.00±0.02, n=73; p=0.86, Student's one sample t-test), thus confirming a presynaptic locus for effects.

Interestingly, some NMJs showed more than a 3-fold increase in transmitter release after exposure to 13x, while others showed a very small effect (see scatter plots in FIGS. 8D and 8E). There were several potential sources of variability in 13x effects on quantal content. First, during the relatively short (30-60 minutes) exposure, there may have been variable connective tissue barriers to diffusion, which may have resulted in different concentrations of 13x affecting particular NMJs within the muscle. It is also possible that the mix of calcium channels at LEMS model synapses was variable when compared between NMJs (even in the same muscle). Compensatory changes in $Ca^{2+}$ channel expression have been reported to include an up-regulation of L-type $Ca^{2+}$ channel expression at the NMJ that might contribute to the triggering of release at these disease model synapses, but L-type channels would not be sensitive to modulation by 13x (see Table 3).

Finally, the effect of 13x on short-term plasticity was determined by eliciting a train of 10 stimuli at 50 Hz before and after application of 50 µM 13x in the LEMS passive transfer model NMJs (FIGS. 9A, 9B). In the control serum condition, there was almost no facilitation, and by the $10^{th}$ EPP in the train there was a depression to about 66% of the first EPP. The trains of stimuli in the "aBC2" condition triggered EPPs that were generally erratic in size during any single train, but the overall average showed facilitation throughout the 50 Hz train, with a peak facilitation of ~120% at EPP 4 and a small facilitation of ~105% remaining at the final EPP in the train. When normalized to the first EPP of the train, the control serum condition (n=41) was significantly different than the "aBC2" condition (n=52) at each EPP in the train following the first ($p<0.05$, Student's t-test; FIGS. 9A, 9B).

The short-term plasticity characteristics before (0.05-0.1% DMSO vehicle) and after application of 50 µM 13x in the LEMS passive transfer model NMJs were then compared (FIGS. 9C, 9D). The "Vehicle" condition showed facilitation throughout, with a facilitation of ~113% remaining at the final EPP in the train. Following the application of 50 µM 13x in the same NMJs, there was a slight facilitation followed by depression to about 94% at the final EPP in the train. Furthermore, the "13x" condition was significantly different from the "Vehicle" condition at every EPP following the first when both conditions were normalized to the first EPP of the train ($p<0.05$, Student's paired t-test; FIGS. 9C, 9D).

Representative traces in FIGS. 9A and 9C were chosen to display the differences in short-term plasticity characteristics rather than the differences in the first EPP's amplitude, which were quite variable (see FIG. 8) among the four conditions. Asterisks in FIGS. 9B and 9D indicate a significant difference between the two normalized EPP amplitudes below each asterisk as determined by a Student's t-test in FIG. 9B or a Student's paired t-test in FIG. 9D. Error bars indicate s.e.m.

Compound 13x increased the amount of $Ca^{2+}$ influx through channels that open during an action potential, which in turn led to an increase in the amount of transmitter released (see, e.g., FIGS. 8A-8E). When determining how such a use-dependent agonist would increase transmitter release at the mammalian NMJ, it is useful to consider the calcium-dependent mechanisms that normally regulate release at this synapse. The adult mouse NMJ has been shown to contain ~850 very small active zones, each of which contains about two docked synaptic vesicles. Because the entire adult mouse ETA neuromuscular synapse releases about 100 vesicles normally following each action potential stimulus (FIGS. 7A-7C), the probability of release from each active zone is about 12%. Therefore, if each active zone only releases a synaptic vesicle approximately 1 out of every 10 stimuli, the coupling between calcium channel opening and vesicle fusion in these active zones may be very low. Under these conditions, a use-dependent calcium channel agonist like 13x would be expected to increase the flux through a subset of open channels, increasing the probability of vesicle fusion at these sites.

One interesting observation was the lack of facilitation in the 50 Hz train in control serum NMJs compared to the large facilitation present in the 50 Hz train in LEMS serum-treated NMJs. If many $Ca^{2+}$ channels contribute to the release of a single vesicle within each active zone, as has been shown in multiple CNS synapses (, then the large facilitation in the LEMS serum-treated NMJs would be caused by a smaller intracellular $Ca^{2+}$ flux through fewer calcium channels at each active zone. Compound 13x would then compensate by increasing the $Ca^{2+}$ influx through the remaining $Ca^{2+}$ channels at the active zone. If, however, the mouse NMJ functions as has been reported at the frog NMJ, there may be a roughly one-to-one relationship between $Ca^{2+}$ channel opening and vesicle fusion. Under these conditions at the small, isolated active zones present at the mouse NMJ, an explanation for the increase in facilitation observed in the LEMS serum-treated NMJs is less straightforward. In this scenario, if the opening of one $Ca^{2+}$ channel normally contributes to the release of one vesicle ($Ca^{2+}$ channel–release site cooperativity=1), then simply removing $Ca^{2+}$ channels (as a result of LEMS) should only reduce quantal content without affecting short-term plasticity since each release site that lost a calcium channel would simply drop out, with no change in the calcium flux at release sites that had a calcium channel opening. On the other hand, if there is a compensatory expression of other types of $Ca^{2+}$ channels in LEMS NMJs, this may result in the insertion of $Ca^{2+}$ channels into sites further away from the vesicle and its release machinery. This could lead to a $Ca^{2+}$-release site coupling such that it might be required that more than one open $Ca^{2+}$ channel provide the flux that is necessary for the release of a single vesicle. Under these conditions, one would predict an increased facilitation during a 50 Hz train compared to control. Compound 13x would then reverse this by increasing the $Ca^{2+}$ influx through each channel, thus increasing the likelihood that the flux through a single channel could trigger the release of a synaptic vesicle. Lastly, it is also possible that active zone structure and organization is disrupted in the LEMS passive transfer NMJ. Disruption of active zone structure and organization could alter the normally one-to-one $Ca^{2+}$ channel-to-vesicle coupling, thus accounting for both the facilitation seen in the LEMS serum-treated NMJs and the partial restoration of short-term plasticity characteristics by 13x as described above. LEMS could induce active zone disorganization in this scenario by disrupting the interactions between $Ca^{2+}$ channels and active zone proteins following the autoimmune-mediated removal of $Ca^{2+}$ channels. For example, previous work has shown that preventing the interaction between $Ca^{2+}$ channels and the active zone protein laminin p2 induces active zone disorganization similar to that seen in LEMS NMJs.

EXAMPLE 4

Figure 10A:
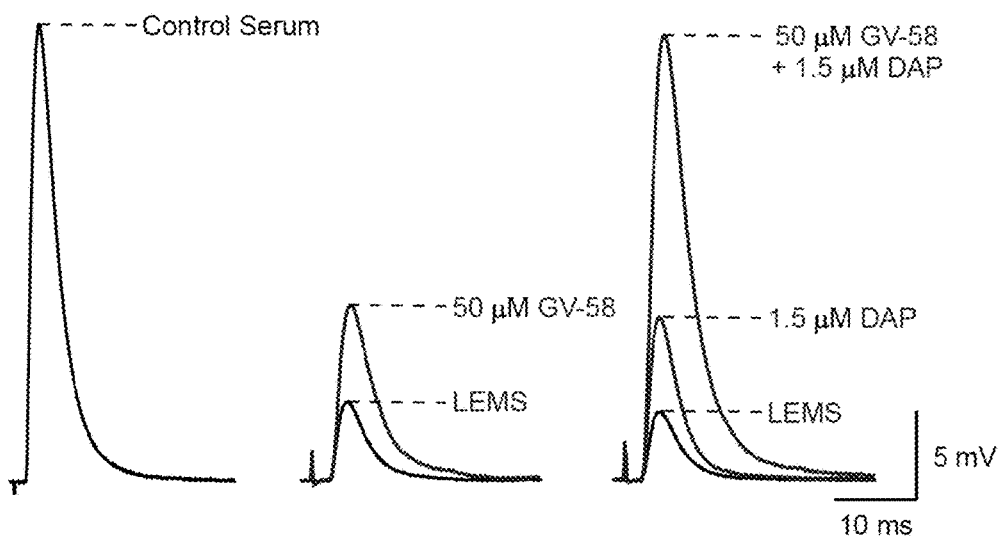
FIGS. 10A and 10B. The synergistic effect of GV-58 plus DAP completely reverses the deficit in neurotransmitter release at LEMS model NMJs.
Figure 10B:
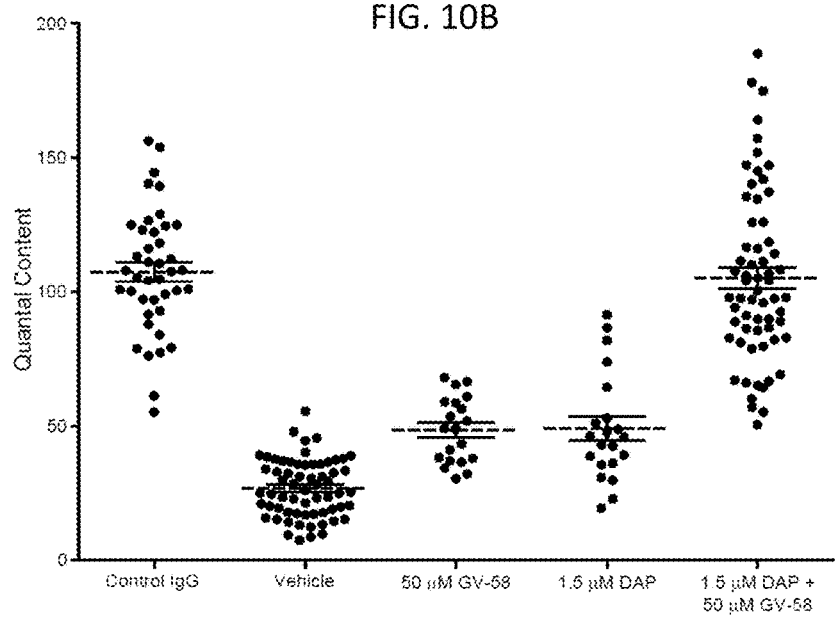

Synergistic Action of DAP and 13x Completely Reverses Neuromuscular Weakness at LEMS Mode NMJs The patch clamp data show that 13x has a greater effect when more $Ca^{2+}$ channels are open, which would occur when the depolarizing stimulus is longer in duration. This suggests the intriguing possibility that DAP (the current most common treatment for LEMS) and 13x would have a synergistic interaction because DAP opens more $Ca^{2+}$ channels by prolonging the duration of the presynaptic action potential. To test this, intracellular microelectrode recordings were performed on ex vivo nerve-muscle preparations taken from LEMS passive-transfer model mice and measured the magnitude of acetylcholine released at the neuromuscular junction. The most sensitive method of quantifying the magnitude of acetylcholine released is to determine the quantal content. Quantal content is defined as the number of neurotransmitter-containing synaptic vesicles that are released from the nerve terminal during a single action potential stimulus. This value was determined by first measuring the area under the average action potential-evoked endplate potential (EPP) and then dividing this value by the area under the average single vesicle release event (miniature endplate potential; mEPP). This value could be compared between experimental groups to provide an accurate measurement of changes in the magnitude of acetylcholine released during a single action potential. Using this approach, the quantal content among five experimental conditions was compared: control NMJs, LEMS NMJs, LEMS NMJs exposed to 50 µM 13x, LEMS NMJs exposed to 1.5 µM DAP, and LEMS NMJs exposed to 50 µM 13x+1.5 µM DAP (FIG. 10). A concentration of 1.5 µM DAP was used because previous studies have reported that oral administration of DAP to patients leads to peak serum levels of ~70-150 ng/ml, which corresponds to a concentration of ~0.5-1.5 µM. First, NMJs taken from LEMS model mice show significantly reduced quantal content (QC=26.7±1.4; EPP amplitude=10.18±0.62 mV) as compared with control serum treated mouse NMJs (QC=107.5±3.6; EPP amplitude=34.62±1.37 mV; Tarr et al., 2013). After exposure to 50 µM 13x, the quantal content in these LEMS NMJs was significantly larger (QC=48.4±2.7; EPP amplitude=13.75±1.244 mV). In fact, this 13x-mediated enhancement was very similar to what was observed after exposure of LEMS model NMJs to 1.5 µM DAP (QC=49.0±4.4; EPP amplitude=17.94±1.381 mV). Interestingly, when LEMS model NMJs were exposed to a combination of 50 µM 13x plus 1.5 µM DAP, quantal content increased so much (QC=105.1±4.0; EPP amplitude=32.30±1.85 mV) that it was not significantly different from the quantal content we measured from NMJs taken from control serum-treated mice (QC=107.5±3.6; EPP amplitude=34.62±1.37 mV; Tarr et al., 2013). These data indicate that transmitter release in LEMS model NMJs was completely restored to control levels when exposed to both 13x and DAP (FIG. 10b). In summary, while either 13x or DAP alone caused about an 80% increase in transmitter release from LEMS model NMJs, the combination of 13x plus DAP caused about a 300% increase in transmitter release.

In addition to measuring the properties of individual action potential-evoked events, the short-term plasticity characteristics among all of the conditions by eliciting a train of 10 stimuli at 50 Hz was also measured and compared (FIG. 11). In NMJs taken from mice injected with control patient serum, the magnitude of transmitter release did not change much during the first few stimuli in the train and depressed slightly to 66% of control levels by the $10^{th}$ stimulus in the train. In contrast, LEMS model NMJs showed strong facilitation throughout the train, with the $10^{th}$ EPP showing facilitation to ~148% of the first EPP. Both the 50 µM 13x condition ($10^{th}$ EPP at ~123% of the first EPP) and the 1.5 µM DAP condition ($10^{th}$ EPP at ~132% of the first EPP) showed only a partial restoration of short-term plasticity characteristics. However, when the combination of 50 µM 13x plus 1.5 µM DAP was given there was a near complete restoration of short-term plasticity characteristics, with a small amount of facilitation during the first few EPPs of the train and a depression at the $10^{th}$ EPP to ~73% of the first EPP (FIG. 11). The slight differences in short-term plasticity that persist in LEMS model NMJs treated with a combination of 13x plus DAP may be due to several factors. First, even though the combined effects of 13x and DAP can completely restore transmitter release magnitude in LEMS model NMJs, this occurs by enhancing both the probability of opening (DAP) and the flux of calcium (13x) through the fewer than normal numbers of $Ca^{2+}$ channels that remain in the active zone of these LEMS model NMJs. The enhanced $Ca^{2+}$ flux at fewer than the normal number of $Ca^{2+}$ entry sites in these nerve terminals would be predicted to create a different spatial and temporal profile of presynaptic $Ca^{2+}$ concentration following each action potential stimulation, which may enhance the residual calcium effects that critically influence short-term synaptic plasticity. Second, previous freeze-fracture electron microscopic studies of LEMS active zones have revealed a disruption in the organization of presynaptic proteins (presumed to include calcium channels). If this disruption changes the spatial distance between the remaining presynaptic calcium channels and docked synaptic vesicles that are ready for release, this may also affect short-term synaptic plasticity at these synapses.

Overall, the data show that exposure of LEMS model mouse NMJs to a combination of DAP plus the novel $Ca^{2+}$ channel agonist (13x) completely reverses the deficit in neurotransmitter release, which underlies the neuromuscular weakness that is characteristic of LEMS NMJs. This effect of the two compounds is not simply an additive effect, but rather a synergistic interaction, which is expected based on the mechanism of action of each compound.

Cell lines. For evaluation of effects of 13x on P/Q-type channels, tsA-201 cells were transiently transfected with $Ca_v2.1$ in combination with $Ca_v\beta_3$ and $Ca_v\alpha_2\delta_1$ (Addgene, Cambridge, Mass.) using FuGENE 6 (Promega, Madison, Wis.). SH-SY5Y cells were used to evaluate Cdk antagonist effects in the cell survival assay. All cells were maintained in DMEM supplemented with 10% (tsA-201) or 15% (SH-SY5Y) fetal bovine serum.

Cell survival assay. A previously described, MTS-based cell survival assay using SH-SY5Y cells was used to test Cdk antagonist effects in the presence of physiological levels of ATP. The MTS reagent (CellTiter 96® kit, Promega) is cell permeable and is reduced to a colored product in viable cells that can be measured by the absorbance at 490 nm. Briefly, SH-SY5Y cells were plated into 96-well clear-bottom plates. After 24 hours of drug treatment, the MTS reagent was added and absorbance at 490 nm was determined using an Infinite® Pro 200 microplate reader (Tecan). The absorbance values in the drug-treated wells were normalized to the absorbance values in wells containing the vehicle (0.05% DMSO). Background absorbance was determined in wells containing no cells and was subtracted from all values.

Whole-cell perforated patch-clamp recordings. To assess the effects of 13x, whole-cell currents through $Ca^{2+}$ channels were recorded using perforated patch methods as previously described (Tarr et al., 2013). The pipette solution consisted of 70 mM $Cs_2SO_4$, 60 mM CsCl, 1 mM $MgCl_2$, 10 mM 4-(2-hydroxyethyl)-1-piperazineethanesulfonic acid (HEPES) at pH 7.4. The extracellular saline contained 130 mM choline chloride (ChCl), 10 mM tetraethylammonium chloride (TEA-Cl), 2 mM $CaCl_2$, 1 mM $MgCl_2$, 10 mM HEPES, at pH 7.4. Patch pipettes were fabricated from borosilicate glass and pulled to a resistance of ~1 MΩ. Capacitive currents and passive membrane responses to voltage commands were subtracted from the data. A liquid junction potential of −11.7 mV was subtracted during recordings. Currents were amplified by an Axopatch 200B amplifier, filtered at 5 KHz, and digitized at 10 KHz for subsequent analysis using pClamp 10 software (Molecular Devices; Sunnyvale, Calif.). The tail current integral was measured before and after application of a compound, with the integral of each trace normalized to its peak. All experiments were carried out at room temperature (22° C.). 13x was bath applied via a glass pipette in a ~0.5 mL static bath chamber during whole cell recordings of calcium current. All other salts and chemicals were obtained from Sigma-Aldrich (St. Louis, Mo.).

LEMS passive transfer. To test 13x in a LEMS model NMJ, we utilized an established LEMS passive transfer mouse model (Fukunaga et al., 1983; Lang et al., 1984; Fukuoka et al., 1987; Smith et al., 1995; Xu et al., 1998; Flink and Atchison, 2002). Collection of serum from LEMS patients was performed following the guidelines set forth by the University of Pittsburgh Institutional Review Board (IRB). Serum from patient aBC2 was used for all studies reported here and was collected using plasmapheresis. The serum was filtered with a 0.22 μm filter prior to the injection protocol. Adult female CFW mice (2-3 months old at beginning of passive transfer; weighing 25-32 g; Charles River Laboratories, Wilmington, Mass.) received an intraperitoneal (i.p.) injection on day 1 of the treatment phase with 300 mg/kg cyclophosphamide to suppress immune responses, and then were injected i.p. once per day for 15-30 consecutive days with 1.5 mL serum from LEMS patient aBC2. In all cases, experimenters were blinded to the injection conditions.

Intracellular recordings at mouse NMJs. Following the passive transfer protocol, intracellular recordings to assess the LEMS-mediated deficit in transmitter release were made in the mouse epitrochleoanconeus (ETA) ex vivo nerve-muscle preparation in accordance with procedures approved by the University of Pittsburgh Institutional Animal Care and Use Committee as previously described (Tarr et al., 2013). The extracellular saline contained 150 mM NaCl, 5 mM KCl, 11 mM dextrose, 10 mM HEPES, 1 mM $MgCl_2$, 2 mM $CaCl_2$, pH=7.3-7.4. The nerve was stimulated with a suction electrode and muscle contractions were blocked by exposure to 1 μM μ-conotoxin GIIIB (Alomone Labs, Jerusalem, Israel). Microelectrode recordings were performed using ~40-60 MΩ borosilicate electrodes filled with 3 M potassium acetate. To obtain the data required to calculate quantal content, spontaneous miniature synaptic events (mEPPs) were collected for 1-2 minutes in each muscle fiber, and then 10-30 nerve-evoked synaptic events (EPPs) were collected with an inter-stimulus interval of 5 seconds. Each digitized point in each trace was corrected for non-linear summation (McLachlan and Martin, 1981). To calculate quantal content, the integral of signal under the average EPP was divided by the integral of signal under the average mEPP recorded from each NMJ. This ratio calculates the average number of quanta (packages of neurotransmitter stored in synaptic vesicles) that are released following each presynaptic action potential. To evaluate effects on short-term synaptic plasticity, a train of 10 EPPs with an inter-stimulus interval of 20 msec (50 Hz) was collected in each muscle fiber. In some recordings the protocol involved first performing vehicle (0.05% DMSO) control recordings, then recording in the same muscle fibers after a 30-60 minute incubation in either 50 μM 13x or 1.5 μM DAP, and finishing with recordings in the same muscle fibers again after a 30-60 minute incubation in a combination of 50 μM 13x plus 1.5 μM DAP. In other cases, we recorded from a group of muscle fibers in which we only recorded vehicle controls before recording in the same muscle fibers following a 30-60 minute incubation in a combination of 50 μM 13x plus 1.5 μM DAP. Data were collected using an Axoclamp 900A and digitized at 10 kHz for subsequent analysis using pClamp 10 software (Molecular Devices, Sunnyvale, Calif.).

Statistical analysis. Statistical analysis was performed using either GraphPad Prism 5 (GraphPad Software, Inc., La Jolla, Calif.) or Origin 7 (OriginLab Corporation, Northampton, Mass.). Data are presented as mean±s.e.m. unless otherwise noted. A one-way ANOVA with Tukey's post-hoc test was used to determine differences among groups unless otherwise noted. The significance level was set at $p<0.05$ for all tests.

EXAMPLE 5

Compound 13x is Not Toxic to Cells Grown in Culture

Figure 12:
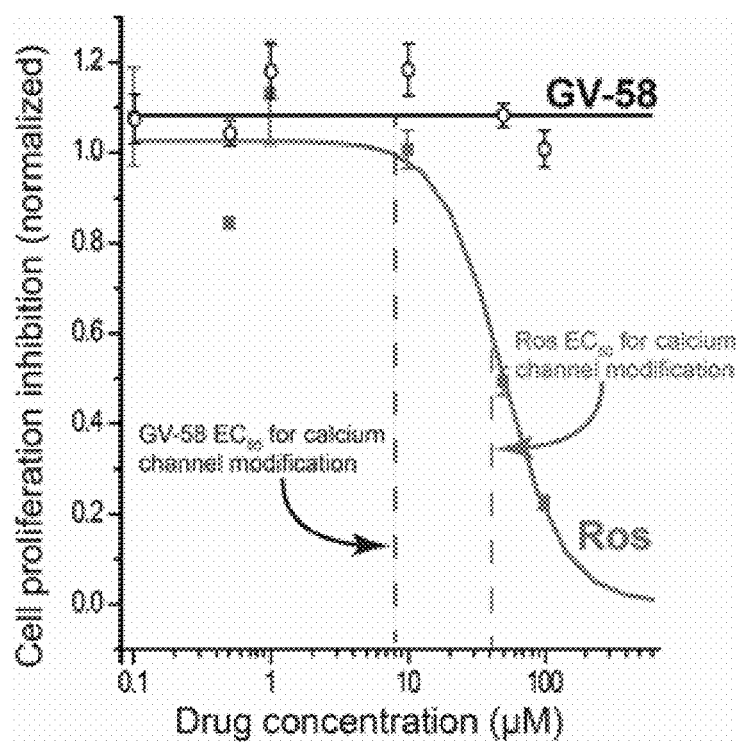
FIG. 12 is a graph of data regarding cell toxicity for compound 13x.
Figure 13:
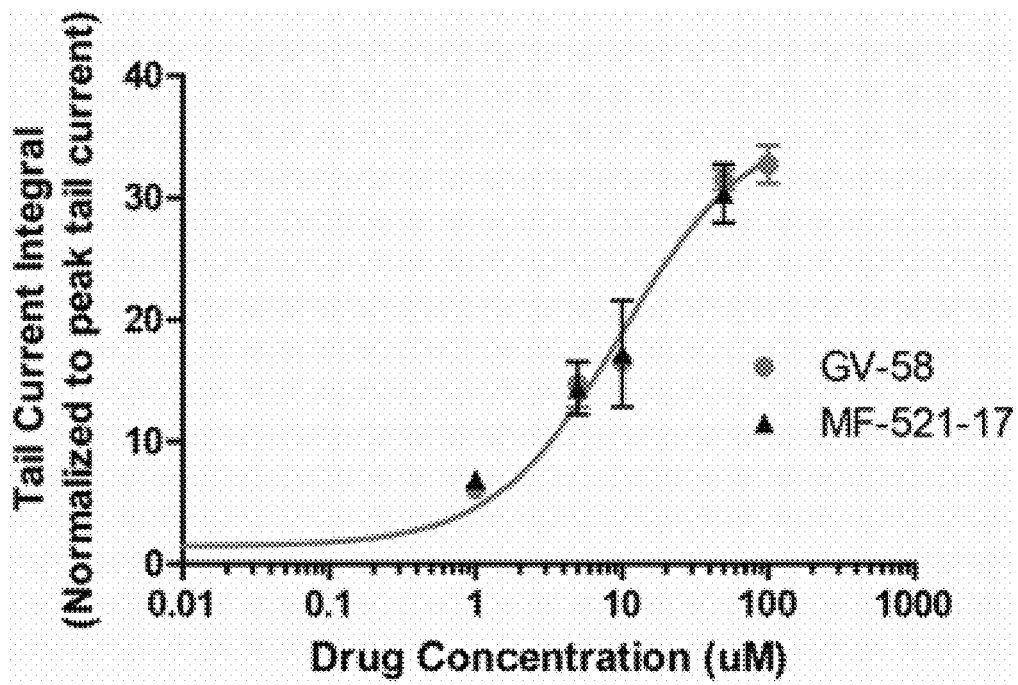
FIG. 13 is a graph of data regarding the dose-response effect on calcium channels of compound MF-521-17 (also referred to herein as compound 9).

Using a neuroblastoma cell line that is commonly used to evaluate cell cycle kinase inhibitors (SH-SY5Y cell line), when physiological concentrations of ATP are present in cells, 13x (also referred to as "GV-58") does not cause any effects on cyclin-dependent kinases or create any toxicity (while Roscovitine, the parent molecule, does). See FIG. 12.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

We claim:

1. A method for inhibiting or relieving Lambert-Eaton Myasthenic Syndrome, comprising:
administering to a subject having, or suspected of having, Lambert-Eaton Myasthenic Syndrome, a therapeutically effective amount of a compound having a structure according to formula I or a pharmaceutically acceptable salt thereof:

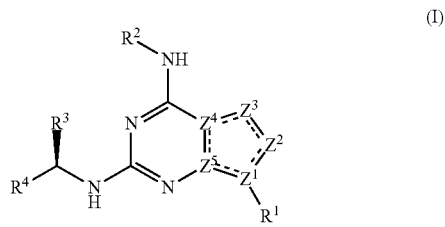

wherein each bond depicted as " ------ " is a single bond or a double bond as needed to satisfy valence requirements;
$Z^1$, $Z^2$, $Z^3$, $Z^4$, and $Z^5$ independently are nitrogen or carbon;
$R^1$ and $R^3$ are alkyl;
$R^2$ is substituted or unsubstituted thiophenyl methyl; and
$R^4$ is alkyl or hydroxyalkyl.

2. The method of claim 1, wherein the compound has a $Ca^{2+}$ channel activity half maximal effective concentration, $EC_{50}$, of ≤50 μM.

3. The method of claim 1, wherein the compound has a cyclin-dependent kinase 2 $EC_{50}$ of at least 0.2 μM.

4. The method of claim 1, wherein the compound has an N-type and/or P/Q-type $Ca^{2+}$ channel activity $EC_{50}$ that is at least 10-fold less than an L-type $Ca^{2+}$ channel activity $EC_{50}$ of the compound.

5. The method of claim 1, further comprising administering to the subject a therapeutically effective amount of an acetylcholinesterase inhibitor, an immunosuppressant, intravenous immunoglobulins, a glucocorticoid, ascorbic acid, an anti-cancer agent, a potassium channel blocker, a copper supplement, an analgesic, an antidepressant, a muscle relaxant, or a combination thereof.

6. The method of claim 5, wherein the method further comprises administering to the subject a therapeutically effective amount of 3,4-diaminopyridine.

7. The method of claim 1, wherein two of $Z^1$, $Z^2$, $Z^3$, $Z^4$, and $Z^5$ are nitrogen.

8. The method of claim 1, wherein $Z^1$ and $Z^3$ are nitrogen, and $Z^2$, $Z^4$, and $Z^5$ are carbon.

9. The method of claim 1, wherein $R^3$ is ethyl.

10. The method of claim 1, wherein $R^4$ is —CH$_2$OH.

11. The method of claim 1, wherein $R^1$ is n-alkyl.

12. The method of claim 1, wherein $R^1$ is $C_1$-$C_3$ alkyl.

13. The method of claim 1, wherein $R^2$ is:

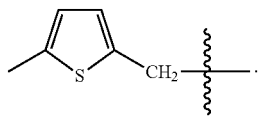 [SMILES: *Cc1ccc(C)s1]

14. The method of claim 1, wherein $Z^3$ and $Z^4$ are nitrogen, and $Z^1$, $Z^2$ and $Z^5$ are carbon.

15. The method of claim 1, wherein $R^1$ is substituted alkyl.

16. The method of claim 1, wherein $R^1$ is cyclic alkyl.

17. The method of claim 1, wherein $Z^1$, $Z^2$ and $Z^3$ are nitrogen, and $Z^4$ and $Z^5$ are carbon.

18. The method of claim 13, wherein $R^4$ is —CH$_2$OH.

19. The method of claim 18, wherein $R^3$ is ethyl.

20. The method of claim 13, wherein $Z^1$ and $Z^3$ are nitrogen, and $Z^2$, $Z^4$, and $Z^5$ are carbon.

21. The method of claim 13, wherein $Z^3$ and $Z^4$ are nitrogen, and $Z^1$, $Z^2$ and $Z^5$ are carbon.

22. The method of claim 13, wherein $Z^1$, $Z^2$ and $Z^3$ are nitrogen, and $Z^4$ and $Z^5$ are carbon.

23. The method of claim 13, wherein the method further comprises administering to the subject a therapeutically effective amount of 3,4-diaminopyridine.

24. The method of claim 15, wherein the method further comprises administering to the subject a therapeutically effective amount of 3,4-diaminopyridine.

25. The method of claim 1, wherein the structure is:

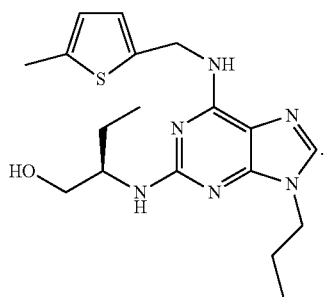 [SMILES: CCCn1cnc2c(NCc3ccc(C)s3)nc(N[C@H](CC)CO)nc21]

26. The method of claim 25, wherein the method further comprises administering to the subject a therapeutically effective amount of 3,4-diaminopyridine.

* * * * *